US007485618B2

(12) United States Patent
Day et al.

(10) Patent No.: US 7,485,618 B2
(45) Date of Patent: Feb. 3, 2009

(54) FGF-5 SUPPORTED AND BINDING PEPTIDES

(75) Inventors: Anthony G. Day, San Francisco, CA (US); Christopher J. Murray, Soquel, CA (US); Scott D. Power, San Bruno, CA (US); Beverley Rider Turnquest, San Jose, CA (US)

(73) Assignee: Genencor International, Inc., Palo Alto, CA (US)

( * ) Notice: Subject to any disclaimer, the term of this patent is extended or adjusted under 35 U.S.C. 154(b) by 342 days.

(21) Appl. No.: 10/984,410

(22) Filed: Nov. 8, 2004

(65) Prior Publication Data

US 2005/0238607 A1 Oct. 27, 2005

Related U.S. Application Data

(60) Provisional application No. 60/531,207, filed on Dec. 19, 2003, provisional application No. 60/531,189, filed on Dec. 19, 2003, provisional application No. 60/530,954, filed on Dec. 19, 2003, provisional application No. 60/520,403, filed on Nov. 13, 2003, provisional application No. 60/518,154, filed on Nov. 6, 2003.

(51) Int. Cl.
*A61K 38/08* (2006.01)

(52) U.S. Cl. .......................................................... 514/2

(58) Field of Classification Search ....................... None
See application file for complete search history.

(56) References Cited

U.S. PATENT DOCUMENTS

| | | | | |
|---|---|---|---|---|
| 3,755,560 | A | 8/1973 | Dickert et al. | 424/78 |
| 3,929,678 | A | 12/1975 | Laughlin et al. | 252/526 |
| 4,152,416 | A | 5/1979 | Spitzer et al. | 424/46 |
| 4,421,769 | A | 12/1983 | Dixon et al. | 424/358 |
| 4,683,195 | A | 7/1987 | Mullis et al. | 435/6 |
| 4,683,202 | A | 7/1987 | Mullis | 435/91 |
| 4,937,370 | A | 6/1990 | Sabatelli | 560/45 |
| 4,965,188 | A | 10/1990 | Mullis et al. | 435/6 |
| 4,999,186 | A | 3/1991 | Sabatelli et al. | 424/60 |
| 5,011,681 | A | 4/1991 | Ciotti et al. | 424/81 |
| 5,073,371 | A | 12/1991 | Turner et al. | 424/401 |
| 5,073,372 | A | 12/1991 | Turner et al. | 424/401 |
| 5,087,372 | A | 2/1992 | Toyomoto et al. | 210/651 |
| 5,322,770 | A | 6/1994 | Gelfand | 435/6 |
| 5,827,508 | A | 10/1998 | Tanner et al. | 424/59 |
| 5,935,556 | A | 8/1999 | Tanner et al. | 424/59 |
| 5,968,485 | A | 10/1999 | Robinson | 424/59 |
| 5,972,316 | A | 10/1999 | Robinson | 424/59 |
| 6,417,327 | B1 * | 7/2002 | Oka et al. | 530/326 |
| 2002/0001825 | A1 | 1/2002 | Itoh | 435/69.4 |
| 2004/0031072 | A1 * | 2/2004 | La Rosa et al. | 800/278 |
| 2004/0034888 | A1 * | 2/2004 | Liu et al. | 800/289 |
| 2004/0123343 | A1 * | 6/2004 | La Rosa et al. | 800/278 |

FOREIGN PATENT DOCUMENTS

| | | | |
|---|---|---|---|
| WO | WO 96/03964 | | 2/1996 |
| WO | WO 96/16636 | | 6/1996 |
| WO | WO 97/38708 | A | 10/1997 |
| WO | WO 98/22085 | | 5/1998 |
| WO | WO 00/06110 | | 2/2000 |
| WO | WO 00/24372 | | 5/2000 |
| WO | WO02094867 | * | 11/2002 |

OTHER PUBLICATIONS

Suzuki et al. "Dual-Mode Regulation of Hair Growth Cycle by Two Fgf-5 Gene Products," J. Invest. Derm. 2000, 114, 456-63.*

Ito et al. "Decapeptide with fibroblast growth factor (FGF)-5 partial sequence inhibits hair growth suppressing activity of FGF-5," J. Cell. Phys. 2003, 197, 272-83.*

Terao et al. "Purification of the aldehyde oxidase homolog 1 (AOH1) protein and cloning of the AOH1 and aldehyde oxidase homolog 2 (AOH2) genes: identification of a novel molybdo-flavoprotein gene cluster on mouse chromosome," J. Biol. Chem., 2001, 276, 46347-63.*

Young et al. "Sequence, localization and function of the invasin protein of Yersinia enterocolitica," Mol. Microbiol., 1990. 4, 1119-28.*

Kaneko et al. "Complete genomic sequence of nitrogen-fixing symbiotic bacterium Bradyrhizobium japonicum USDA110," DNA Res., 2002, 9, 189-97.*

Nakamura et al. "Complete genome structure of the thermophilic cyanobacterium Thermosynechococcus elongatus BP-1," DNA Res., 2002, 9, 123-30.*

Albrecht "Primary structure of the herpesvirus Ateles genome," J. Virol., 2000, 74, 1033-7.*

CAPLUS abstract accession No. 1991:157829.*

CAPLUS abstract accession No. 2002:906291.*

CAPLUS abstract accession No. 2004:663852.*

CAPLUS abstract accession No. 2004:260860.*

CAPLUS abstract accession No. 2004:155818.*

CAPLUS abstract accession No. 2003:130926.*

CAPLUS abstract accession No. 2002:700127.*

CAPLUS abstract accession No. 2000:42494.*

Altschul et al., "Basic Local Alignment Search Tool," *J. Mol. Biol.*, 215:403-410 (1990).

(Continued)

*Primary Examiner*—Cecilia J. Tsang
*Assistant Examiner*—Christina M. Bradley
(74) *Attorney, Agent, or Firm*—Elena E. Quertermous

(57) ABSTRACT

The present invention provides peptides and supported peptides that bind to FGF-5.

18 Claims, 20 Drawing Sheets

OTHER PUBLICATIONS

Beaucage et al., "Deoxynucleoside Phosphoramidites—A New Class of Key Intermediates for Deoxypolynucleotide Synthesis," *Tetrahedron Letters*, 22(20):1859-1862 (1981).

Bode et al., "Natural Protein Proteinase Inhibitors and Their Interaction with Proteinases," *Eurl. J. Biochem.*, 204:433-451 (1992).

Chen et al., "Reactive Sites of an Anticarcinogenic Bowman-Birk Proteinase Inhibitor are Similar to Other Trypsin Inhibitors," *The Journal of Biological Chemistry*, 267(3):1990-1994 (1992).

Chou et al., "Non-Selective Inhibition of Transformed Cell Growth by a Protease Inhibitor," *Proc. Nat. Acad. Sci.* USA, 71(5):1748-1752 (1974).

CTFA, International Cosmetic Ingredient Dictionary and Handbook, 10th Edition 2004, vol. 2, pp. 1026-1028 and 1103 (1995).

Devereaux et al., "A Comprehensive Set of Sequence Analysis Programs for the VAX," 12(1):387-395 (1984).

Hebert et al., "FGF5 as a Regulator of the Hair Growth Cycle: Evidence from Targeted and Spontaneous Mutations," *Cell*, 78:1017-1025 (1994).

Henikoff et al., "Amino Acid Substitution Matrices from Protein Blocks," *Proc. Natl. Acad. Sci. USA*, 89:10915-10919 (1992).

Higgins et al., "CLUSTAL: a Package for Performing Multiple Sequence Alignment on a Microcomputer," *Gene*, 73:237-244 (1988).

Ito et al., "Decapeptide with Fibroblast Growth Factor (FGF)-5 Partial Sequence Inhibits Hair Growth Suppressing Activity of FGF-5," *Journal of Cellular Physiology*, 197:272-283 (2003).

Karlin et al., "Applications and Statistics for Multiple High-scoring Segments in Molecular Sequences," *Proc. Natl. Acad. Sci. USA*, 90:5873-5877 (1993).

Laskowski et al., "Protein Inhibitors of Proteinases," *Ann. Rev. Biochem.*, 49:593-626 (1980).

Lin et al., "The 0.25-nm X-ray Structure of the Bowman-Birk-type Inhibitor from Mung Bean in Ternary Complex with Porcine Trypsin," *Eur. J. Biochem.*, 212:549-555 (1993).

Liu, KeShun, *Soybeans Chemistry, Technology, and Utilization*, pp. 32-35, Aspen Publishers, Inc., Gaithersburg, Maryland (1999).

Livingstone et al., "Protein Sequence Alignments: a Strategy for the Hierarchical Analysis of Residue Conservation," *CABIOS*, 9(6):745-756 (1993).

Matthes et al., "Simultaneous Rapid Chemical Synthesis of Over One Hundred Oligonucleotides on a Microscale," *The EMBO Journal*, 3(4):801-805 (1984).

Morinaga et al., "Improvement of Oligonucleotide-Directed Site-Specific Mutagenesis Using Double-Stranded Plasmid DNA," *Biotechnology*, 2:636-639 (1984).

Nelson et al., "A General Method of Site-Specific Mutagenesis Using a Modification of the *Thermus*Aquaticus Polymerase Chain Reaction," *Analytical Biochemistry*, 180:147-151 (1989).

Pearson et al., "Improved Tools for Biological Sequence Comparison," *Proc. Natl. Acad. Sci. USA*, 85:2444-2448 (1988).

Philpott et al., "Human Hair Growth in vitro: a Model for the Study of Hair Follicle Biology," *Journal of Dermatological Science*, 7:S55-S72 (1994).

Sagarin, *Cosmetics, Science and Technology*, 2$^{nd}$ Edition, vol. 1, pp. 32-43 (1972).

Sarkar et al., "The "Megaprimer" Method of Site-Directed Mutagenesis," *BioTechniques*, 8(4):404-407 (1990).

Sayre et al., "Physical Sunscreens," *J. Soc. Cosmet. Chem.*, 41(2):103-109 (1990).

Song et al., "Kunitz-type Soybean Trypsin Inhibitor Revisited: Refined Structure of its Complex with Porcine Trypsin Reveals an Insight into the Interaction Between a Homologous Inhibitor from *Erythrina caffra* and Tissue-type Plasminogen Activator," *J. Mol. Biol.*, 275:347-363 (1998).

Taylor, "The Classification of Amino Acid Conservation," *J. Theor. Biol.*, 119:205-218 (1986).

Tobin et al., "Plasticity and Cytokinetic Dynamics of the Hair Follicle Mesenchyme: Implications for Hair Growth Control," *The Journal of Investigative Dermatology*, 120:895-904 (2003).

Toru, Imamura, Patent Abstracts of Japan, vol. 2000, No. 7, Sep. 29, 2000, and JP 2000 097938 A (Agency of Ind. Science and amp; Technol.; Pola. Chem. Ind. Inc., Apr. 7, 2000 abstract.

Tsunogae et al., "Crystallization of Bowman-Birk Type Protease Inhibitor (Peanut) and its Complex with Trypsin," *J. Biochem.*, 100:243-246 (1986).

Voss et al., "Crystal Structure of the Bifunctional Soybean Bowman-Birk Inhibitor at 0.28-nm Resolution. Structural Peculiarities in a Folded Protein Conformation," *Eur. J. Biochem.*, 242:122-131 (1996).

Werner et al., "Three-Dimensional Structure of Soybean Trypsin/Chymotrypsin Bowman-Birk Inhibitor in Solution," *Biochemistry*, 31(4):999-1010 (1992).

Yavelow et al., "Bowman-Birk Soybean Protease Inhibitor as an Anticarcinogen," *Cancer Research*, 43:2454s-2459s (1983).

Yavelow et al., "Nanomolar Concentrations of Bowman-Birk Soybean Protease Inhibitor Suppress X-Ray-Induced Transformation in vitro," *Proc. Natl. Acad. Sci. USA*, 82:5395-5399 (1985).

* cited by examiner

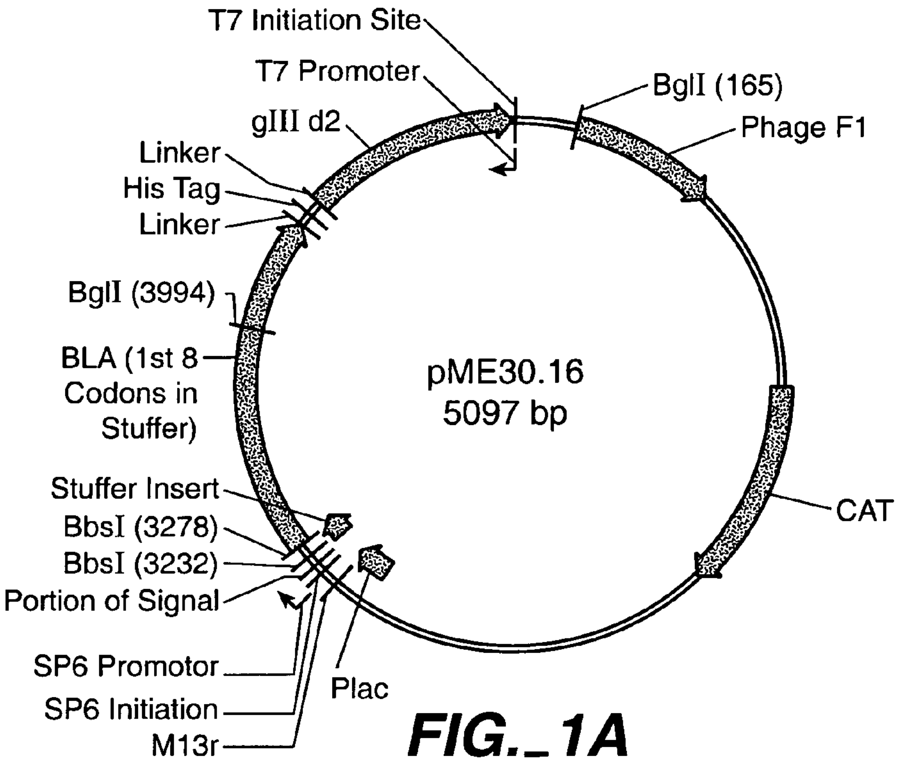
*FIG._1A*
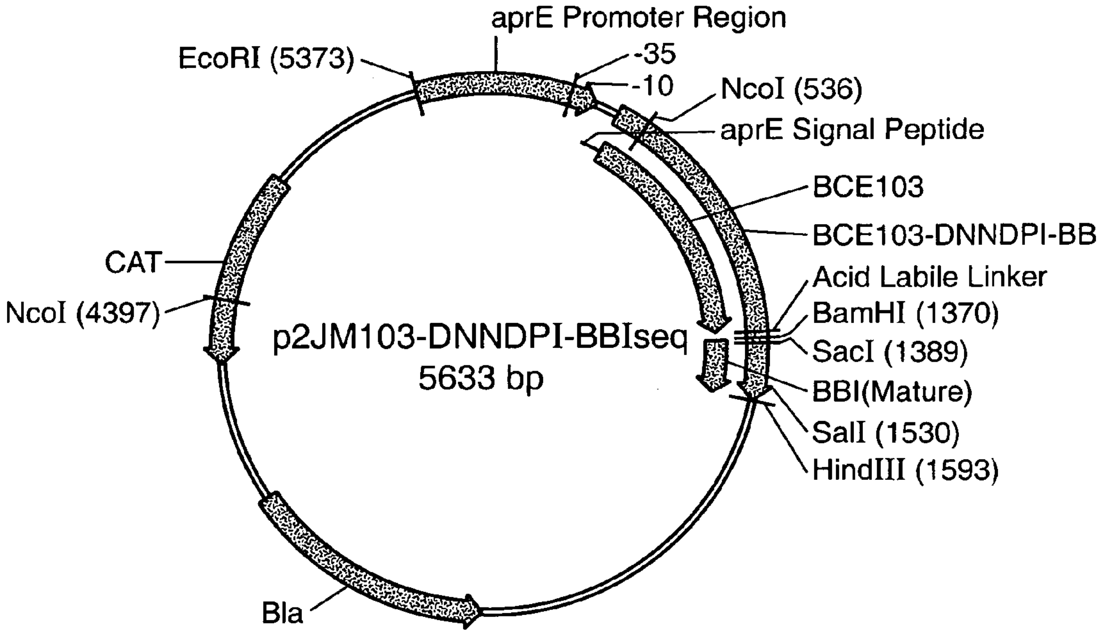
*FIG._1B*

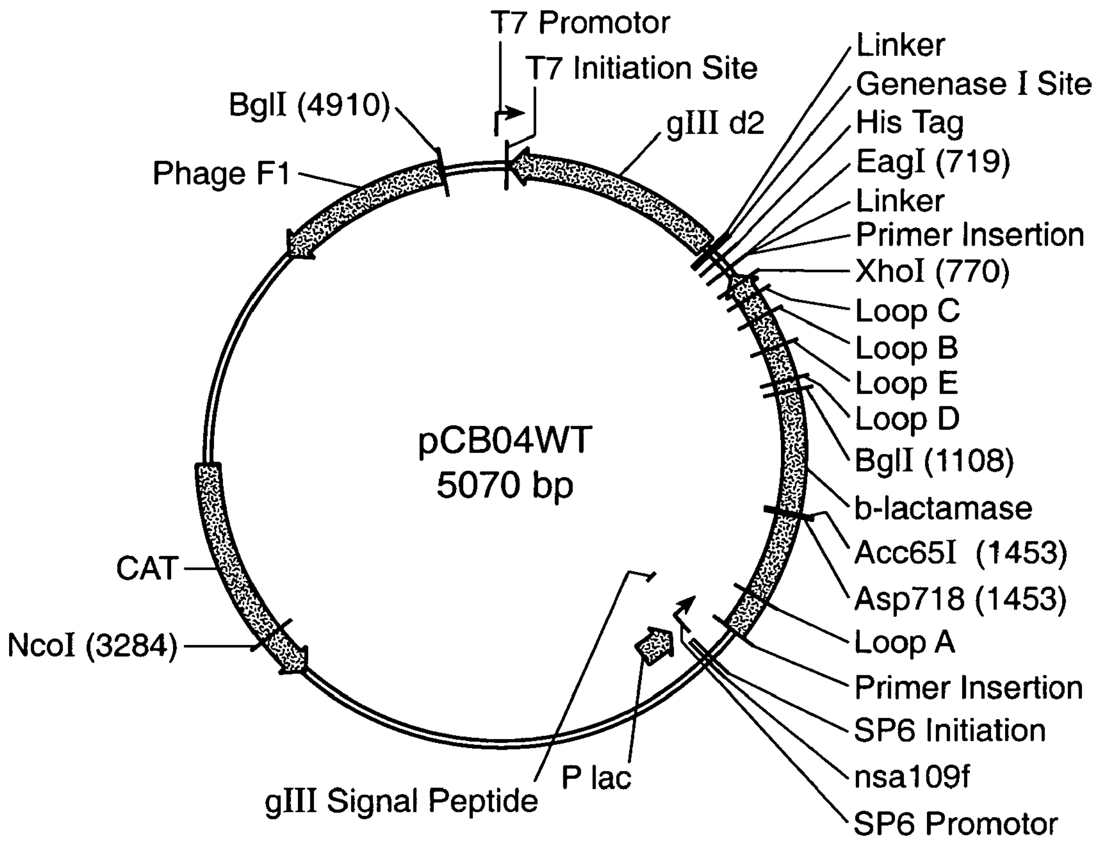
FIG._1C

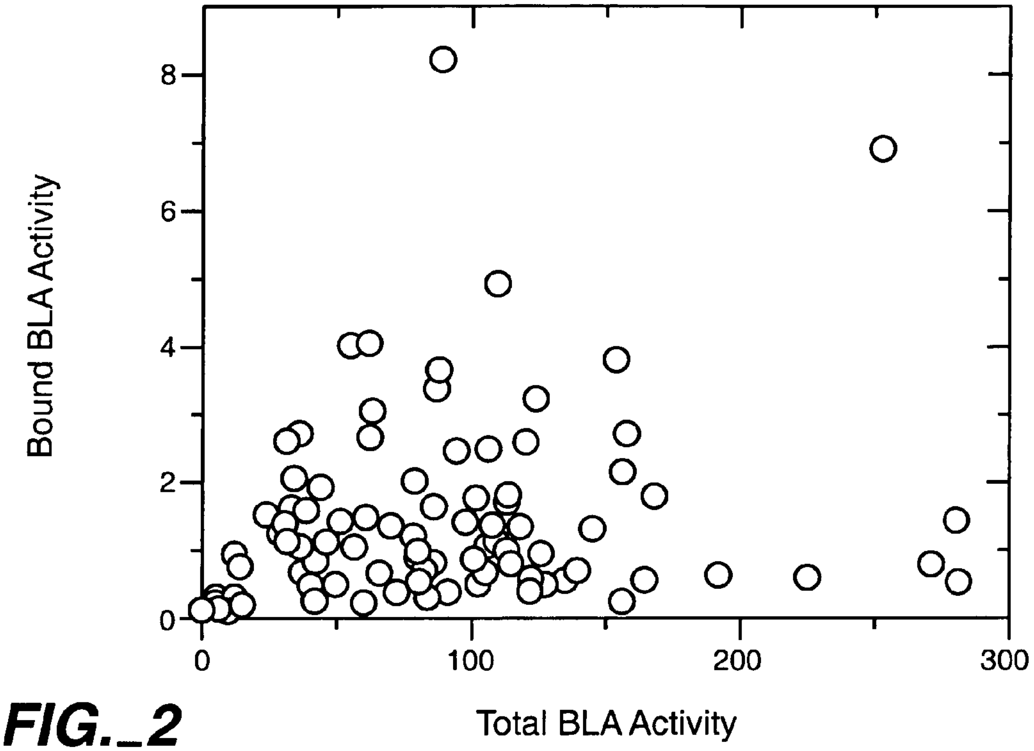
FIG._2
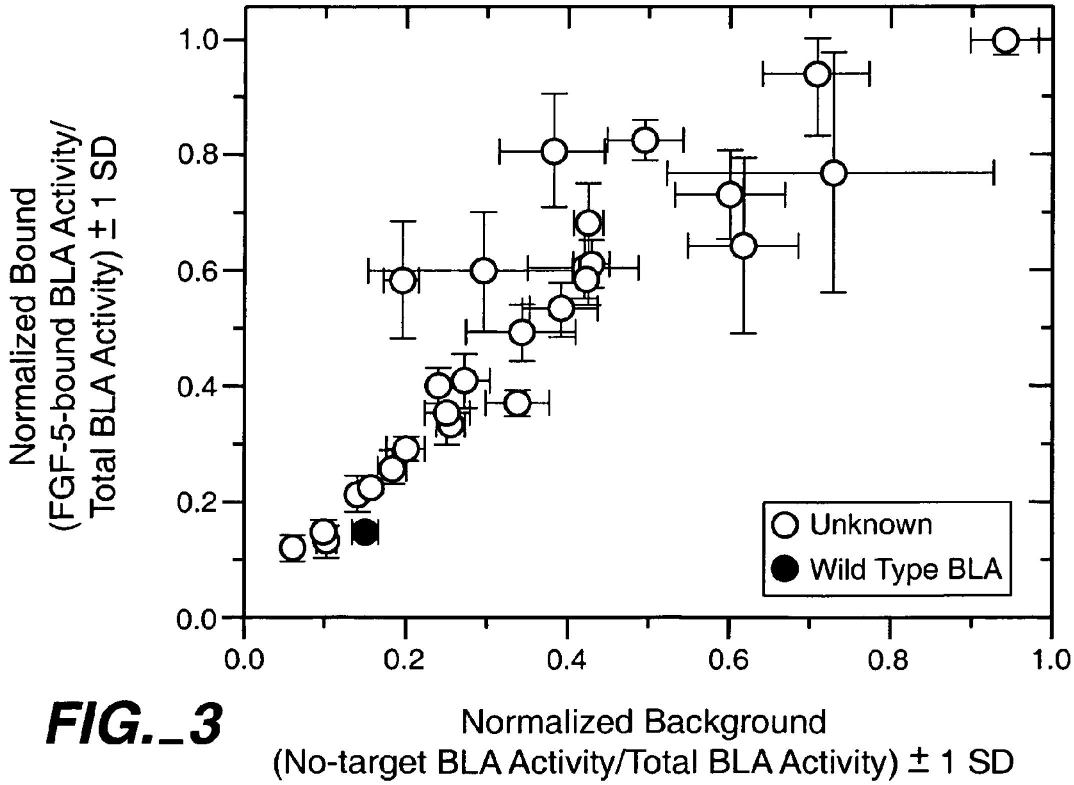
FIG._3

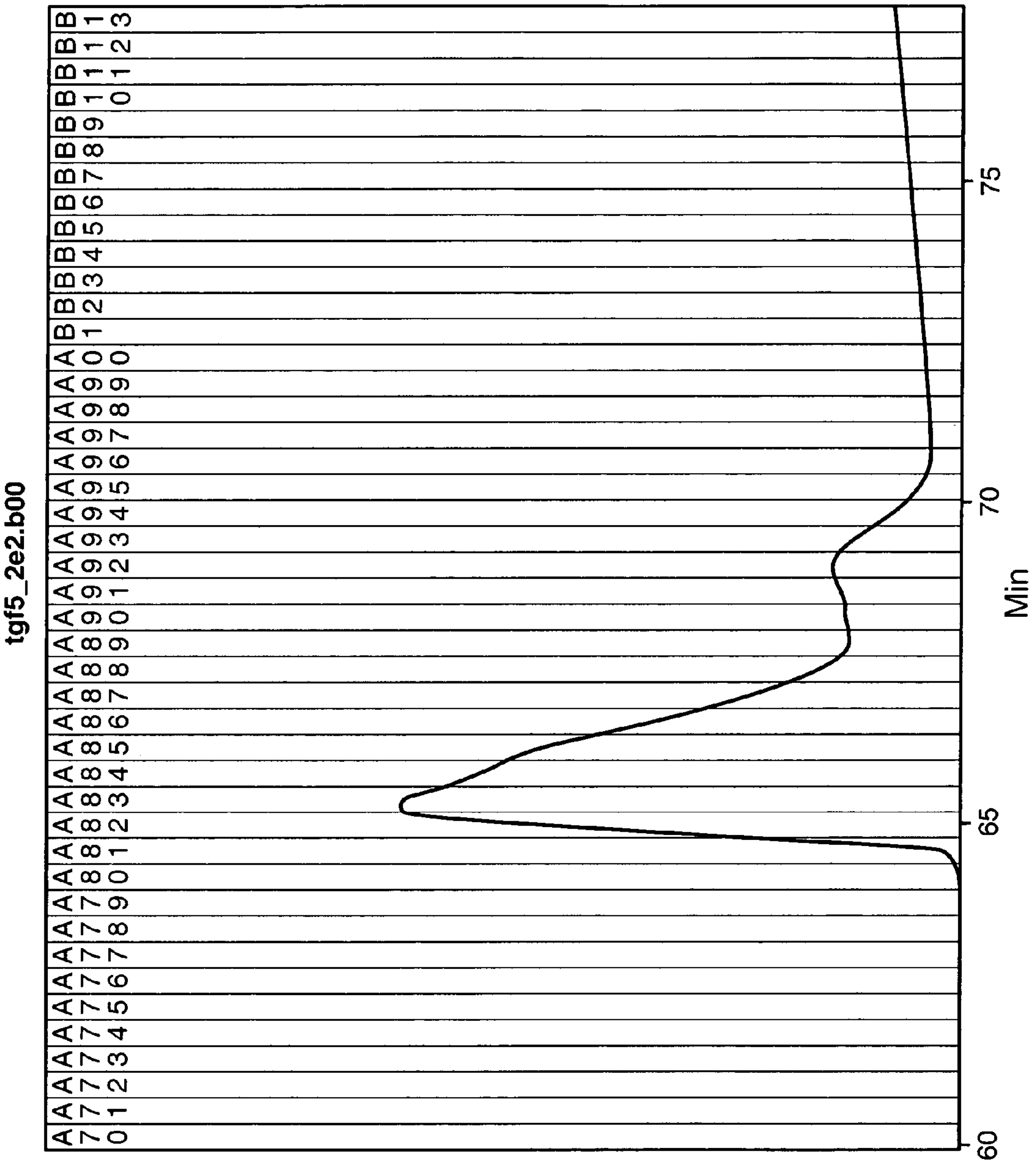
FIG._4

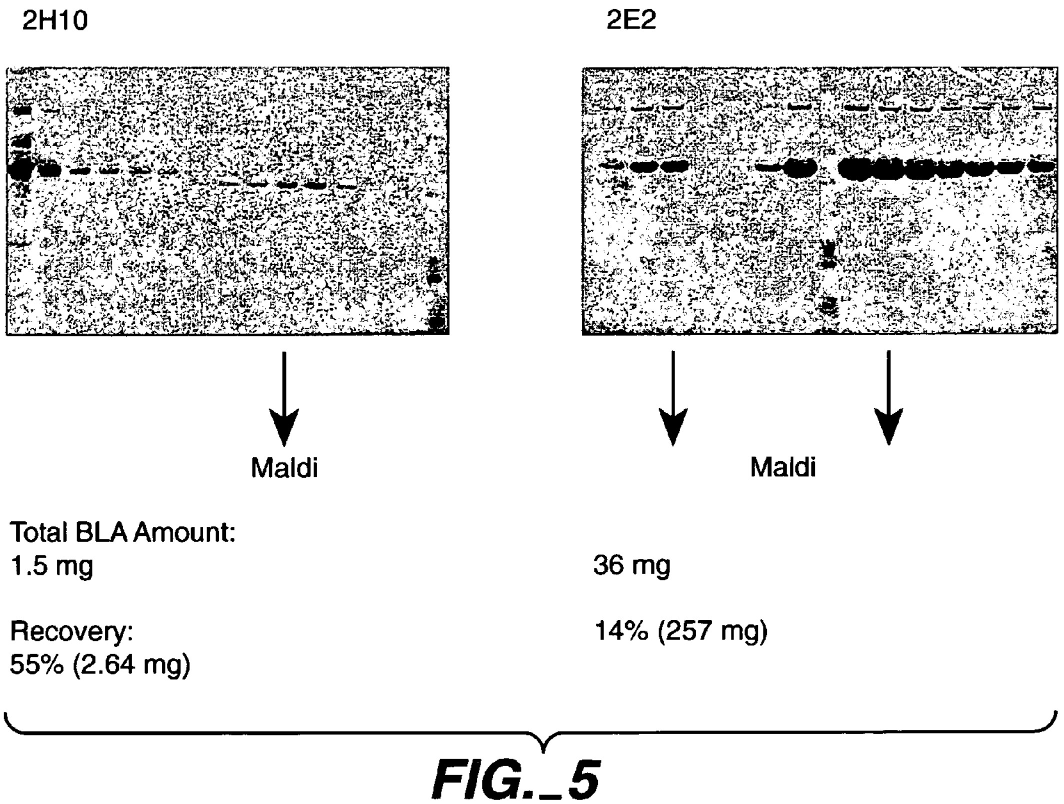
FIG._5

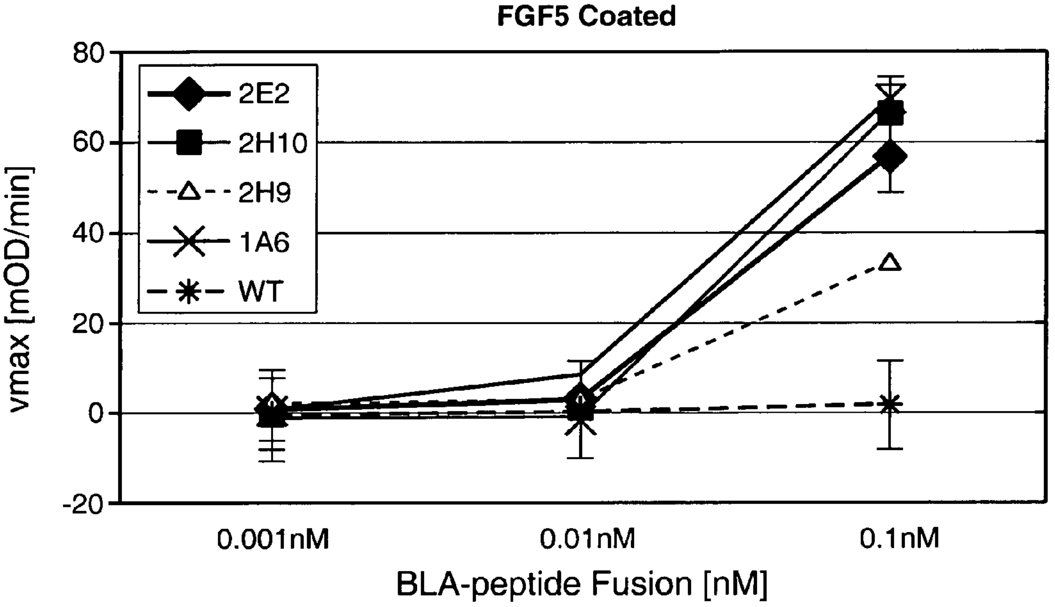
FIG._6A
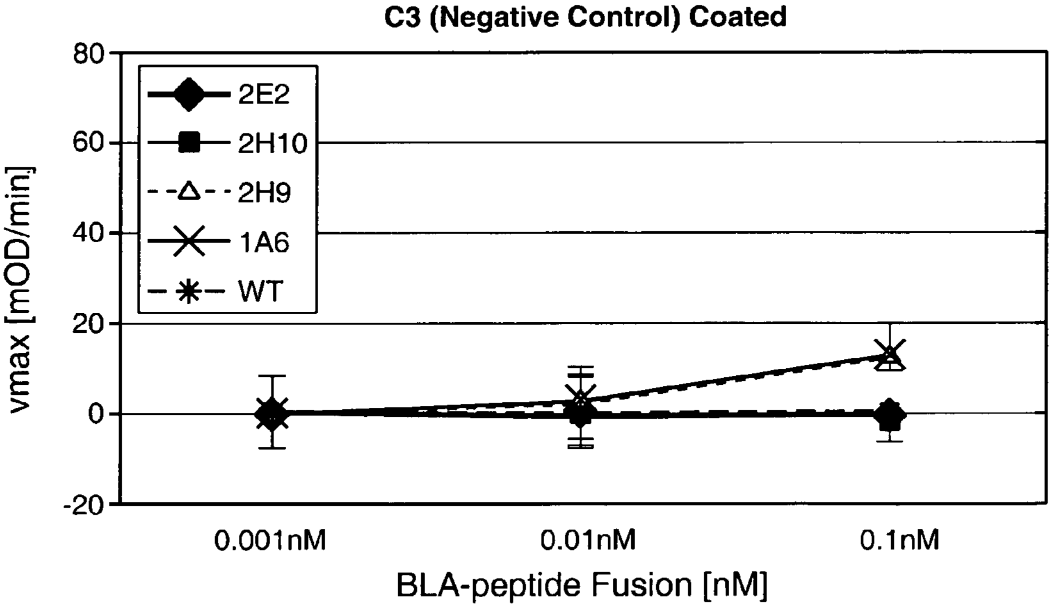
FIG._6B

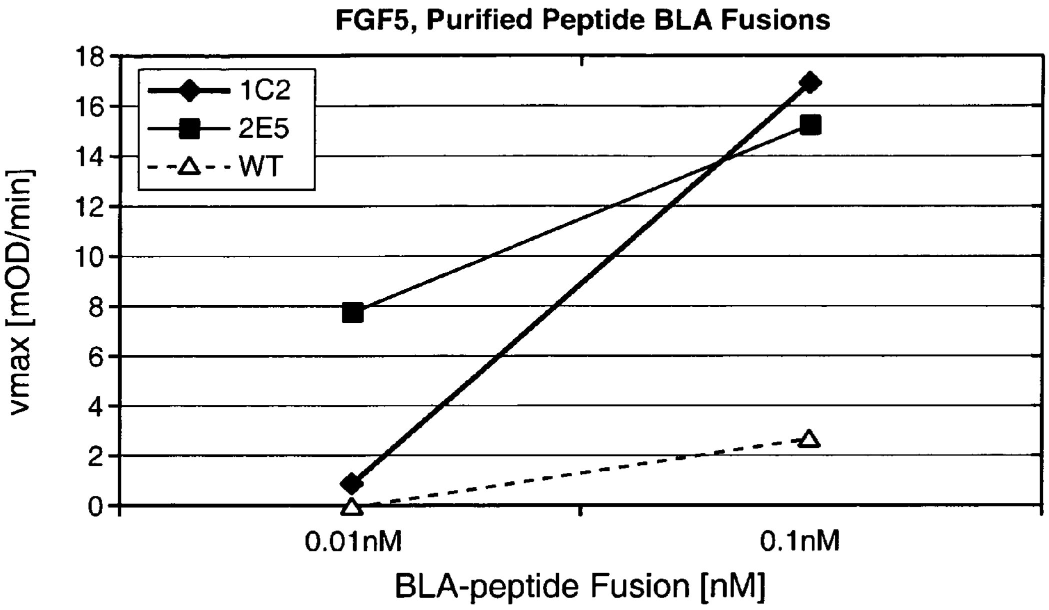
FIG._6C
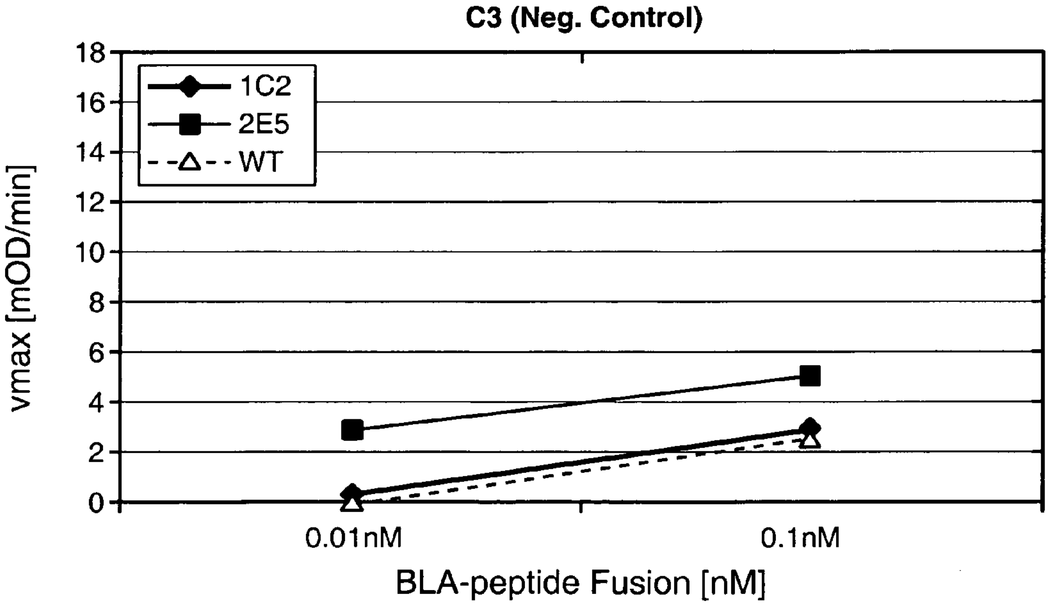
FIG._6D

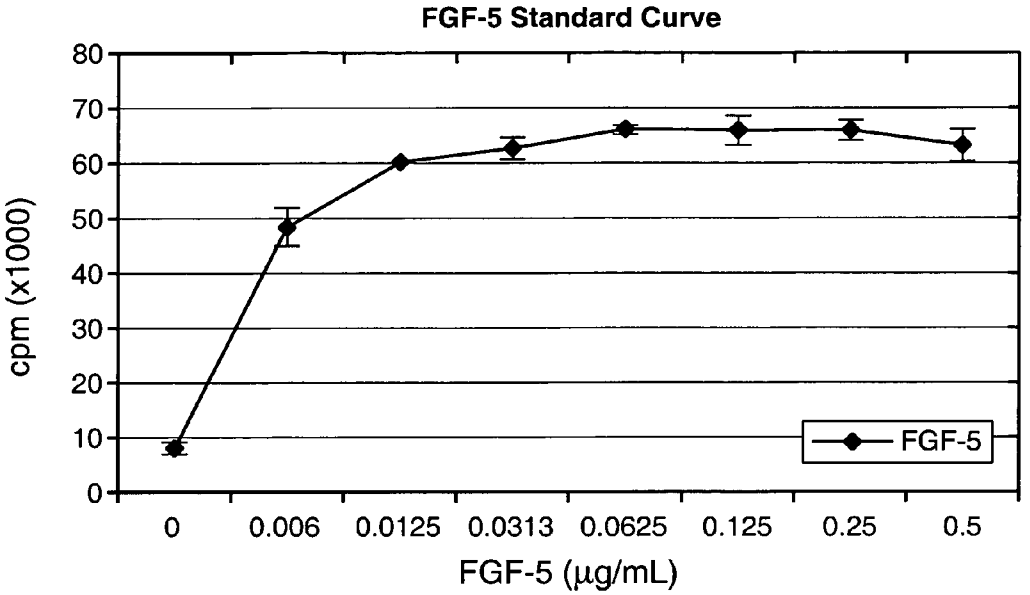
*FIG._7A*
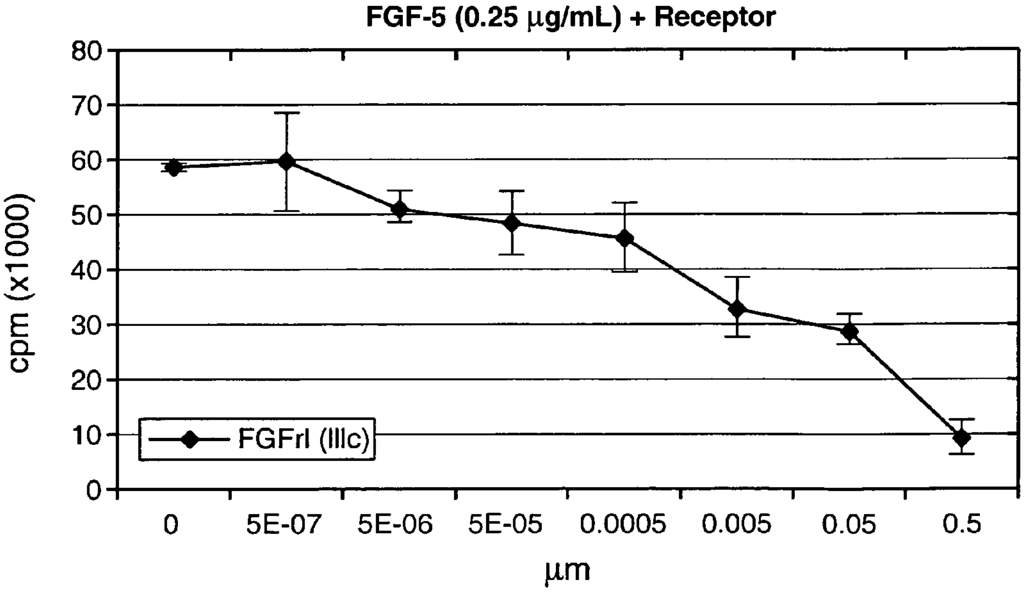
*FIG._7B*

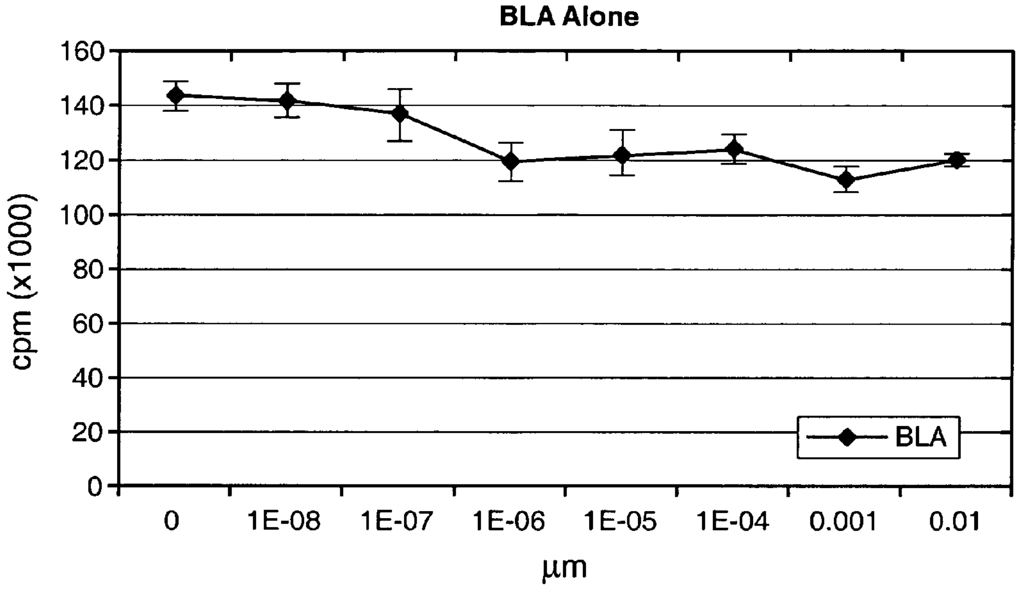
FIG._7C
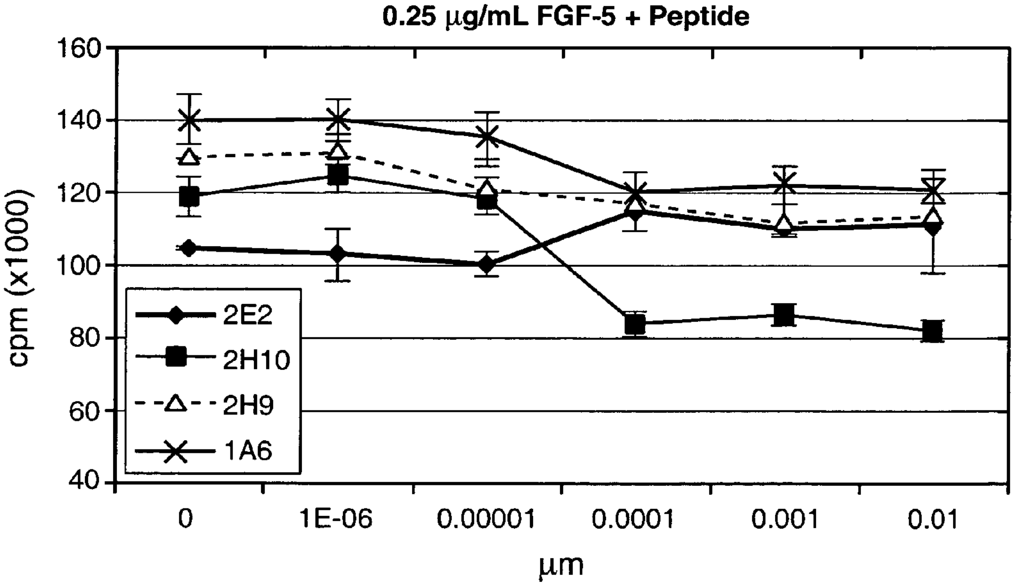
FIG._7D

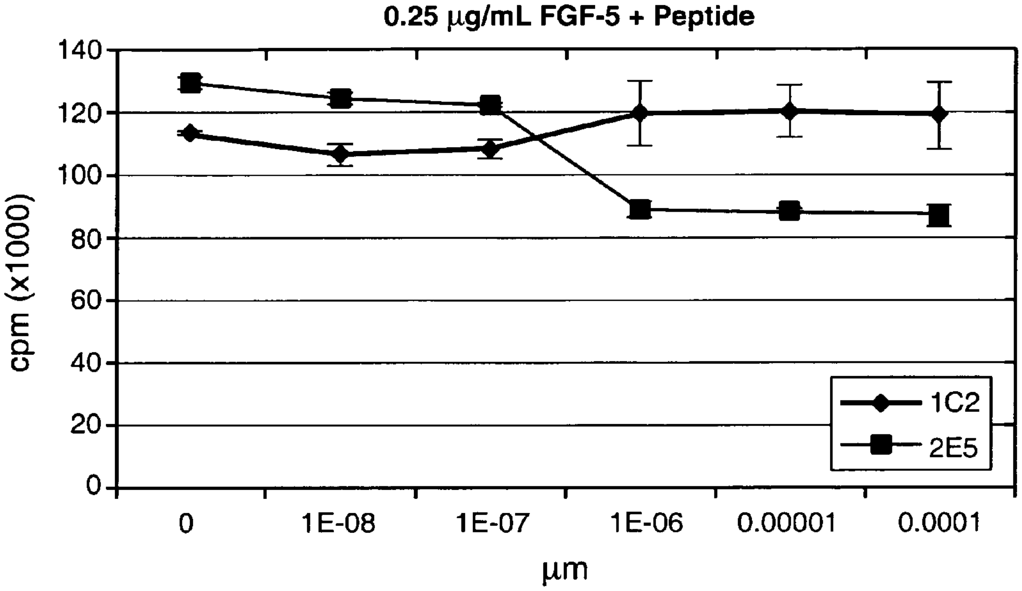
*FIG._7E*
BBI Amino Acid Sequence (SEQ ID NO: 44)
```
DDESSKPCCD QCACTKSNPP QCRCSDMRLN SCHSACKSCI CALSYPAQCF   50
CVDITDFCYE PCKPSEDDKE N                                  71
```
*FIG._8*

1A6 in the Trypsin Inhibitory Loop:

gatgattattcagttgtagaggaacatgggcaactaagtattagtaacggtgaattagtcaatgaacgaggcgaacaagttcagttaaaagggatga
gttcccatggtttgcaatggtacggtcaatttgtaaactatgaaagcatgaaatggctaagagatgattggggaataactgtattccgagcagcaatgta
tacctcttcaggaggatatattgacgatccatcagtaaaggaaaaagtaaaagagactgttgaggctgcgatagaccttggcatatatgtgatcattga
ttggcatatcctttcagacaatgacccgaatatatataaagaagaagcgaaggatttctttgatgaaatgtcagagttgtatggagactatccgaatgtg
atatacgaaattgcaaatgaaccgaatggtagtgatgttacgtgggacaatcaaataaaaccgtatgcagaagaagtgattccggttattcgtgacaa
tgaccctaataacattgttattgtaggtacaggtacatggagtcaggatgtccatcatgcagccgataatcagcttgcagatcctaacgtcatgtatgcat
ttcattttatgcaggaacacatggacaaaatttacgagaccaagtagattatgcattagatcaaggagcagcgatatttgttagtgaatgggggacaa
gtgcagctacaggtgatggtggtgtttttagatgaagcacaagtgtggattgactttatggatgaaagaaatttaagctgggccaactggtctctaac
gcataaggatgagtcatctgcagcgttaatgccaggtgcaaatccaactggtggttggacagaggctgaactatctccatctggtacatttgtgaggg
aaaaaataagagaatcagcatctgacaacaatgatcccataccggatccagacgatgagagctctaaaccctgttgcgatcaatgcgcatgtgaa
gagatctggactatgctttgccggtgttccgatatgcgtctgaatagctgtcatagtgcatgcaaaagctgtatctgcgccctgagttatccagctcaatgt
ttttgcgtcgacatcacggacttctgctatgagccatgtaaaccaagcgaggacgataaagagaac (SEQ. ID NO: 85)

DDYSVVEEHGQLSISNGELVNERGEQVQLKGMSSHGLQWYGQFVNYESMKWLRDDWGITVFRAAMYTSSGGYIDDPSVKE
KVKETVEAAIDLGIYVIIDWHILSDNDPNIYKEEAKDFFDEMSELYGDYPNVIYEIANEPNGSDVTWDNQIKPYAEEVIP
VIRDNDPNNIVIVGTGTWSQDVHHAADNQLADPNVMYAFHFYAGTHGQNLRDQVDYALDQGAAIFVSEWGTSAATGDGGV
FLDEAQVWIDFMDERNLSWANWSLTHKDESSAALMPGANPTGGWTEAELSPSGTFVREKIRESASDNNDPIPDPDDESSK
PCCDQCACEEIWTMLCRCSDMRLNSCHSACKSCICALSYPAQCFCVDITDFCYEPCKPSEDDKEN (SEQ. ID NO: 86)

FIG._9A

1C2 in the Trypsin Inhibitory Loop:

gatgattattcagttgtagaggaacatgggcaactaagtattagtaacggtgaattagtcaatgaacgaggcgaacaagttcagttaaaagggatga
gttcccatggtttgcaatggtacggtcaatttgtaaactatgaaagcatgaaatggctaagagatgattggggaataactgtattccgagcagcaatgta
tacctcttcaggaggatatattgacgatccatcagtaaaggaaaaagtaaaagagactgttgaggctgcgatagaccttggcatatatgtgatcattga
ttggcatatcctttcagacaatgacccgaatatatataaagaagaagcgaaggatttctttgatgaaatgtcagagttgtatggagactatccgaatgtg
atatacgaaattgcaaatgaaccgaatggtagtgatgttacgtgggacaatcaaataaaaccgtatgcagaagaagtgattccggttattcgtgacaa
tgaccctaataacattgttattgtaggtacaggtacatggagtcaggatgtccatcatgcagccgataatcagcttgcagatcctaacgtcatgtatgcat
ttcatttttatgcaggaacacatggacaaaatttacgagaccaagtagattatgcattagatcaaggagcagcgatatttgttagtgaatgggggacaa
gtgcagctacaggtgatggtggtgtgtttttagatgaagcacaagtgtggattgactttatggatgaaagaaatttaagctgggccaactggtctctaac
gcataaggatgagtcatctgcagcgttaatgccaggtgcaaatccaactggtggttggacagaggctgaactatctccatctggtacatttgtgaggg
aaaaaataagagaatcagcatctgacaacaatgatcccataccggatccagacgatgagagctctaaaccctgttgcgatcaatgcgcatgttggg
cccttactgtcaaaacatgccggtgttccgatatgcgtctgaatagctgtcatagtgcatgcaaaagctgtatctgcgccctgagttatccagctcaatgtt
tttgcgtcgacatcacggacttctgctatgagccatgtaaaccaagcgaggacgataaagagaac (SEQ. ID NO: 87)

DDYSVVEEHGQLSISNGELVNERGEQVQLKGMSSHGLQWYGQFVNYESMKWLRDDWGITVFRAAMYTSSGGYIDDPSVKE
KVKETVEAAIDLGIYVIIDWHILSDNDPNIYKEEAKDFFDEMSELYGDYPNVIYEIANEPNGSDVTWDNQIKPYAEEVIP
VIRDNDPNNIVIVGTGTWSQDVHHAADNQLADPNVMYAFHFYAGTHGQNLRDQVDYALDQGAAIFVSEWGTSAATGDGGV
FLDEAQVWIDFMDERNLSWANWSLTHKDESSAALMPGANPTGGWTEAELSPSGTFVREKIRESASDNNDPIPDPDDESSK
PCCDQCACWALTVKTCRCSDMRLNSCHSACKSCICALSYPAQCFCVDITDFCYEPCKPSEDDKEN (SEQ. ID NO: 88)

FIG._9B

2E2 in the Trypsin Inhibitory Loop:

gatgattattcagttgtagaggaacatgggcaactaagtattagtaacggtgaattagtcaatgaacgaggcgaacaagttcagttaaaagggatga
gttcccatggtttgcaatggtacggtcaatttgtaaactatgaaagcatgaaatggctaagagatgattggggaataactgtattccgagcagcaatgta
tacctcttcaggaggatatattgacgatccatcagtaaaggaaaaagtaaaagagactgttgaggctgcgatagaccttggcatatatgtgatcattga
ttggcatatcctttcagacaatgacccgaatatatataaagaagaagcgaaggatttctttgatgaaatgtcagagttgtatggagactatccgaatgtg
atatacgaaattgcaaatgaaccgaatggtagtgatgttacgtgggacaatcaaataaaaccgtatgcagaagaagtgattccggttattcgtgacaa
tgaccctaataacattgttattgtaggtacaggtacatggagtcaggatgtccatcatgcagccgataatcagcttgcagatcctaacgtcatgtatgcat
ttcatttttatgcaggaacacatggacaaaatttacgagaccaagtagattatgcattagatcaaggagcagcgatatttgttagtgaatgggggacaa
gtgcagctacaggtgatggtggtgtttttagatgaagcacaagtgtggattgactttatggatgaaagaaatttaagctgggccaactggtctctaac
gcataaggatgagtcatctgcagcgttaatgccaggtgcaaatccaactggtggttggacagaggctgaactatctccatctggtacatttgtgaggg
aaaaaataagagaatcagcatctgacaacaatgatcccataccggatccagacgatgagagctctaaaccctgttgcgatcaatgcgcatgtctta
cagtactgtggactacatgccggtgttccgatatgcgtctgaatagctgtcatagtgcatgcaaaagctgtatctgcgccctgagttatccagctcaatgt
tttgcgtcgacatcacggacttctgctatgagccatgtaaaccaagcgaggacgataaagagaac (SEQ ID NO: 89)

DDYSVVEEHGQLSISNGELVNERGEQVQLKGMSSHGLQWYGQFVNYESMKWLRDDWGITVFRAAMYTSSGGYIDDPSVKE
KVKETVEAAIDLGIYVIIDWHILSDNDPNIYKEEAKDFFDEMSELYGDYPNVIYEIANEPNGSDVTWDNQIKPYAEEVIP
VIRDNDPNNIVIVGTGTWSQDVHHAADNQLADPNVMYAFHFYAGTHGQNLRDQVDYALDQGAAIFVSEWGTSAATGDGGV
FLDEAQVWIDFMDERNLSWANWSLTHKDESSAALMPGANPTGGWTEAELSPSGTFVREKIRESASDNNDPIPDPDDESSK
PCCDQCACLTVLWTTCRCSDMRLNSCHSACKSCICALSYPAQCFCVDITDFCYEPCKPSEDDKEN (SEQ ID NO: 90)

FIG._9C

2E5 in the Trypsin Inhibitory Loop:

gatgattattcagttgtagaggaacatgggcaactaagtattagtaacggtgaattagtcaatgaacgaggcgaacaagttcagttaaaagggatga
gttcccatggtttgcaatggtacggtcaatttgtaaactatgaaagcatgaaatggctaagagatgattggggaataactgtattccgagcagcaatgta
tacctcttcaggaggatatattgacgatccatcagtaaaggaaaaagtaaaagagactgttgaggctgcgatagaccttggcatatatgtgatcattga
ttggcatatcctttcagacaatgacccgaatatatataaagaagaagcgaaggatttctttgatgaaatgtcagagttgtatggagactatccgaatgtg
atatacgaaattgcaaatgaaccgaatggtagtgatgttacgtgggacaatcaaataaaaccgtatgcagaagaagtgattccggttattcgtgacaa
tgaccctaataacattgttattgtaggtacaggtacatggagtcaggatgtccatcatgcagccgataatcagcttgcagatcctaacgtcatgtatgcat
ttcattttatgcaggaacacatggacaaaatttacgagaccaagtagattatgcattagatcaaggagcagcgatatttgttagtgaatggggacaa
gtgcagctacaggtgatggtggtgtgtttttagatgaagcacaagtgtggattgactttatggatgaaagaaatttaagctgggccaactggtctctaac
gcataaggatgagtcatctgcagcgttaatgccaggtgcaaatccaactggtggttggacagaggctgaactatctccatctggtacatttgtgaggg
aaaaaataagagaatcagcatctgacaacaatgatcccataccggatccagacgatgagagctctaaaccctgttgcgatcaatgcgcatgtactc
tttggaacagatctccttgccggtgttccgatatgcgtctgaatagctgtcatagtgcatgcaaaagctgtatctgcgccctgagttatccagctcaatgttt
ttgcgtcgacatcacggacttctgctatgagccatgtaaaccaagcgaggacgataaagagaac (SEQ ID NO: 91)

DDYSVVEEHGQLSISNGELVNERGEQVQLKGMSSHGLQWYGQFVNYESMKWLRDDWGITVFRAAMYTSSGGYIDDPSVKE
KVKETVEAAIDLGIYVIIDWHILSDNDPNIYKEEAKDFFDEMSELYGDYPNVIYEIANEPNGSDVTWDNQIKPYAEEVIP
VIRDNDPNNIVIVGTGTWSQDVHHAADNQLADPNVMYAFHFYAGTHGQNLRDQVDYALDQGAAIFVSEWGTSAATGDGGV
FLDEAQVWIDFMDERNLSWANWSLTHKDESSAALMPGANPTGGWTEAELSPSGTFVREKIRESASDNNDPIPDPDDESSK
PCCDQCACTLWNRSPCRCSDMRLNSCHSACKSCICALSYPAQCFCVDITDFCYEPCKPSEDDKEN (SEQ ID NO: 92)

FIG._9D

1A6 in the Chymotrypsin Inhibitory Loop:

gatgattattcagttgtagaggaacatgggcaactaagtattagtaacggtgaattagtcaatgaacgaggcgaacaagttcagttaaaagggatga
gttcccatggtttgcaatggtacggtcaatttgtaaactatgaaagcatgaaatggctaagagatgattggggaataactgtattccgagcagcaatgta
tacctcttcaggaggatatattgacgatccatcagtaaaggaaaaagtaaaagagactgttgaggctgcgatagaccttggcatatatgtgatcattga
ttggcatatcctttcagacaatgacccgaatatatataaagaagaagcgaaggatttctttgatgaaatgtcagagttgtatggagactatccgaatgtg
atatacgaaattgcaaatgaaccgaatggtagtgatgttacgtgggacaatcaaataaaaccgtatgcagaagaagtgattccggttattcgtgacaa
tgaccctaataacattgttattgtaggtacaggtacatggagtcaggatgtccatcatgcagccgataatcagcttgcagatcctaacgtcatgtatgcat
ttcattttatgcaggaacacatggacaaaatttacgagaccaagtagattatgcattagatcaaggagcagcgatatttgttagtgaatgggggacaa
gtgcagctacaggtgatggtggtgtttttagatgaagcacaagtgtggattgactttatggatgaaagaaatttaagctgggccaactggtctctaac
gcataaggatgagtcatctgcagcgttaatgccaggtgcaaatccaactggtggttggacagaggctgaactatctccatctggtacatttgtgaggg
aaaaaataagagaatcagcatctgacaacaatgatcccataccggatccagacgatgagagctctaaaccctgttgcgatcaatgcgcatgtacg
aaatcaaatcctccacagtgtcggtgttccgatatgcgtctgaatagctgtcatagtgcatgcaaaagctgtgcttgtgaagagatctggactatgctttg
cttttgcgtcgacatcacggacttctgctatgagccatgtaaaccaagcgaggacgataaagagaac (SEQ ID NO: 93)

DDYSVVEEHGQLSISNGELVNERGEQVQLKGMSSHGLQWYGQFVNYESMKWLRDDWGITVFRAAMYTSSGGYIDDPSVKE
KVKETVEAAIDLGIYVIIDWHILSDNDPNIYKEEAKDFFDEMSELYGDYPNVIYEIANEPNGSDVTWDNQIKPYAEEVIP
VIRDNDPNNIVIVGTGTWSQDVHHAADNQLADPNVMYAFHFYAGTHGQNLRDQVDYALDQGAAIFVSEWGTSAATGDGGV
FLDEAQVWIDFMDERNLSWANWSLTHKDESSAALMPGANPTGGWTEAELSPSGTFVREKIRESASDNNDPIPDPDDESSK
PCCDQCACTKSNPPQCRCSDMRLNSCHSACKSCACEEIWTMLCFCVDITDFCYEPCKPSEDDKEN (SEQ ID NO: 94)

FIG._9E

1C2 in the Chymotrypsin Inhibitory Loop:

gatgattattcagttgtagaggaacatgggcaactaagtattagtaacggtgaattagtcaatgaacgaggcgaacaagttcagttaaaagggatga
gttcccatggtttgcaatggtacggtcaatttgtaaactatgaaagcatgaaatggctaagagatgattggggaataactgtattccgagcagcaatgta
tacctcttcaggaggatatattgacgatccatcagtaaaggaaaaagtaaaagagactgttgaggctgcgatagaccttggcatatatgtgatcattga
ttggcatatcctttcagacaatgacccgaatatatataaagaagaagcgaaggatttctttgatgaaatgtcagagttgtatggagactatccgaatgtg
atatacgaaattgcaaatgaaccgaatggtagtgatgttacgtgggacaatcaaataaaaccgtatgcagaagaagtgattccggttattcgtgacaa
tgaccctaataacattgttattgtaggtacaggtacatggagtcaggatgtccatcatgcagccgataatcagcttgcagatcctaacgtcatgtatgcat
ttcattttatgcaggaacacatggacaaaatttacgagaccaagtagattatgcattagatcaaggagcagcgatatttgttagtgaatggggacaa
gtgcagctacaggtgatggtggtgtgtttttagatgaagcacaagtgtggattgactttatggatgaaagaaatttaagctgggccaactggtctctaac
gcataaggatgagtcatctgcagcgttaatgccaggtgcaaatccaactggtggttggacagaggctgaactatctccatctggtacatttgtgaggg
aaaaaataagagaatcagcatctgacaacaatgatcccataccggatccagacgatgagagctctaaaccctgttgcgatcaatgcgcatgtacg
aaatcaaatcctccacagtgtcggtgttccgatatgcgtctgaatagctgtcatagtgcatgcaaaagctgtgcttgttgggcccttactgtcaaaacatg
cttttgcgtcgacatcacggacttctgctatgagccatgtaaaccaagcgaggacgataaagagaac (SEQ ID NO: 95)

DDYSVVEEHGQLSISNGELVNERGEQVQLKGMSSHGLQWYGQFVNYESMKWLRDDWGITVFRAAMYTSSGGYIDDPSVKE
KVKETVEAAIDLGIYVIIDWHILSDNDPNIYKEEAKDFFDEMSELYGDYPNVIYEIANEPNGSDVTWDNQIKPYAEEVIP (SEQ ID NO: 96)

VIRDNDPNNIVIVGTGTWSQDVHHAADNQLADPNVMYAFHFYAGTHGQNLRDQVDYALDQGAAIFVSEWGTSAATGDGGV
FLDEAQVWIDFMDERNLSWANWSLTHKDESSAALMPGANPTGGWTEAELSPSGTFVREKIRESASDNNDPIPDPDDESSK
PCCDQCAC<u>TKSNPPQ</u>CRCSDMRLNSCHSACKSCAC<u>WALTVKT</u>CFCVDITDFCYEPCKPSEDDKEN (SEQ ID NO: 96)

FIG._9F

2E2 in the Chymotrypsin Inhibitory Loop:

gatgattattcagttgtagaggaacatgggcaactaagtattagtaacggtgaattagtcaatgaacgaggcgaacaagttcagttaaaagggatga
gttcccatggtttgcaatggtacggtcaatttgtaaactatgaaagcatgaaatggctaagagatgattggggaataactgtattccgagcagcaatgta
tacctcttcaggaggatatattgacgatccatcagtaaaggaaaaagtaaaagagactgttgaggctgcgatagaccttggcatatatgtgatcattga
ttggcatatcctttcagacaatgacccgaatatatataaagaagaagcgaaggatttctttgatgaaatgtcagagttgtatggagactatccgaatgtg
atatacgaaattgcaaatgaaccgaatggtagtgatgttacgtgggacaatcaaataaaaccgtatgcagaagaagtgattccggttattcgtgacaa
tgaccctaataacattgttattgtaggtacaggtacatggagtcaggatgtccatcatgcagccgataatcagcttgcagatcctaacgtcatgtatgcat
ttcatttttatgcaggaacacatggacaaaatttacgagaccaagtagattatgcattagatcaaggagcagcgatatttgttagtgaatgggggacaa
gtgcagctacaggtgatggtggtgtgtttttagatgaagcacaagtgtggattgactttatggatgaaagaaatttaagctgggccaactggtctctaac
gcataaggatgagtcatctgcagcgttaatgccaggtgcaaatccaactggtggttggacagaggctgaactatctccatctggtacatttgtgaggg
aaaaaataagagaatcagcatctgacaacaatgatcccataccggatccagacgatgagagctctaaaccctgttgcgatcaatgcgcatgtacg
aaatcaaatcctccacagtgtcggtgttccgatatgcgtctgaatagctgtcatagtgcatgcaaaagctgtgcttgtcttacagtactgtggactacatg
cttttgcgtcgacatcacggacttctgctatgagccatgtaaaccaagcgaggacgataaagagaac (SEQ ID NO: 98)

DDYSVVEEHGQLSISNGELVNERGEQVQLKGMSSHGLQWYGQFVNYESMKWLRDDWGITVFRAAMYTSSGGYIDDPSVKE
KVKETVEAAIDLGIYVIIDWHILSDNDPNIYKEEAKDFFDEMSELYGDYPNVIYEIANEPNGSDVTWDNQIKPYAEEVIP
VIRDNDPNNIVIVGTGTWSQDVHHAADNQLADPNVMYAFHFYAGTHGQNLRDQVDYALDQGAAIFVSEWGTSAATGDGGV
FLDEAQVWIDFMDERNLSWANWSLTHKDESSAALMPGANPTGGWTEAELSPSGTFVREKIRESASDNNDPIPDPDDESSK
PCCDQCACTKSNPPQCRCSDMRLNSCHSACKSCACLTVLWTTCFCVDITDFCYEPCKPSEDDKEN (SEQ ID NO: 99)

FIG._9G

2E5 in the Chymotrypsin Inhibitory Loop:

gatgattattcagttgtagaggaacatgggcaactaagtattagtaacggtgaattagtcaatgaacgaggcgaacaagttcagttaaaagggatga
gttcccatggtttgcaatggtacggtcaatttgtaaactatgaaagcatgaaatggctaagagatgattggggaataactgtattccgagcagcaatgta
tacctcttcaggaggatatattgacgatccatcagtaaaggaaaaagtaaaagagactgttgaggctgcgatagaccttggcatatatgtgatcattga
ttggcatatcctttcagacaatgacccgaatatatataaagaagaagcgaaggatttctttgatgaaatgtcagagttgtatggagactatccgaatgtg
atatacgaaattgcaaatgaaccgaatggtagtgatgttacgtgggacaatcaaataaaaccgtatgcagaagaagtgattccggttattcgtgacaa
tgaccctaataacattgttattgtaggtacaggtacatggagtcaggatgtccatcatgcagccgataatcagcttgcagatcctaacgtcatgtatgcat
ttcatttttatgcaggaacacatggacaaaatttacgagaccaagtagattatgcattagatcaaggagcagcgatatttgttagtgaatgggggacaa
gtgcagctacaggtgatggtggtgtgtttttagatgaagcacaagtgtggattgactttatggatgaaagaaatttaagctgggccaactggtctctaac
gcataaggatgagtcatctgcagcgttaatgccaggtgcaaatccaactggtggttggacagaggctgaactatctccatctggtacatttgtgaggg
aaaaaataagagaatcagcatctgacaacaatgatcccataccggatccagacgatgagagctctaaaccctgttgcgatcaatgcgcatgtacg
aaatcaaatcctccacagtgtcggtgttccgatatgcgtctgaatagctgtcatagtgcatgcaaaagctgtgcttgtactctttggaatcgatctccttgct
tttgcgtcgacatcacggacttctgctatgagccatgtaaaccaagcgaggacgataaagagaac (SEQ ID NO: 100)

DDYSVVEEHGQLSISNGELVNERGEQVQLKGMSSHGLQWYGQFVNYESMKWLRDDWGITVFRAAMYTSSGGYIDDPSVKE
KVKETVEAAIDLGIYVIIDWHILSDNDPNIYKEEAKDFFDEMSELYGDYPNVIYEIANEPNGSDVTWDNQIKPYAEEVIP
VIRDNDPNNIVIVGTGTWSQDVHHAADNQLADPNVMYAFHFYAGTHGQNLRDQVDYALDQGAAIFVSEWGTSAATGDGGV
FLDEAQVWIDFMDERNLSWANWSLTHKDESSAALMPGANPTGGWTEAELSPSGTFVREKIRESASDNNDPIPDPDDESSK
PCCDQCACTKSNPPQCRCSDMRLNSCHSACKSCACTLWNRSPCFCVDITDFCYEPCKPSEDDKEN (SEQ ID NO: 101)

FIG._9H

Binders to FGF-5 Target

| | Plate | Position | Control Plate (OD490) | Target Plate (OD490) | Target-Control | Peptide Sequence 1 2 3 4 5 6 7 |
|---|---|---|---|---|---|---|
| 15 FGF5-MM-001 | FGF5013 | C04 | 1.454 | 1.638 | 0.184 | |
| 16 FGF5-MM-002 | FGF5013 | H11 | 1.553 | 1.884 | 0.331 | P L G L C P P |
| 17 FGF5-MM-003 | FGF5014 | C03 | 1.733 | 1.741 | 0.008 | T N I D S T P |
| 18 FGF5-MM-004 | FGF5014 | C10 | 1.74 | 1.778 | 0.038 | T N I D S T P |
| 19 FGF5-MM-005 | FGF5014 | G10 | 2.619 | 2.671 | 0.052 | L R I L A N K |
| 20 FGF5-MM-006 | FGF5015 | C11 | 1.427 | 2.194 | 0.767 | |
| 21 FGF5-MM-007 | FGF5015 | E04 | 1.378 | 1.644 | 0.266 | R T Q P Y P L |
| 22 FGF5-MM-008 | FGF5015 | H12 | 1.438 | 2.148 | 0.71 | G Y F I P S I |
| 23 FGF5-MM-009 | FGF5017 | C06 | | 2.516 | 0 | L L T P T L N |
| 24 FGF5-MM-015 | FGF5018 | G11 | 2.348 | 2.484 | 0.136 | T N I D S T P |
| 25 FGF5-MM-016 | FGF5018 | H12 | 1.618 | 1.983 | 0.365 | H L Q T T E T |
| 26 FGF5-MM-017 | FGF5019 | C06 | 1.599 | 1.652 | 0.053 | P L G L C P P |
| 27 FGF5-MM-018 | FGF5019 | C12 | 1.805 | 4.076 | 2.273 | T K I D S T P |
| 28 FGF5-MM-019 | FGF5019 | H01 | 1.623 | 1.771 | 0.148 | T K I D R T P |
| 29 FGF5-MM-020 | FGF5020 | E06 | 1.485 | 1.655 | 0.17 | X M A E Y M Y |
| 30 FGF5-MM-021 | FGF5020 | H04 | 1.497 | 2.658 | 1.161 | H L Q T T E T |

Binders to Plastics or FGF-5

| | | | | | | |
|---|---|---|---|---|---|---|
| 31 FGF5-MM-010 | FGF5017 | D09 | | 1.822 | 0 | A L P T H S N |
| 32 FGF5-MM-011 | FGF5017 | E06 | | 1.746 | 0 | |
| 33 FGF5-MM-012 | FGF5017 | F05 | | 2.039 | 0 | T N I D S T P |
| 34 FGF5-MM-013 | FGF5017 | G08 | | 2.309 | 0 | L C R R F E N |
| 35 FGF5-MM-014 | FGF5017 | G09 | | 1.71 | 0 | T N I D S T P |

Binders to FGF-5 Target and to Plastic/Casein

| | Plate | Position | Control Plate (OD490) | Target Plate (OD490) | Target-Control | |
|---|---|---|---|---|---|---|
| 36 FGF5-MM-022 | FGF5013 | A02 | 3.254 | 2.625 | -0.629 | R T L P H S Y |
| 37 FGF5-MM-023 | FGF5013 | G09 | 2.624 | 2.539 | -0.085 | A T P N H S Y |
| 38 FGF5-MM-024 | FGF5014 | A02 | 2.556 | 2.007 | -0.549 | P A I N R D P |
| 39 FGF5-MM-025 | FGF5016 | D06 | 3.194 | 2.753 | -0.441 | A T P N H S Y |
| 40 FGF5-MM-026 | FGF5016 | E12 | 2.696 | 2.294 | -0.402 | A T P N H S Y |
| 41 FGF5-MM-027 | FGF5020 | B01 | 2.579 | 2.222 | -0.357 | L M F D W T P |
| 42 FGF5-MM-028 | FGF5020 | E12 | 2.493 | 2.25 | -0.243 | L L T P T P N |
| 43 FGF5-MM-029 | FGF5020 | H09 | 2.357 | 2.177 | -0.18 | L L T P T L D |

FIG._10

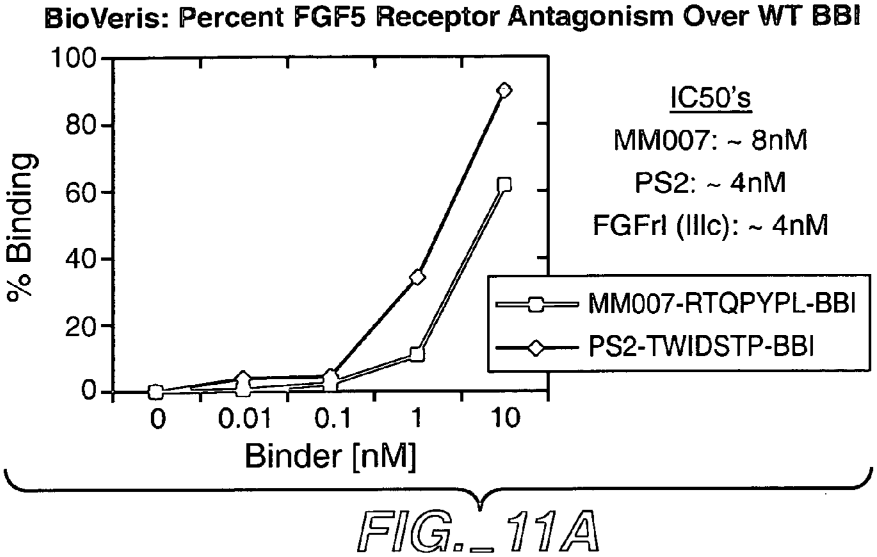
FIG._11A
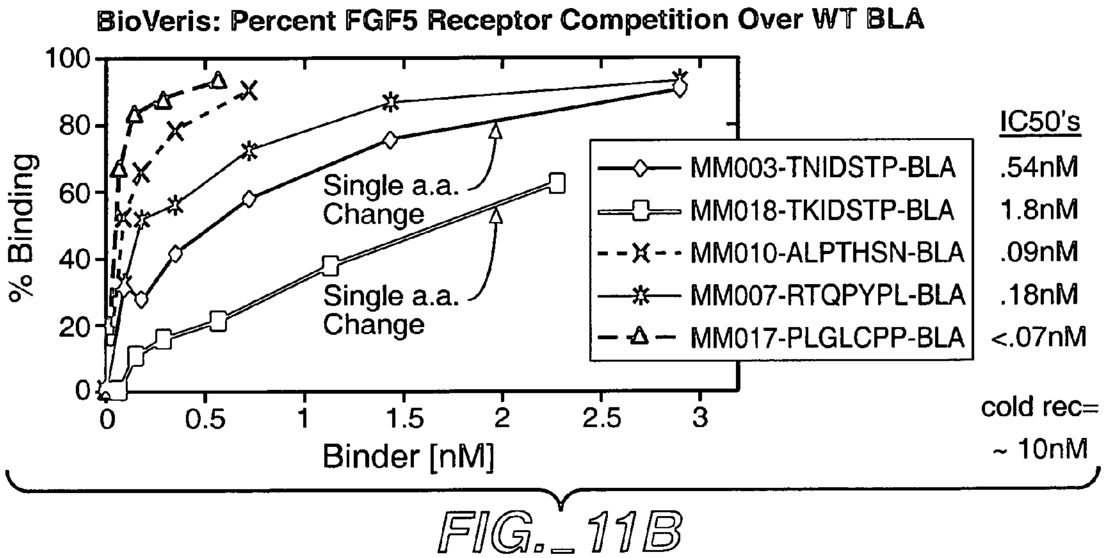
FIG._11B
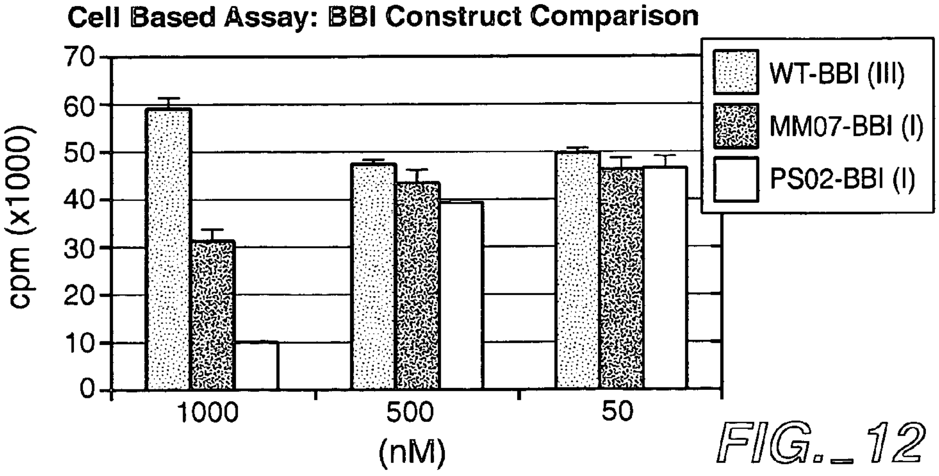
FIG._12

FGF-5 SUPPORTED AND BINDING PEPTIDES

The present application claims priority under 35 U.S.C. §119, to now abandoned U.S. Provisional Patent Application Ser. No. 60/518,154, filed Nov. 6, 2003, now abandoned U.S. Provisional Patent Application Ser. No. 60/520,403, filed Nov. 13, 2003, now abandoned U.S. Provisional Patent Application Ser. No. 60/530,954, filed Dec. 19, 2003, now abandoned U.S. Provisional Patent Application Ser. No. 60/531,207, filed Dec. 19, 2003, and now abandoned U.S. Provisional Patent Application Ser. No. 60/531,189, filed Dec. 19, 2003.

FIELD OF THE INVENTION

The present invention provides peptides and supported peptides that bind FGF-5 molecules.

BACKGROUND OF THE INVENTION

The Fibroblast Growth Factor (FGF) family is a superfamily of growth factors containing at least 23 members, many of which are potent regulators of cell proliferation, differentiation and cell function. All of the FGFs have a conserved 120 amino acid core. Members of the family share conserved cysteine residues and 30-50% sequence homology at the amino acid level. The molecular weight of the FGFs ranges from 7 kDa for FGF-1 to 38 kDa for FGF-5. The length of the proteins is from 60 amino acids in the case of an FGF-1 splice variant to 288 amino acids for FGF-2. Binding to heparin is an essential step required for an FGF factor to interact with cell surface receptors.

FGF5 is a secreted signaling protein consisting of 268 amino acids with a 17 amino acid signal sequence and a 251 amino acid mature peptide. The human gene also gives rise to a glycosylated alternate splice form that is 18 kDa in size and 123 amino acid in length. The murine homologue of FGF-5 was cloned and found to be 84% homologous to the human protein at the amino acid sequence level. Human FGF-5 consists of three exons and maps to chromosome 4q21 and cross-reacts with murine FGF-5.

Formation of hair follicles involves a complex series of steps: growth (anagen), regression (catagen), rest (telogen) and shedding (exogen). FGF-5 has been implicated as one of the major drivers of the transition from anagen to catagen in the hair cycle. Expression of FGF-5 is detected in hair follicles from wild-type mice and is localized to the outer root sheath during the anagen phase. Mice homozygous for a predicted null allele of FGF-5, fgf5neo, have abnormally long hair (See, Hebert et al., Cell 78: 1017-25 [1994]). The phenotype appears identical to that of mice homozygous for the spontaneous mutation angora (go). Recently, partial FGF-5 sequences, FGF5S, thought to compete with FGF-5 in binding to the receptor have been identified, (See, Ito et al., J. Cell Physiol., 197:272-83 [2003]).

The Bowman-Birk protease inhibitor (BBI) is a designation of a family of stable, low molecular weight trypsin and chymotrypsin enzyme inhibitors found in soybeans and various other seeds, mainly leguminous seeds and vegetable materials. BBI comprises a family of disulfide bonded proteins with a molecular weight of about 8 kD (See e.g., Chou et al., Proc. Natl. Acad. Sci. USA 71:1748-1752 [1974]; Yavelow et al., Proc. Natl. Acad. Sci. USA 82:5395-5399 [1985]; and Yavelow et al., Cancer Res. (Suppl.) 43:2454s-2459s [1983]). BBI has a pseudo-symmetrical structure of two tricyclic domains each containing an independent native binding loop, the native loops containing binding sites for both trypsin and chymotrypsin (See, Liener, in Summerfield and Bunting (eds), *Advances in Legume Science*, Royal Bot. Gardens, Kew, England). These binding sites each have a canonical loop structure, which is a motif found in a variety of serine proteinase inhibitors (Bode and Huber, Eur. J. Biochem., 204:433-451 [1992]). Commonly, as in one of the soybean inhibitors, one of the native loops inhibits trypsin and the other inhibits chymotrypsin (See, Chen et al., J. Biol. Chem., 267:1990-1994 [1992]; Werner & Wemmer, Biochem., 31:999-1010 [1992]; Lin et al., Eur. J. Biochem., 212:549-555 [1993]; and Voss et al., Eur. J. Biochem., 242: 122-131 [1996]) though in other organisms (e.g., *Arabidopsis*), both loops are specific for trypsin.

STI inhibits the proteolytic activity of trypsin by the formation of a stable stoichiometric complex (See e.g., Liu, Chemistry and Nutritional Value of Soybean Components, In: *Soybeans, Chemistry, Technology and Utilization*, pp. 32-35, Aspen Publishers, Inc., Gaithersburg, Md., [1999]). STI consists of 181 amino acid residues with two disulfide bridges and is roughly spherically shaped (See e.g., Song et al., J. Mol. Biol., 275:347-63 [1998]). The trypsin inhibitory loop lies within the first disulfide bridge. The Kunitz-type soybean trypsin inhibitor (STI) has played a key role in the early study of proteinases, having been used as the main substrate in the biochemical and kinetic work that led to the definition of the standard mechanism of action of proteinase inhibitors.

Eglin C is a small monomeric protein that belongs to the potato chymotrypsin inhibitor family of serine protease inhibitors. The proteins that belong to this family are usually small (60-90 amino acid residues in length) and contain no disulfide bonds. Eglin C, however, is highly resistant to denaturation by acidification or heat regardless of the lack of disulfide bonds to help stabilize its tertiary structure. The protein occurs naturally in the leech *Hirudo medicinalis*.

Despite much research into hair growth and its modulation, a need remains for efficient and effective means to modulate hair growth as desired.

SUMMARY OF THE INVENTION

The present invention provides peptides and supported peptides that bind FGF-5. In particularly preferred embodiments, the present invention provides cosmetic and/or pharmaceutical compounds for modulating hair growth. The present invention further provides peptides that block binding of FGF wherein the peptide is expressed in a protease-resistant scaffold. In some preferred embodiments, the scaffold is a protease inhibitor, such as BBI, STI or Eglin chymotrypsin inhibitor.

In some embodiments, the present invention provides cosmetic and/or pharmaceutical compounds comprising at least one polypeptide or a peptide suitable for modulating hair growth. In some preferred embodiments, the compounds comprise at least one polypeptide.

In alternative preferred embodiments, the compounds comprise at least one peptide. In some preferred embodiments, the peptide has an amino acid sequence selected from the group consisting of SEQ ID NOS:2, 4, 6, 8, 10, 12, and 14 (See, Table 1). In some preferred embodiments, the compound has a sequence, the sequence being at least 70%, preferably 80%, more preferably 90%, and most preferably 95% homologous to the sequences set forth herein. In some preferred embodiments, the polypeptide has a molecular weight that is preferably between 500 Daltons and 30,000 Daltons, more preferably between 1000 Daltons and 10,000 Daltons, and most preferably from 1500 Daltons to 8,000 Daltons.

In some preferred embodiments, modulation comprises treatment of at least one disease or condition that involves loss of hair. In some preferred embodiments, the disease or condition is at least one selected from the group consisting of inflammatory alopecias, pseudopelade, scleroderma, tick bites, lichen planus, psoriasis, lupus, seborrheic dermatitis, loose hair syndrome, hemochromatosis, androgenic alopecia, alopecia areata, cancer, conditions that affect defective hair fiber production, and environmental factors that affect hair production. In some preferred embodiments, the disease is androgenic alopecia or alopecia areata.

In some preferred embodiments, modulation comprises hair growth inhibition and/or hair removal for treatment of at least one disease or condition for which decreased hair growth is desirable. In some preferred embodiments, inhibition and/or removal comprises depilation.

In some preferred embodiments, the invention provides cosmetic and/or pharmaceutical compounds for modulating hair growth comprising at least one peptide or polypeptide and at least one scaffold, the peptide or polypeptide being contained in the scaffold, preferably the peptide or polypeptide being a loop, and most preferably, the loop being closed by a disulfide bond. In preferred embodiments, the peptide or polypeptide binds to FGF-5. In particularly preferred embodiments, the binding results in the blocking of the FGF-5 downstream activity. In some preferred embodiments, the scaffold is STI, Eglin or BBI. In particularly preferred embodiments, the scaffold is BBI. In further preferred embodiments, the peptide or polypeptide comprises a polypeptide.

In additional preferred embodiments, the compound comprises at least one peptide. In some preferred embodiments, the peptide has an amino acid sequence selected from the group consisting of SEQ ID NOS:2, 4, 6, 8, 10, 12, and 14 (See, Table). In other preferred embodiments, the compounds has an amino acid sequence comprising any sequence selected from the group consisting of SEQ ID NOS: 15-43 (See, FIG. 10). In some preferred embodiments, the compound has a sequence, the sequence being at least 70%, more preferably 80%, even more preferably 90%, and most preferably 95% homologous to the sequences set forth herein. In a preferred embodiment, the polypeptide has a molecular weight that is preferably between 500 Daltons and 100,000 Daltons, more preferably between 500 Daltons and 30,000 Daltons, even more preferably between 500 Daltons and 45,000 Daltons, still more preferably between 1000 Daltons and 12,000 Daltons, and most preferably from 1500 Daltons to 10,000 Daltons.

In some preferred embodiments, modulation comprises treatment of at least one disease or condition that involves loss of hair. In some preferred embodiments, the disease or condition is at least one selected from the group consisting of inflammatory alopecias, pseudopelade, scleroderma, tick bites, lichen planus, psoriasis, lupus, seborrheic dermatitis, loose hair syndrome, hemochromatosis, androgenic alopecia, alopecia areata, cancer, conditions that affect defective hair fiber production, and environmental factors that affect hair production. In some particularly preferred embodiments, the disease is androgenic alopecia or alopecia areata.

In some preferred embodiments, modulation comprises hair growth inhibition and/or hair removal for treatment of at least one disease or condition for which decreased hair growth is desirable. In some preferred embodiments, inhibition and/or removal comprises depilation.

In yet further embodiments, the present invention provides cosmetic and/or pharmaceutical compositions comprising at least one polypeptide or peptide, as set forth herein, and a physiologically acceptable carrier or excipient. Preferably, the compound is present in an amount of about 0.0001% to about 5% by weight based on the total weight of the composition. Also preferably, the compound is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

In yet further embodiments, the present invention provides means for decreasing FGF-5 activity. In some embodiments, the method comprising applying an effective amount of at least one of the compounds described herein to an organism in need thereof.

The present invention provides compositions comprising at least one peptide selected from the group consisting of SEQ ID NOS:2, 4, 6, 8, 10, 12, and 14, wherein said peptide binds to a fibroblast growth factor. In some embodiments, the peptide is encoded by a nucleic acid sequence selected from the group consisting of SEQ ID NOS:1, 3, 5, 7, 9, 11, and 13. In some preferred embodiments, the peptide is expressed in a protease resistant scaffold. In some particularly preferred embodiments, the scaffold is a protease inhibitor. In some preferred embodiments, the protease inhibitor is selected from the group consisting of Bowman-Birk Inhibitor, soybean trypsin inhibitor, and Eglin chymotrypsin inhibitor. In still further embodiments, the protease resistant scaffold and the peptide comprise a fusion protein.

The present invention also provides cosmetic and/or pharmaceutical composition comprising said at least one peptide that binds to a fibroblast growth factor. In some embodiments, the composition is capable of modulating hair growth. In some preferred embodiments, the composition further comprises a scaffold.

The present invention also provides methods for modulating hair growth comprising: i) providing a composition comprising a peptide contained within a scaffold; ii) providing a subject to be treated; and iii) applying the composition to the subject in an area in which hair growth modulation is desired. In some embodiments, the peptide binds to a fibroblast growth factor. In some preferred embodiments, the fibroblast growth factor (FGF) is FGF-5. In some particularly preferred embodiments, the scaffold is selected from the group consisting of Bowman-Birk inhibitor, soybean trypsin inhibitor, and Eglin chymotrypsin inhibitor. In some alternative embodiments, the peptide is selected from the group consisting of SEQ ID NOS: 2, 4, 6, 8, 10, 12, and 14. In some further embodiments, the peptide is encoded by a nucleic acid sequence selected from the group consisting of SEQ ID NOS: 1, 3, 5, 7, 9, 11, and 13.

The present invention also provides methods for decreasing the activity of a fibroblast growth factor comprising the steps of: i) providing a subject; and ii) administering a composition comprising at least one peptide that binds FGF to the subject, under conditions such that the activity of the fibroblast growth factor is decreased. In some embodiments, the fibroblast growth factor is FGF-5.

The present invention also provides compositions comprising an FGF-5 peptide sequence selected from the group of SEQ ID NOS:2, 4, 6, 8, 10, 12, 14, 15-43, 45-65, 68-84, 86, 88, 90, 92, 24, 26, 98, and 100.

In additional embodiments, the present invention provides applications for hair and/or skin treatment, as well as applications wound healing, treatment of proliferative diseases, etc. Thus, the present invention provides compositions and methods suitable for application in/on humans and other animals.

DESCRIPTION OF THE FIGURES

FIG. 1A provides the plasmid map for pME30.16.

FIG. 1B provides the plasmid map for p2JM103-DNNDPI-BBI.

FIG. 1C provides the plasmid map for pCB04.

FIG. 2 provides the first screen data obtained. In this graph, BLA activity is plotted against total BLA activity. The x-axis represents total BLA activity and the Y-axis represents bound BLA activity, as described in the Examples.

FIG. 3 provides data from the second screen, with the normalized data sets plotted against each other. The X-axis represents the normalized background, while the Y-axis represents the bound normalized, as described in the Examples.

FIG. 4 provides purification results for BLA-peptide fusion proteins purified by IMAC chromatography, as described in the Examples.

FIG. 5 provides an SDS-PAGE showing imidazole-eluted BLA active fragments, as described in the Examples.

FIG. 6 provides results of an assay for binding concentrations for peptide-BLA fusions. Panel A provides results for the following peptides: 2E2, 2H10, 2H9 and 1A6 and WT, as described in the Examples. Panel B provides results of an assay for binding concentrations for peptide-BLA fusions for the following peptides against a negative control: 2E2, 2H10, 2H9 and 1A6 and WT, as described in the Examples. Panel C provides results of an assay for binding concentrations for purified peptide-BLA fusions for the following peptides: 1C2 and 2E5 and WT. Panel D provides results of an assay for binding concentrations for purified peptide-BLA fusions for the following peptides against a negative control: 1C2 and 2E5 and WT.

FIG. 7 provides FGF-5 binding curves. Panel A provides a standard binding curve, as described in the Examples. Various concentrations of FGF-5 were added to quiescent NR6R-3T3 cells and proliferation was measured as described in the Examples. Panel B provides a binding curve showing pre-incubation of FGF-5+FGFrI(IIIc) to determine the neutralizing effect of antagonist, a receptor, on FGF-5 activity, and proliferation measured accordingly, as described in the Examples. Panel C provides a binding curve showing pre-incubation of BLA, alone, in addition to quiescent NR6R-3T3 cells and then measurement of proliferation, as described in the Examples. Panel D provides binding curves given pre-incubation of BLA-peptide fusions+FGF-5, the mixture being added to quiescent NR6R-3T3 cells with proliferation measured as described in the Examples. The peptide portions shown in the Figure are 2E2, 2H10, 2H9, and 1A6. Panel E provides binding curve data for pre-incubation of BLA-peptide fusions+FGF-5, the mixture being added to quiescent NR6R-3T3 cells with proliferation measured as described in the Examples. The peptide portions shown in the Figure are 1C2 and 2E5.

FIG. 8 provides the amino acid sequence (SEQ ID NO:44) of BBI backbone (71 amino acid residues). The loops are underlined.

FIG. 9 provides the sequence of FGF-5-binding BBI-peptide constructs (SEQ ID NOS:84-101) for mature BCE103 cellulase-BBI fusions with FGF-5 binders (See, Table 1) in either the trypsin or chymotrypsin loop, as indicated. Panel A provides the nucleotide and amino acid sequences of a construct with the 1A6 peptide in the trypsin loop. Panel B provides the nucleotide and amino acid sequences of a construct with the 1C2 peptide in the trypsin loop. Panel C provides the nucleotide and amino acid sequences of a construct with the 2E2 peptide in the trypsin loop. Panel D provides the nucleotide and amino acid sequences of a construct with the 2E5 peptide in the trypsin loop. Panel E provides the nucleotide and amino acid sequences of a construct with the 1A6 peptide in the chymotrypsin loop. Panel F provides the nucleotide and amino acid sequences of a construct with the 1C2 peptide in the chymotrypsin loop. Panel G provides the nucleotide and amino acid sequences of a construct with the 2E2 peptide in the chymotrypsin loop. Panel H provides the nucleotide and amino acid sequences of a construct with the 2E5 peptide in the chymotrypsin loop. The chymotrypsin and trypsin loops are underlined in each of above Panels.

FIG. 10 provides several selected binders from the screen set forth in Example 4. The left column indicates the clone designation, followed by the indication of plate, position and readings between the control plate and target plate. The last column provides the sequence of the selected binder.

The first two digits of the clone designation correspond to the sequence identifier number of the peptide. For example, 16 FGF5-MM-001 has peptide sequence PLGLCPP (SEQ ID NO: 16).

FIG. 11 provides two graphs (Panels A and B) showing results from BioVeris assays (Example 11) for selected BBI-peptide constructs. The percent binding was determined by subtracting the background (wild-type BBI) and calculating out of 100.

FIG. 12 provides a graph showing cell-based assay (Example 10) results obtained for wildtype BBI (WT-BBI) and two BBI-peptide constructs.

DESCRIPTION OF THE INVENTION

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology,* 2d Ed., John Wiley and Sons, NY (1994); and Hale and Marham, *The Harper Collins Dictionary of Biology*, Harper Perennial, NY (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a," "an," and "the"

includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

Definitions

As used herein, the term "fibroblast growth factor" (FGF) refers to any member of this family of proteins, known to those of skill in the art. In particularly preferred embodiments, the term is used in reference to FGF-5.

As used herein, in some embodiments, the "compound" comprises the "complete" protein, (i.e., in its entire length as it occurs in nature (or as mutated)), while in other embodiments it comprises a truncated form of a protein. Thus, the compounds of the present invention are either truncated or be "full-length." In addition, in some embodiments, the truncation is located at the N-terminal end, while in other embodiments the truncation is located at the C-terminal end of the protein. In further embodiments, the compound lacks one or more portions (e.g., sub-sequences, signal sequences, domains or moieties), whether active or not.

The term "organism" is used throughout the specification to describe an animal, preferably a human, to whom treatment, including prophylactic treatment, with the compounds according to the present invention is provided. For treatment of those infections, conditions or disease states which are specific for a specific animal such as a human patient, the term organism refers to that specific animal.

The "host cells" used in the present invention generally are prokaryotic or eukaryotic hosts which contain an expression vector and/or gene of interest. Host cells are transformed or transfected with vectors constructed using recombinant DNA techniques. Such transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

The term "effective amount" is used throughout the specification to describe concentrations or amounts of compounds according to the present invention which may be used to produce a favorable change in the disease or condition treated, whether that change is hair growth or prevention of hair growth.

As used herein, "vitamin $B_3$ compound" means a compound having the formula:

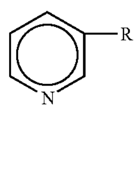

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

As used herein, "non-vasodilating" means that an ester does not commonly yield a visible flushing response after application to the skin in the subject compositions. It is contemplated that the majority of the general population would not experience a visible flushing response, although such compounds may cause vasodilation not visible to the naked eye.

As used herein, "retinoid" includes all natural and/or synthetic analogs of Vitamin A and/or retinol-like compounds which possess the biological activity of Vitamin A in/on the skin, as well as the geometric isomers and stereoisomers of these compounds.

As used herein, the term "bioactivity" refers to a cause and effect relationship between a composition and a biological system. Thus, the term is used as by those skilled in the art of biotechnology and biological sciences as the phrase that describes a cause and effect relationship between a molecular composition and living biological matter (e.g., tissue, cells, etc.).

As used herein as a noun, the term "bioactive" refers a composition that exhibits bioactivity upon administration to living biological matter (e.g., tissue, cells, etc.). The term is used synonymously with "bioactive compound."

As used herein, "silicone gum" means high molecular weight silicones having an average molecular weight in excess of about 200,000 and preferably from about 200,000 to about 4,000,000. It is intended that the definition encompass non-volatile polyalkyl and polyaryl siloxane gums.

As used herein, the term "polypeptide" refers to a compound made up of a single chain of amino acid residues linked by peptide bonds. The term "protein" herein may be synonymous with the term "polypeptide" or may refer, in addition, to a complex of two or more polypeptides. The exact meaning is that known to those in the art.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. The term "expression cassette" may be used interchangeably herein with "DNA construct" and its grammatical equivalents.

As used herein, the terms "vector" and "cloning vector" refer to nucleic acid constructs designed to transfer nucleic acid sequences into cells.

As used herein, the term "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those of skill in the art.

As used herein, the term "plasmid" refers to a circular double-stranded (ds) DNA construct used as a cloning vector, and which forms an extrachromosomal self-replicating genetic element in some eukaryotes or integrates into the host chromosomes.

As used herein, the term "expression" refers to the process by which a polypeptide is produced based on the nucleic acid sequence of the gene or the chemical synthetic peptide. The process includes both transcription and translation of the gene to produce polypeptide/protein.

As used herein, the term "gene" means the segment of DNA involved in producing a polypeptide chain that may or may not include regions preceding or following the coding region.

As used herein, the terms "nucleic acid molecule" and "nucleic acid sequence" include sequences of any form of nucleic acid, including, but not limited to RNA, DNA and cDNA molecules. It will be understood that, as a result of the degeneracy of the genetic code, a multitude of nucleotide sequences encoding a given protein may be produced, in addition to mutant proteins.

As used herein, "codon" refers to a sequence of three nucleotides in a DNA or mRNA molecule that represents the instruction for incorporation of a specific amino acid into a polypeptide chain.

As used herein, the term "disulfide bridge" or "disulfide bond" refers to the bond formed between the sulfur atoms of cysteine residues in a polypeptide or a protein. In this invention, a disulfide bridge or disulfide bond may be non-naturally occurring and introduced by way of point mutation.

As used herein, the term "salt bridge" refers to the bond formed between oppositely charged residues, amino acids in a polypeptide or protein. In this invention, a salt bridge may be non-naturally occurring and introduced by way of point mutation.

As used herein, an "enzyme" refers to a protein or polypeptide that catalyzes at least one chemical reaction.

As used herein, the term "activity" refers to any activity associated with a particular protein, such as enzymatic activity associated with a protease. In some embodiments, the activity is biological activity. In further embodiments, activity encompasses binding of proteins to receptors which results in measurable downstream effects, such as inhibition of the transition from anagen to catagen, as described herein. "Biological activity" refers to any activity that would normally be attributed to that protein by one skilled in the art.

As used herein, the term "protease" refers to an enzyme that degrades peptide bonds.

As used herein, "peptide bond" refers to the chemical bond between the carbonyl group of one amino acid and the amino group of another amino acid.

As used herein, "wild-type" refers to a sequence or a protein that is native or naturally occurring.

As used herein, "point mutations" refers to a change in a single nucleotide of DNA, especially where that change results in a sequence change in a protein.

As used herein, "mutant" refers to a version of an organism or protein where the version is other than wild-type. The change may be effected by methods well known to one skilled in the art, for example, by point mutation in which the resulting protein may be referred to as a mutant.

As used herein, "mutagenesis" refers to the process of changing a composition (e.g., protein) from a wild-type composition (e.g., protein) into a mutant or variant composition (e.g., protein).

As used herein, "substituted" and "substitutions" refer to replacement(s) of an amino acid residue or nucleic acid base in a parent sequence. In some embodiments, the substitution involves the replacement of a naturally occurring residue or base.

As used herein, "modification" and "modify" refer to any change(s) in an amino acid or nucleic acid sequence, including, but not limited to deletions, insertions, interruptions, and substitutions. In some embodiments, the modification involves the replacement of a naturally occurring residue or base.

As used herein, "functional portion of a secreted polypeptide" and its grammatical equivalents refers to a truncated secreted polypeptide that retains its ability to fold into a normal, albeit truncated, configuration. In some embodiments, it is contemplated that sufficient residues of a domain of the naturally secreted polypeptide must be present to allow it to fold in its normal configuration independently of the desired polypeptide to which it is attached. However, in most cases, the portion of the secreted polypeptide are both correctly folded and result in increased secretion as compared to its absence. Similarly, in most cases, the truncation of the secreted polypeptide means that the functional portion retains a biological function. In a preferred embodiment, the catalytic domain of a secreted polypeptide is used, although other functional domains may be used, for example, the substrate binding domains. Additionally preferred embodiments utilize the catalytic domain and all or part of the linker region.

As used herein, "loop" refers to a sequence of amino acids, for example 3-20 amino acids, more preferably 5-15 amino acids, even more preferably 5-10 amino acids, and most preferably 7-9 amino acids, which connects structural elements of a protein. Such elements include, but are not limited to beta sheets and helical elements and the connecting loop of a beta-hairpin. In some embodiments, the loop is further stabilized through the use of covalent linkages. In some preferred embodiments, the covalent linkages comprise disulfide bonds, especially as provided herein. In alternative embodiments, the loops are stabilized by the use of other means, including but not limited to amides, hydrogen bonds, and/or salt bridges. In most embodiments, the loops are located on the surface of proteins and may be altered, as provided herein, to confer additional (e.g., desirable) properties to the requisite proteins.

As used herein, "oligonucleotide" refers to a short nucleotide sequence which may be used, for example, as a primer in a reaction used to create mutant proteins.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method well-known in the art (See e.g., U.S. Pat. Nos. 4,683,195 4,683,202, and 4,965,188, hereby incorporated by reference), for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the term "hybridization" refers to the process by which a strand of nucleic acid joins with a complementary strand through base pairing, as known in the art.

As used herein, "maximum stringency" refers to the level of hybridization that typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The phrases "substantially similar and "substantially identical" in the context of two nucleic acids or polypeptides typically means that a polynucleotide or polypeptide comprises a sequence that has at least 75% sequence identity, preferably at least 80%, more preferably at least 90%, still more preferably 95%, most preferably 97%, sometimes as much as 98% and 99% sequence identity, compared to the reference (i.e., wild-type) sequence. Sequence identity may be determined using known programs such as BLAST, ALIGN, and CLUSTAL using standard parameters. (See e.g., Altschul, et al., J. Mol. Biol. 215:403-410 [1990]; Henikoff et al., Proc. Natl. Acad Sci. USA 89:10915 [1989]; Karin et al., Proc. Natl Acad. Sci USA 90:5873 [1993]; and Higgins et al., Gene 73:237-244 [1988]). Software for performing BLAST analyses is publicly available through the National Center for Biotechnology Information. Also, databases may be searched using FASTA (Pearson et al., Proc. Natl. Acad. Sci. USA 85:2444-2448 [1988]).

As used herein, "equivalent residues" refers to proteins that share particular amino acid residues. For example, equivalent resides may be identified by determining homology at the level of tertiary structure for a protein (e.g., FGF-5) whose tertiary structure has been determined by x-ray crystallography. Equivalent residues are defined as those for which the atomic coordinates of two or more of the main chain atoms of a particular amino acid residue of the protein having putative equivalent residues and the protein of interest (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins analyzed. The preferred model is the crystallographic model giving the lowest R factor for experimental diffraction data at the highest resolution available, determined using methods known to those skilled in the art of crystallography and protein characterization/analysis.

In some embodiments, modification is preferably made to the "precursor DNA sequence" which encodes the amino acid sequence of the precursor enzyme, but can be by the manipulation of the precursor protein. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. Derivatives provided by the present invention further include chemical modification(s) that change the characteristics of the protein.

In some preferred embodiments, the protein gene is ligated into an appropriate expression plasmid. The cloned protein gene is then used to transform or transfect a host cell in order to express the protein gene. In some embodiments, this plasmid replicates in the hosts, in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed, by the host), a transcription terminator (a polyadenylation region for eukaryotic host cells) which is exogenous or is supplied by the endogenous terminator region of the protein gene. In some embodiments, a selection gene such as an antibiotic resistance gene that enables continuous cultural maintenance of plasmid-infected host cells by growth in antimicrobial-containing media is also included.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "fusion protein" refers to a chimeric protein containing the protein of interest (i.e., FGF-5 and/or fragments thereof) joined to an exogenous protein fragment (the fusion partner which consists of a non-FGF-5 protein). In some embodiments, the fusion partner enhances solubility of the FGF-5 protein as expressed in a host cell, may provide an affinity tag to allow purification of the recombinant fusion protein from the host cell or culture supernatant, or both. If desired, the fusion protein may be removed from the protein of interest (i.e., FGF-5 and/or fragments thereof) by a variety of enzymatic or chemical means known to the art.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein the term "coding region" when used in reference to structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "purified" or "to purify" refers to the removal of contaminants from a sample. For example, recombinant FGF-5 polypeptides are expressed in host cells and the polypeptides are purified by the removal of host cell proteins; the percent of recombinant FGF-5 polypeptides is thereby increased in the sample.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a FGF-5 protein includes, by way of example, such nucleic acid in cells ordinarily expressing a FGF-5 protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, "anagen" refers to the active growth phase of hair follicles. In the anagen phase, cells in the root of the hair divide rapidly, adding to the hair shaft. During this phase, the hair grows about 1 cm every 28 days. Scalp hair stays in this active phase of growth for 2-6 years.

As used herein, "catagen" refers to the hair growth phase that occurs at the end of the anagen phase. It signals the end of the active growth of a hair. This phase lasts for about 2-3 weeks while a club hair is formed.

As used herein, "telogen" refers to the resting phase of the hair follicle. At any given time, 10%-15% of all hairs are in the telogen phase. This phase lasts for about 100 days for hairs on the scalp and much longer for hairs on the eyebrows, eyelashes, arms and legs. During this phase, the hair follicle is completely at rest and the club hair is completely formed.

Pulling out a hair in this phase will reveal a solid, hard, dry, white material at the root. About 25-100 telogen hairs are shed normally each day.

As used herein, "depilation" refers to the act of removing hair. "Depilatories" are compositions that are used to remove hair.

As used herein, "alopecia" refers to loss of hair. Hair loss is thought to proceed by mechanisms involving FGF-5, as described herein. However, it is not intended that the present invention be limited to any particular mechanism in hair loss.

As used herein, "cosmetic composition" refers to compositions that find use in the cosmetics. The Food Drug and Cosmetic Act (FD&C Act) definition is used herein. Thus, cosmetics are defined by their intended use, as articles intended to be rubbed, poured, sprinkled, or sprayed on, introduced into, or otherwise applied to the human body for cleansing, beautifying, promoting attractiveness, or altering appearance. These compositions provide non-therapeutic benefits and are not regulated as pharmaceuticals. However, in some situations, cosmetic compositions are incorporated into pharmaceutical compositions to provide cosmetic benefits (e.g., products that treat skin or hair diseases, but also contain cosmetic compositions for their coloring or other benefits). Also, it is intended that the present invention encompass the use of cosmetics on animals other than humans.

As used herein, the terms "pharmaceutical compositions" and "therapeutic compositions" refer to compositions such as drugs that provide medical benefits, rather than solely cosmetic benefits. In the United States, pharmaceutical and therapeutic compositions are approved by the Food and Drug Administration for treatment and/or prevention of particular conditions.

As used herein, the term "drug" is defined as it is in the FD&C Act definition. Thus, drugs are defined as articles intended for use in the diagnosis, cure, mitigation, treatment or prevention of disease, and articles (other than food) intended to affect the structure or any function of the body of man or other animals.

As used herein, the term "cosmetic benefit" refers to a desired cosmetic change that results from the administration of a personal care composition. Cosmetic benefits include but are not limited to improvements in the condition of skin, hair, nails, and the oral cavity. In preferred embodiments, at least one cosmetic benefit is provided by the skin care, hair care, nail care, and makeup compositions of the present invention.

As used herein, "skin care composition" refers to compositions that are applied to skin in order to provide beneficial properties, including but not limited to wrinkle minimizing, wrinkle removal, decoloring, coloring, skin softening, skin smoothing, dipilation, cleansing, etc. In some particularly preferred embodiments, the present invention provides skin care compositions that improve skin tone. In these embodiments, the improvement comprises lessening of wrinkles, smoothing skin texture, modifying skin coloration, and other desired cosmetic benefits.

As used herein, "hair care composition" refers to compositions that are applied to hair to provide beneficial properties such as thickening, thinning, coloring, decoloring, cleansing, conditioning, softening, shaping, etc.

As used herein, "makeup compositions" refer to cosmetic preparations that are used to beautify, caring for, maintaining, or augment the appearance of a human or other animal. "Makeup compositions" include, but are not limited to color cosmetics, such as mascaras, lipsticks, lip liners, eye shadows, eye-liners, rouges, face powders, foundations, blushes, and nail polish.

As used herein, the term "dispersed phase" is used as by those of skill in the art of emulsion technology as the phase that exists as small particles or droplets suspended in and surrounded by a continuous phase. The dispersed phase is also known as the "internal" or "discontinuous" phase.

As used herein, "penetration enhancers" refer to compositions that facilitate penetration through the upper stratum corneum barrier to the deeper skin layers. Examples of penetration enhancers include, but are not limited to, propylene glycol, azone, ethoxydiglycol, dimethyl isosorbide, urea, ethanol, dimethyl sulfoxide, micoroemulsions, liposomes, and nanoemulsions.

As used herein, the terms "emulsifier" and "surfactant" refer to compounds that disperse and suspend the dispersed phase within the continuous phase of a material. Surfactants find particular use in products intended for skin and/or hair cleansing. In particular embodiments, the term "surfactant(s)" is used in reference to surface-active agents, whether used as emulsifiers or for other surfactant purposes such as skin cleansing.

DETAILED DESCRIPTION OF THE INVENTION

The present invention provides peptides and supported peptides that bind FGF-5.

In some embodiments, the present invention provides cosmetic and/or pharmaceutical compounds for modulating hair growth comprising at least one polypeptide or a peptide. In some preferred embodiments, the compounds comprise a polypeptide.

In alternative preferred embodiments, the compounds comprise at least one peptide. In some preferred embodiments, the peptide has an amino acid sequence selected from the group consisting of SEQ ID NOS:2, 4, 6, 8, 10, 12, and 14 (See, Table 1). In some preferred embodiments, the compound has a sequence, the sequence being at least 70%, preferably 80%, more preferably 90%, and most preferably 95% homologous to the sequences set forth herein. In some preferred embodiments, the polypeptide has a molecular weight that is preferably between 500 Daltons and 30,000 Daltons, more preferably between 1000 Daltons and 10,000 Daltons, and most preferably from 1500 Daltons to 8,000 Daltons.

In some preferred embodiments, modulation comprises treatment of at least one disease or condition that involves loss of hair. In some preferred embodiments, the disease or condition is at least one selected from the group consisting of inflammatory alopecias, pseudopelade, scleroderma, tick bites, lichen planus, psoriasis, lupus, seborrheic dermatitis, loose hair syndrome, hemochromatosis, androgenic alopecia, alopecia areata, cancer, conditions that affect defective hair fiber production, and environmental factors that affect hair production. In some preferred embodiments, the disease is androgenic alopecia or alopecia areata.

In some preferred embodiments, modulation comprises hair growth inhibition and/or hair removal for treatment of at least one disease or condition for which decreased hair growth is desirable. In some preferred embodiments, inhibition and/or removal comprises depilation.

In some preferred embodiments, the invention provides cosmetic and/or pharmaceutical compounds for modulating hair growth comprising at least one peptide or polypeptide and at least one scaffold, the peptide or polypeptide being contained in the scaffold, preferably the peptide or polypeptide being a loop, and most preferably, the loop being closed by a disulfide bond. In preferred embodiments, the peptide or polypeptide binds to FGF-5. In particularly preferred embodiments, the binding results in the blocking of the FGF-5 downstream activity. In some preferred embodiments, the scaffold is STI, Eglin or BBI. In particularly preferred embodiments, the scaffold is BBI. In further preferred embodiments, the peptide or polypeptide comprises a polypeptide.

In additional preferred embodiments, the compound comprises at least one peptide. In some preferred embodiments, the peptide has an amino acid sequence selected from the group consisting of SEQ ID NOS:2, 4, 6, 8, 10, 12, and 14 (See, Table 1). In other preferred embodiments, the compounds has an amino acid sequence comprising any sequence selected from the group consisting of SEQ ID NOS: 15-43 (See, FIG. 10). In some preferred embodiments, the compound has a sequence, the sequence being at least 70%, more preferably 80%, even more preferably 90%, and most preferably 95% homologous to the sequences set forth herein. In a preferred embodiment, the polypeptide has a molecular weight that is preferably between 500 Daltons and 100,000 Daltons, more preferably between 500 Daltons and 30,000 Daltons, even more preferably between 500 Daltons and 45,000 Daltons, still more preferably between 1000 Daltons and 12,000 Daltons, and most preferably from 1500 Daltons to 10,000 Daltons.

In some preferred embodiments, modulation comprises treatment of at least one disease or condition that involves loss of hair. In some preferred embodiments, the disease or condition is at least one selected from the group consisting of inflammatory alopecias, pseudopelade, scleroderma, tick bites, lichen planus, psoriasis, lupus, seborrheic dermatitis, loose hair syndrome, hemochromatosis, androgenic alopecia, alopecia areata, cancer, conditions that affect defective hair fiber production, and environmental factors that affect hair production. In some particularly preferred embodiments, the disease is androgenic alopecia or alopecia areata.

In some preferred embodiments, modulation comprises hair growth inhibition and/or hair removal for treatment of at least one disease or condition for which decreased hair growth is desirable. In some preferred embodiments, inhibition and/or removal comprises depilation.

In yet further embodiments, the present invention provides cosmetic and/or pharmaceutical compositions comprising a polypeptide or peptide, as set forth herein, and a physiologically acceptable carrier or excipient. Preferably, the compound is present in an amount of about 0.0001% to about 5% by weight based on the total weight of the composition. Also preferably, the compound is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

In yet further embodiments, the present invention provides means for decreasing FGF-5 activity. In some embodiments, the method comprising applying an effective amount of at least one of the compounds described herein to an organism in need thereof.

In additional preferred embodiments, the present invention is directed to at least one peptide or polypeptide, at least one loop and at least one protease-resistant scaffold. Flexible native loops are found on the surface of most protein modules and exist as short stretches of amino acids that connect regions of defined secondary structure. Although crystallographic and NMR (nuclear magnetic resonance) studies show that native loops are usually less well defined than alpha-helices and beta-sheets, their conformational freedom is normally restricted substantially compared with free peptides. Consequently, the binding activities of native loops in proteins usually differ significantly from those of the corresponding linear amino acid sequence. However, it is not intended that the present invention be limited to any specific mechanism.

The loops provided by the present invention bind proteins such as FGF (e.g., FGF-5). Binding the loop to the protein prevents the protein from binding to its target. Thus, binding interactions are thought to be disrupted by binding the loop to the protein. As a result, bioactivity can be altered as desired. However, it is not intended that the present invention be limited to any particular mechanism.

The present invention further provides scaffolds to stabilize the loops. STI, BBI and EglinC have native loops that bind to and inhibit proteases. In some embodiments, STI and BBI native loops are replaced with the polypeptides and/or peptides of the invention. In some embodiments, these sequences are replaced with inhibitors or enhancers of any FGF, while in other embodiments, the sequences are replaced with inhibitors or enhancers of FGF-5. In additional embodiments, STI and BBI native loops are replaced with sequences that have been isolated using various techniques known in the art (e.g., phage display), such as the FGF-5 binding proteins described herein.

In some embodiments, a native loop is replaced with a loop which is 3 to 20 amino acids in length, preferably 5 to 15 amino acids in length, and more preferably 5 to 10 amino acids in length. In alternative embodiments, longer sequences find use, as long as they provide binding and/or inhibition. In addition, peptides suitable for use as replacements of the native loop(s) can form constrained loops (i.e., a loop formed by the presence to a disulfide bond between two cysteine residues). In some particularly preferred embodiments, the peptides are between 7 and 9 amino acids in length.

There are several advantages to using scaffolds to stabilize peptide sequences. In some preferred embodiments, the biological activity of the peptide is higher and/or effectively modulates biological function as a result of limiting peptide flexibility and reducing the entropic cost of fixing the polypeptide sequence in the bioactive conformation. In addition, structural information obtained by x-ray crystallography finds use in guiding affinity maturation. Furthermore, in some embodiments, the sequence presented on a structural scaffold is more resistant to proteolytic degradation in different biological applications. In still further embodiments, the chimeric construction is obtained in large amount in low cost biological expression systems for industrial applications.

As shown in the Examples, in some embodiments, the present invention provides compounds that bind FGF-5. In some embodiments, binding absorbs extracellular FGF-5, thereby preventing FGF-5 from interacting with its cognate ligand, when then prevents downstream biological effect(s). In the present invention, binding prevents FGF-5 from interacting with its cognate receptor and inhibits transition from the anagen to the catagen promoting hair growth and preventing hair loss.

BBI represents a class of protein scaffolds whose binding to proteases is mediated by an exposed native loop that is fixed in a characteristic canonical conformation and which fits into the active site in a manner thought to be similar to that of a substrate (Laskowski and Kato, Ann. Rev. Biochem., 49:593-626 [1980]; and Bode & Huber, supra). The native loop is frequently constrained by the presence of disulfide bridges and/or extensive hydrogen-bonding networks that act to lock the structure into the correct canonical structure. The sequence of this loop determines the specificity of the inhibition, which mirrors the specificity of proteases for their substrates. For example, most trypsin inhibitors have Arg or Lys as their P1 residue. Inhibitors of the BBI family have a network of conserved disulfide bridges that help form a symmetrical structure of two tricyclic domains (Chen et al., supra; Werner and Wemmer, supra; and Liu et al., supra), each containing an independent serine protease binding site. The native binding loop is contained within a region joined by disulfide bridges formed between cysteine residues. The identity of the amino acid residue at the P1 site on each domain is the main determinant of the serine protease inhibited. Native domains possess lysine or arginine for trypsin, leucine or tyrosine for chymotrypsin and alanine for elastase (Tsunogae et al., J. Biochem. (Tokyo) 100:243-246 [1986]). In addition, serine is highly conserved at the P'1 position and proline at the P'3 position. The individual native loop regions of BBI are well suited for protein loop grafting of previously identified cysteine constrained peptides that bind to targets selectively, as described herein.

Numerous isoforms of BBI have been characterized. For example, SEQ ID NO:44 (See, FIG. 8) provides the amino acid sequence of a BBI backbone described herein comprising approximately 71 amino acid residues. In addition, in some embodiments BBI is truncated with as many as 10 amino acid residues being removed from either the N- or C-terminal. Any of the isoforms described herein, as well as those additional ones known in the art, find use as scaffolds in the present invention.

The present invention provides several advantages over creation of, for example, chimeric proteins. Transfer of an entire protein can be difficult when, for example, a protein domain of interest carries more than one important biological activity. Maintaining one activity (e.g. functionally significant domain-domain interactions) while altering another (e.g. high affinity binding to a co-factor or receptor) can be problematic. The present invention, as indicated herein, overcomes that limitation, as in preferred embodiments the loops are transferred, instead of entire domains.

In addition, in some embodiments, the compounds of the present invention comprise at least one mutation in addition to those set out above. Other mutations, such as deletions, insertions, substitutions, transversions, transitions and inversions, at one or more other locations, also find use in the present invention.

In some embodiments, the compounds of the present invention also comprise a conservative substitution that may occur as a like-for-like substitution (e.g., basic for basic, acidic for acidic, polar for polar etc.). In additional embodiments, non-conservative substitutions are provided (i.e., from one class of residue to another or alternatively involving the inclusion of unnatural amino acids such as ornithine, diaminobutyric acid ornithine, norleucine ornithine, pyriylalanine, thienylalanine, naphthylalanine and phenylglycine).

In some embodiments, the sequences also have deletions, insertions and/or substitutions of amino acid residues that produce a silent change and result in a functionally equivalent substance.

In some embodiments, deliberate amino acid substitutions are made on the basis of similarity in amino acid properties (e.g., polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (See e.g., Livingstone and Barton, Comput. Appl Biosci., 9:745-756 [1993]; and (Taylor, J. Theor. Biol., 119:205-218 [1986]). In some embodiments, conservative substitutions are made, for example according to the table below that describes a generally accepted Venn diagram grouping of amino acids.

| Set | | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

In some embodiments, variant amino acid sequences of the present invention also include suitable spacer groups inserted between any two amino acid residues of the sequence including alkyl groups such as methyl, ethyl or propyl groups in addition to amino acid spacers such as glycine or β-alanine residues. A further form of variation involves the presence of one or more amino acid residues in peptoid form.

In some embodiments, homology comparisons find use in identifying homologous sequences that find use in the present invention. Homology comparisons can be conducted by eye, or more usually, with the aid of readily available sequence comparison programs. Available computer programs can calculate the percent homology between two or more sequences. Additionally, percent homology may be calculated over contiguous sequences (i.e., one sequence is aligned with the other sequence and each amino acid in one sequence is directly compared with the corresponding amino acid in the other sequence one residue at a time). This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximize local homology.

However, these more complex methods assign "gap penalties" to each gap that occurs in the alignment, so that for the same number of identical amino acids, a sequence alignment with as few gaps as possible (i.e., reflecting higher relatedness between the two compared sequences) will achieve a higher score than one with many gaps. "Affine gap costs" are typically used that charge a relatively high cost for the existence of a gap and a smaller penalty for each subsequent residue in the gap. This is one of the most commonly used gap scoring system. High gap penalties will of course produce optimized alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (See e.g., Devereux et al., Nuc. Acids Res., 12:387 [1984]). Examples of other software packages than can perform sequence comparisons include, but are not limited to, the BLAST package FASTA, and the GENEWORKS suite of comparison tools, all of which are well-known to those in the art. Both BLAST and FASTA are available for offline and online searching. However, for some applications, it is preferred to use the GCG Bestfit program. The BLAST 2 Sequence package is also available for comparing protein and nucleotide sequences.

Although the final percent homology can be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (See e.g., Higgins and Sharp, Gene 73:237-244 [1988]).

Once the software has produced an optimal alignment, it is possible to calculate the percent of homology, and more preferably, the percent of sequence identity. The software typically does this as part of the sequence comparison and generates a numerical result.

In some embodiments, the present invention provides nucleic acids encoding any of the compounds described herein, as well as complements thereof. In additional preferred embodiments, the invention provides vectors comprising a compound, as disclosed herein, cells comprising the compound and methods of expressing the compound.

Those of skill in the art appreciate the relationship between nucleic acid sequences and polypeptide sequences, in particular as relate to the genetic code and the degeneracy of this code, and will be able to construct such nucleic acids without difficulty. For example, one skilled in the art is aware that for each amino acid substitution in a sequence there may be one or more codons that encode the substitute amino acid. Accordingly, it is evident that, depending on the degeneracy of the genetic code with respect to that particular amino acid residue, one or more nucleic acid sequences may be generated corresponding to that polypeptide sequence.

Mutations in amino acid sequence and nucleic acid sequence may be made by any of a number of techniques, as known in the art. In particularly preferred embodiments, the mutations are introduced into parent sequences by means of PCR (polymerase chain reaction) using appropriate primers. In some embodiments, the parent enzymes are modified at the amino acid level, while in other embodiments, the enzymes are modified at the nucleic acid level, in order to generate the sequences described herein. In some preferred embodiments, the present invention provides for the generation of compounds by introducing one or more corresponding codon changes in the nucleotide sequence encoding a compound. It will be appreciated that the above codon changes will find use in various nucleic acid sequences of the present invention. For example, in some embodiments, sequence changes are made to any of the homologous sequences described herein.

As indicated above, in some embodiments, the "compound" comprises the "complete" protein, (i.e., in its entire length as it occurs in nature (or as mutated)), while in other embodiments it comprises a truncated form of a protein. Thus, the compounds of the present invention are either truncated or be "full-length." In addition, in some embodiments, the truncation is located at the N-terminal end, while in other embodiments the truncation is located at the C-terminal end of the protein. In further embodiments, the compound lacks one or more portions (e.g., sub-sequences, signal sequences, domains or moieties), whether active or not.

In yet further alternative embodiments, the nucleotide sequences encoding the compounds are prepared synthetically by established standard methods (e.g. the phosphoroamidite method described by Beucage et al., Tetrahedr. Lett., 22:1859-1869 [1981]; or the method described by Matthes et al., EMBO J., 3:801-805 [1984]). In the phosphoroamidite method, oligonucleotides are synthesized (e.g., in an automatic DNA synthesizer), purified, annealed, ligated and cloned in appropriate vectors.

In some embodiments of the present invention, the nucleotide sequences are either of mixed genomic and synthetic origin, mixed synthetic and cDNA origin or mixed genomic and cDNA origin, prepared by ligating fragments of synthetic, genomic or cDNA origin, in accordance with standard techniques. Each ligated fragment corresponds to various parts of the entire nucleotide sequence. In some embodiments, the DNA sequence is prepared by polymerase chain reaction (PCR) using specific primers, as known in the art.

In some embodiments, the nucleotide sequences described here and suitable for use in the methods and compositions described here include within them synthetic or modified nucleotides. A number of different types of modification to oligonucleotides are known in the art. These include, but are not limited to methylphosphonate and phosphorothioate backbones and/or the addition of acridine or polylysine chains at the 3' and/or 5' ends of the molecule. However, it is not intended that the present invention be limited to any particular method, as any suitable method known to those in the art for modifying nucleotide sequences find use in the present invention. In some embodiments, these modifications are performed in order to enhance the in vivo activity and/or life span of nucleotide sequences.

In some preferred embodiments, the present invention provides nucleotide sequences and methods for using nucleotide sequences that are complementary to the sequences presented herein, as well as derivatives and/or fragments of these sequences.

In some embodiments, the polynucleotides of the present invention find use in the production of primers and/or probes. Thus, in some embodiments, the polynucleotide sequences are used to produce PCR primers, primers for other amplification methods as known in the art, labeled probes, and/or for cloning methods. In preferred embodiments, these primers, probes and other fragments are at least 15, preferably at least 20, and in some more preferable embodiments, at least 25, 30 or 40 nucleotides. In addition, these primers, probes and fragments are encompassed by the term "polynucleotide."

In some embodiments, polynucleotides such as DNA polynucleotides and probes are produced recombinantly, while in other embodiments they are produced synthetically. In additional embodiments, these sequences are cloned using standard methods. In general, primers are produced by synthetic means, involving a stepwise manufacture of the desired nucleic acid sequence one nucleotide at a time. Techniques for accomplishing this using automated techniques are readily available in the art. However, it is not intended that the present invention be limited to production of polynucleotides using any particular method, as any suitable method known to those in the art finds use in the present invention.

In some embodiments, longer polynucleotides are generally be produced using recombinant means, for example using PCR cloning techniques, as known in the art. In such embodiments, the primers are typically designed to contain suitable restriction enzyme recognition sites so that the amplified DNA can be readily cloned into a suitable cloning vector. Preferably, the variant sequences are at least as biologically active as the sequences presented herein.

In some preferred embodiments, sequences that are provided that are complementary to the compound or sequences that are capable of hybridizing to the nucleotide sequences of the compounds (including complementary sequences of those presented herein), as well as nucleotide sequences that are complementary to sequences that can hybridize to the nucleotide sequences of the compounds (including complementary sequences of those presented herein). In some preferred embodiments, polynucleotide sequences that are capable of hybridizing to the nucleotide sequences presented herein under conditions of intermediate to maximal stringency are provided.

In some preferred embodiments, nucleotide sequences that can hybridize to the nucleotide sequence of the compound nucleic acid, or the complement thereof, under stringent conditions (e.g., 50° C. and 0.2×SSC) are provided. More preferably, the nucleotide sequences can hybridize to the nucleotide sequence of the compound, or the complement thereof, under more highly stringent conditions (e.g. 65° C. and 0.1× SSC).

In some embodiments, it is desirable to mutate the sequence in order to prepare a compound. Accordingly, in some embodiments, mutants are prepared from the compounds provided herein. In some embodiments, mutations are introduced using synthetic oligonucleotides. These oligonucleotides contain nucleotide sequences flanking the desired mutation sites. Various methods known in the art find use in this embodiment (See e.g., Morinaga et al., Biotechnol., 2:646-649 [1984]; Nelson and Long, Anal. Biochem., 180:147-151 [1989]; and Sarkar and Sommer, Biotechn., 8:404-407 [1990]). However, additional methods find use in the present invention and it is not intended that the present invention be limited to any particular method.

In some preferred embodiments, the sequences used in the methods and compositions described herein is a recombinant sequence (i.e., a sequence that has been prepared using recombinant DNA techniques produced using any suitable method known in the art.

In additional embodiments, the present invention provides vectors comprising the compound, cells comprising the compound, and methods of expressing the compound. In some embodiments, the nucleotide sequences used in the methods and compositions described herein are incorporated into a recombinant replicable vector. In some embodiments, the vector is used to replicate and express the nucleotide sequence, in enzyme form, in and/or from a compatible host cell. In some embodiments, expression is controlled using control sequences (e.g., regulatory sequences). In some embodiments, proteins produced by a host cell by expression of the nucleotide sequence are secreted (i.e., into the growth medium), while in other embodiments, the proteins are contained intracellularly within the host cell. In some embodiments, the coding sequences are designed to include signal sequences which direct secretion of the substance coding sequences through a particular prokaryotic or eukaryotic cell membrane. In further embodiments, polynucleotides are incorporated into a recombinant replicable vector. In additional embodiments, the vector is used to replicate the nucleic acid in a compatible host cell. In preferred embodiments, the vector comprising the polynucleotide sequence is transformed into a suitable host cell. While any suitable host finds use in the present invention, in some preferred embodiments, the hosts are selected from the group consisting of bacterial, yeast, insect, fungal, and mammalian cells.

In some embodiments, compounds and their polynucleotides are expressed by introducing a polynucleotide into a replicable vector, introducing the vector into a compatible host cell, and growing the host cell under conditions which bring about replication of the vector. In some embodiments, the vector is recovered from the host cell.

In additional embodiments, the compound nucleic acid is operatively linked to transcriptional and translational regulatory elements active in the host cell. In some embodiments, the compound nucleic acid also encodes a fusion protein comprising at least one signal sequence (e.g., those derived from the glucoamylase gene from *Schwanniomyces occidentalis*, α-factor mating type gene from *Saccharomyces cerevisiae* and the TAKA-amylase from *Aspergillus oryzae*). In further alternative embodiments, the compound nucleic acid encodes a fusion protein comprising a membrane binding domain.

In some preferred embodiments, the compound is expressed at the desired levels in a host organism using an expression vector. It is contemplated that any expression vector comprising a compound nucleic acid that is capable of expressing the gene encoding the compound nucleic acid in the selected host organism will find use in the present invention. The choice of vector depends upon the host cell into which it is to be introduced. Thus, in some embodiments, the vector is an autonomously replicating vector (i.e., a vector that exists as an episomal entity, the replication of which is independent of chromosomal replication, such as, for example, a plasmid, a bacteriophage or an episomal element, a minichromosome or an artificial chromosome). Alternatively, in some embodiments, the vector integrates into the host cell genome and replicates together with the chromosome.

In some preferred embodiments, the expression vector includes the components of a cloning vector, including but not limited to such components as an element that permits autonomous replication of the vector in the selected host organism and one or more phenotypically detectable markers for selection purposes. In preferred embodiments, the expression vector further comprises control nucleotide sequences encoding a promoter, operator, ribosome binding site, translation initiation signal, and optionally, a repressor gene or one or more activator genes. Additionally, in some embodiments, the expression vector comprises a sequence coding for an amino acid sequence capable of targeting the compound to a host cell organelle such as a peroxisome or to a particular host cell compartment. Such a targeting sequence includes but is not limited to the sequence SKL. For expression under the direction of control sequences, the nucleic acid sequence encoding the compound is operably linked to the control sequences in proper manner with respect to expression.

In some preferred embodiments, the polynucleotide in a vector is operably linked to a control sequence that is capable of providing for the expression of the coding sequence by the host cell (i.e., the vector is an expression vector). In some embodiments, the control sequences are modified (e.g., by the addition of further transcriptional regulatory elements) in order to make the level of transcription directed by the control sequences more responsive to transcriptional modulators. In some preferred embodiments, the control sequences comprise promoters.

In some preferred embodiments of the vectors, the nucleic acid sequence encoding for the compound is operably combined with a suitable promoter sequence. The promoter can be any DNA sequence having transcription activity in the host organism of choice and can be derived from genes that are homologous or heterologous to the host organism. Examples of suitable promoters for directing the transcription of the modified nucleotide sequence, such as compound nucleic acids, in a bacterial host include, but are not limited to the promoter of the lac operon of *E. coli*, the *Streptomyces coelicolor* agarase gene dagA promoters, the promoters of the *Bacillus licheniformis* α-amylase gene (amyL), the aprE promoter of *Bacillus subtilis*, the promoters of the *Bacillus stearothermophilus* maltogenic amylase gene (amyM), the promoters of the *Bacillus amyloliquefaciens* α-amylase gene (amyQ), the promoters of the *Bacillus subtilis* xylA and xylB genes and a promoter derived from a *Lactococcus* sp.-derived promoter including the P170 promoter. When the gene encoding the compound is expressed in a bacterial species such as *E. coli*, a suitable promoter can be selected, for example, from a bacteriophage promoter including a T7 promoter and a phage lambda promoter. For transcription in a fungal species, examples of useful promoters are those derived from the genes encoding the *Aspergillus oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, and *A. nidulans* acetamidase. Examples of suitable promoters for the expression in a yeast species include but are not limited to the Gal 1 and Gal 10 promoters of *Saccharomyces cerevisiae* and the *Pichia pastoris* AOX1 or AOX2 promoters.

Examples of suitable bacterial host organisms are Gram positive species, including, but not limited to members of the *Bacillaceae*, (e.g., *B. subtilis, B. licheniformis, B. lentus, B. brevis, B. stearothennophilus, B. alkalophilus, B. amyloliquefaciens, B. coagulans, B. lautus, B. megaterium* and *B. thuringiensis*), *Streptomyces* species (e.g., *S. murinus* and *S. lividans*) lactic acid bacteria (e.g., *Lactococcus* spp. such as *Lactococcus lactis; Lactobacillus* spp. including *Lactobacillus reuteri; Leuconostoc* spp.; *Pediococcus* spp.; and *Streptococcus* spp. Alternatively, strains of Gram-negative species belonging to *Enterobacteriaceae* (e.g., *E. coli*) or members of the *Pseudomonadaceae* find use in the present invention.

In some embodiments, a suitable yeast host organism is selected from various biotechnologically useful yeasts species, including but not limited to *Pichia* sp., *Hansenula* sp or *Kluyveromyces, Yarrowinia, Saccharomyces* (e.g., *Saccharomyces cerevisiae*), *Schizosaccharomyce* (e.g., *S. pombe*). In some embodiments, strains of the methylotrophic yeast species *Pichia pastoris* are used as the host organism, while in other embodiments, the host organism is a *Hansenula* species. Suitable host organisms among filamentous fungi include species of *Aspergillus* (e.g., *A. niger, A. oryzae, A. tubigensis, A. awamori* and *Aspergillus nidulans*). Alternatively, strains of *Fusarium* species (e.g. *F. oxysporum*) and *Rhizomucor* (e.g., *Rhizomucor miehei*) find used as the host organism. Additional suitable strains include, but are not limited to *Thermomyces* and *Mucor* species.

In some preferred embodiments, host cells comprising polynucleotides are used to express polypeptides, such as the compounds disclosed herein, fragments, homologues, variants or derivatives thereof. Host cells are cultured under suitable conditions which allow expression of the proteins. In some embodiments, expression of the polypeptides is constitutive (i.e., the peptides are continually produced), while in other embodiments, expression is inducible. In the case of inducible expression, protein production is initiated when required by addition of an inducer substance to the culture medium (e.g., dexamethasone or IPTG). Polypeptides can be extracted from host cells by a variety of techniques known in the art, including enzymatic, chemical, and/or osmotic lysis and physical disruption. Indeed, it is not intended that the present invention be limited to any particular means of harvesting expressed polypeptides.

In alternative embodiments, polypeptides are produced recombinantly in any suitable (including commercially available) in vitro cell-free system, such as the TnT™ (Promega) rabbit reticulocyte system.

In additional preferred embodiments, the present invention provides cosmetic and/or pharmaceutical compositions comprising at least one polypeptide or peptide, as set forth herein, and a physiologically acceptable carrier or excipient. Preferably, the compound is present in an amount of about 0.0001% to about 5% by weight, based on the total weight of the composition. Also preferably, the compound is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup. Preferably, the carrier is at least compound selected from the group consisting of water, propylene glycol, ethanol, propanol, glycerol, butylene glycol and polyethylene glycol.

In some liposomal embodiments, the liposomes comprise water and one or more ingredients capable of forming lipid bilayer vesicles that can hold one or more functional or active ingredient(s). Non-limiting examples of ingredients capable of forming lipid bilayer vesicles include: phospholipids, hydrogenated phosphatidylcholine, lecithin, cholesterol and sphingolipids. Non-limiting examples of functional or active ingredients that can be delivered via liposomes include: vitamins and their derivatives, antioxidants, proteins and peptides, keratolytic agents, bioflavinoids, terpenoids, phytochemicals, and extracts of plant, marine or fermented origin. In a preferred embodiment, the composition further comprises a skin care or hair care active. Active ingredients can include any of a wide variety of ingredients such as are known in the art. (See e.g., *McCutcheon's Functional Materials*, North American and International Editions, (2003), published by MC Publishing Co.). Preferably, such actives include but are not limited to antioxidants, such as tocopheryl and ascorbyl derivatives, bioflavinoids, terpenoids, synthetics and the like, vitamins and vitamin derivatives, hydroxyl- and polyhydroxy acids and their derivatives, such as AHAs and BHAs and their reaction products, peptides and polypeptides and their derivatives, such as glycopeptides and lipophilized peptides, heat shock proteins and cytokines, enzymes and enzymes inhibitors and their derivatives, such as proteases, MMP inhibitors, catalases, glucose oxidase and superoxide dismutase, amino acids and their derivatives, bacterial, fungal and yeast fermentation products and their derivatives, including mushrooms, algae and seaweed and their derivatives, phytosterols and plant and plant part extracts and their derivatives and phospholipids and their derivatives, anti-dandruff agents such as zinc pyrithione and delivery systems containing them, as provided herein and/or known in the art.

In some preferred embodiments, the skin care active is selected from the group consisting of a Vitamin B3 component, panthenol, Vitamin E, Vitamin E acetate, retinol, retinyl propionate, retinyl palmitate, retinoic acid, Vitamin C, theobromine, alpha-hydroxyacid, farnesol, phytrantriol, salicylic acid, palmityl peptapeptide-3 and mixtures thereof. In some preferred embodiments, the Vitamin B3 component is niacinamide. In some embodiments, the compositions provided herein comprise a skin care active at a level from about 0.0001% to about 20%, preferably from about 0.001% to about 5%, more preferably from about 0.01% to about 2%, by weight.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Suitable esters of nicotinic acid include nicotinic acid esters of $C_1$-$C_{22}$, preferably $C_1$-$C_{16}$, more preferably $C_1$-$C_6$ alcohols. In these embodiments, the alcohols are suitably straight-chain or branched chain, cyclic or acyclic, saturated or unsaturated (including aromatic), and substituted or unsubstituted. The esters are preferably non-vasodilating.

Non-vasodilating esters of nicotinic acid include tocopherol nicotinate and inositol hexanicotinate; tocopherol nicotinate are preferred. A more complete description of vitamin $B_3$ compounds is provided in WO 98/22085. Preferred vitamin $B_3$ compounds include niacinamide and tocopherol nicotinate.

In additional embodiments, the skin care active comprises at least one retinoid. The retinoid is preferably retinol, retinol esters (e.g., $C_2$-$C_{22}$ alkyl esters of retinol, including retinyl palmitate, retinyl acetate, retinyl proprionate), retinal, and/or retinoic acid (including all-trans retinoic acid and/or 13-cis-retinoic acid), more preferably retinoids other than retinoic acid. These compounds are well known in the art and are commercially available from a number of sources (e.g., Sigma and Boehringer Mannheim). Preferred retinoids include retinol, retinyl palmitate, retinyl acetate, retinyl proprionate, retinal, retinoic acid and combinations thereof. More preferred are retinol, retinoic propionate, retinoic acid and retinyl palmitate. In some embodiments, the retinoid is included as a substantially pure material, while in other embodiments, it is provided as an extract obtained by suitable physical and/or chemical isolation from natural (e.g., plant) sources. When a retinoid is included in the compositions herein, it preferably comprises from about 0.005% to about 2%, preferably from about 0.01% to about 1% retinoid. Retinol is preferably used in an amount of from about 0.01% to about 0.15%; retinol esters are preferably used in an amount of from about 0.01% to about 2% (e.g., about 1%).

In some embodiments, the compositions of the present invention comprise safe and effective amounts of a dermatologically acceptable carrier that is suitable for topical application to the skin or hair within which the essential materials and optional other materials are incorporated to enable the essential materials and optional components to be delivered to the skin or hair at an appropriate concentration. Thus, in some embodiments, the carrier acts as a diluent, dispersant, solvent or the like for the essential components, ensuring that these components can be applied and distributed evenly over the selected target at an appropriate concentration.

In further embodiments, an effective amount of one or more compounds described herein is also be included in compositions to be applied to keratinous materials such as nails and hair, including but not limited to those useful as hair spray compositions, hair styling compositions, hair shampooing and/or conditioning compositions, compositions applied for the purpose of hair growth regulation and compositions applied to the hair and scalp for the purpose of treating seborrhoea, dermatitis and/or dandruff.

In yet additional embodiments, an effective amount of one or more compounds described herein is included in compositions suitable for topical application to the skin or hair. These compositions are provided in any suitable form, including but not limited to creams, lotions, gels, suspensions dispersions, microemulsions, nanodispersions, microspheres, hydrogels, emulsions (e.g., oil-in-water and water-in-oil, as well as multiple emulsions), and multilaminar gels and the like (See e.g., Schlossman et al., *The Chemistry and Manufacture of Cosmetics, [*1998], incorporated by reference, herein). In some embodiments, the compositions are formulated as aqueous or silicone compositions, while in other embodiments they are formulated as emulsions of one or more oil phases in an aqueous continuous phase (or an aqueous phase in an oil phase).

The type of carrier utilized in the present invention depends on the type of product form desired for the composition. The carrier can be solid, semi-solid or liquid. Suitable carriers include liquids, semi-solids (e.g., creams, lotions, gels, sticks, ointments, and pastes), sprays and mousses. Preferably the carrier is in the form of a lotion, cream or a gel, more preferably one which has a sufficient thickness or yield point to prevent the particles from sedimenting. In some embodiments, the carrier is inert, while in other embodiments it provides dermatological benefits. In some embodiments, the carrier is applied directly to the skin and/or hair, while in other embodiments, it is applied via a woven or non-woven wipe or cloth. In yet other embodiments, it is in the form of a patch, mask or wrap. In still further embodiments, it is aerosolized or otherwise sprayed or pumped onto the skin and/or hair. The carrier chosen is physically and chemically compatible with the essential components described herein, and should not unduly impair stability, efficacy or other use benefits associated with the compositions of the present invention.

Preferred carriers contain a dermatologically acceptable, hydrophilic diluent. Suitable hydrophilic diluents include water, organic hydrophilic diluents such as $C_2$-$C_{10}$, preferably $C_2$-$C_6$, preferably, $C_3$-$C_6$ monohydric alcohols and low molecular weight glycols and polyols, including propylene glycol, polyethylene glycol polypropylene glycol, glycerol, butylene glycol, 1,2,4-butanetriol, sorbitol esters, 1,2,6-hexametriol, pentylene glycol, hexylene glycol, sorbitol esters, ethoxylated ethers, propoxylated ethers, and combinations thereof. The diluent is preferably liquid. Water is a preferred diluent. The composition preferably comprises at least about 20% of the hydrophilic diluent.

In some embodiments, suitable carriers also comprise an emulsion comprising a hydrophilic phase, especially an aqueous phase, and a hydrophobic phase (e.g., a lipid, oil or oily material). As well known to those skilled in the art, the hydrophilic phase is dispersed in the hydrophobic phase, or vice versa, to form respectively hydrophilic or hydrophobic dispersed and continuous phases, depending on the composition of ingredients. The term "dispersed phase" is a term well-known to one skilled in the art of emulsion technology, used in reference to the phase which exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions typically comprise from about 1% to about 60% (preferably about 1% to about 30%) of the dispersed hydrophobic phase and from about 1% to about 99% (preferably from about 10% to about 90%) of the continuous hydrophilic phase, while water-in-oil emulsions typically comprise from about 1% to about 98% (preferably from about 40% to about 90%) of the dispersed hydrophilic phase and from about 1% to about 50% (preferably about 1% to about 30%) of the continuous hydrophobic phase.

In further embodiments, the carrier also includes one or more components that facilitate penetration through the upper stratum corneum barrier to the lower levels of the skin. Examples of penetration enhancers include, but are not limited to, propylene glycol, azone, ethoxydiglycol, dimethyl isosorbide, urea, ethanol and dimethyl sulfoxide, as well as microemulsions, liposomes and nanoemulsions.

In some additional embodiments, the compositions of the present invention comprise humectants which are preferably present at a level of from about 0.01% to about 20%, preferably from about 0.1% to about 15% and preferably from about 0.5% to about 10%. Preferred humectants include, but are not limited to, compounds selected from polyhydric alcohols, sorbitol, glycerol, urea, betaine, D-panthenol, DL-panthenol, calcium pantothenate, royal jelly, panthetine, pantotheine, panthenyl ethyl ether, pangamic acid, pyridoxin, pantoyl lactose Vitamin B complex, sodium pyrrolidone carboxylic acid, hexane-1,2,6,-triol, guanidine or its derivatives, and mixtures thereof.

Suitable polyhydric alcohols for use herein include, but are not limited to polyalkylene glycols and preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, pentylene glycol, hexylene glycol, butylene glycol (e.g., 1,3-butylene glycol), hexane triol (e.g., 1,2,6-hexanetriol), trimethylol propane, neopentyl glycol, glycerine, ethoxylated glycerine, propane-1,3 diol, propoxylated glycerine and mixtures thereof. The alkoxylated derivatives of any of the above polyhydric alcohols are also suitable for use herein. Preferred polyhydric alcohols of the present invention are selected from glycerine, butylene glycol, propylene glycol, pentylene glycol, hexylene glycol, dipropylene glycol, polyethylene glycol, hexane triol, ethoxylated glycerine and propoxylated glycerine and mixtures thereof.

Suitable humectants useful herein are sodium 2-pyrrolidone-5-carboxylate (NaPCA), guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; betaine, panthenol and derivatives thereof; and mixtures thereof.

In some embodiments, at least part (up to about 5% by weight of composition) of a humectant is incorporated into the compositions of the present invention in the form of an admixture with a particulate cross-linked hydrophobic acrylate or methacrylate copolymer, itself preferably present in an amount of from about 0.1% to about 10%, which can be added either to the aqueous or disperse phase. This copolymer is particularly valuable for reducing shine and controlling oil while helping to provide effective moisturization benefits and is described in further detail in WO96/03964, incorporated herein by reference.

In some embodiments, the oil-in-water and water-in-oil compositions of the present invention comprise from about 0.05% to about 20%, preferably from about 1% to about 15%, preferably from about 2% to about 10%, preferably from about 2% to about 5% of a dermatologically acceptable emollient. Emollients tend to lubricate the skin, increase the smoothness and suppleness of the skin, prevent or relieve dryness of the skin and/or protect the skin. Emollients are typically water-immiscible, oily or waxy materials and emollients can confer aesthetic properties to a topical composition. A wide variety of suitable emollients are known (See e.g., Sagarin, *Cosmetics, Science and Technology,* 2nd Edition, Vol. 1, pp. 32-43 [1972]; and WO 00/24372), and find use herein, contains numerous examples of materials suitable as emollients. Additional emollients include, but are not limited to the following:

i) Straight and branched chain hydrocarbons having from about 7 to about 40 carbon atoms, such as mineral oils, dodecane, squalane, cholesterol, hydrogenated polyisobutylene, isohexadecane, isoeicosane, isooctahexacontane, isohexapentacontahectane, and the $C_7$-$C_{40}$ isoparaffins, which are $C_7$-$C_{40}$ branched hydrocarbons. Suitable branched chain hydrocarbons for use herein are selected from isopentacontaoctactane, petrolatum and mixtures thereof;

ii) $C_1$-$C_{30}$ fatty acid esters of $C_1$-$C_{30}$ carboxylic acids, $C_{12-15}$ alkyl benzoates and of $C_2$-$C_{30}$ dicarboxylic acids, e.g. isononyl isononanoate, isostearyl neopentanoate, isodecyl octanoate, isodecyl isononanoate, tridecyl isononanoate, myristyl octanoate, octyl pelargonate, octyl isononanoate, myristyl myristate, myristyl neopentanoate, myristyl octanoate, isopropyl myristate, myristyl propionate, isopropyl stearate, isopropyl isostearate, methyl isostearate, behenyl behenate, dioctyl maleate, diisopropyl adipate, and diisopropyl dilinoleate and mixtures thereof also find use in the present invention;

iii) $C_1$-$C_{30}$ mono- and poly-esters of sugars and related materials. These esters are derived from a sugar or polyol moiety and one or more carboxylic acid moieties. Depending on the constituent acid and sugar, these esters can be in either liquid or solid form at room temperature. Examples include: glucose tetraoleate, the galactose tetraesters of oleic acid, the sorbitol tetraoleate, sucrose tetraoleate, sucrose pentaoleate, sucrose hexaoleate, sucrose heptaoleate, sucrose octaoleate, sorbitol hexaester. Other materials include cottonseed oil or soybean oil fatty acid esters of sucrose. Other examples of such materials are described in WO 96/16636, incorporated by reference herein;

iv) Vegetable oils and hydrogenated vegetable oils. Examples of vegetable oils and hydrogenated vegetable oils include safflower oil, grapeseed oil, coconut oil, cottonseed oil, menhaden oil, palm kernel oil, palm oil, peanut oil, soybean oil, rapeseed oil, linseed oil, rice bran oil, pine oil, nut oil, sesame oil, sunflower seed oil, partially and fully hydrogenated oils from the foregoing sources and mixtures thereof;

v) Soluble or colloidally-soluble moisturizing agents. Examples include hyaluronic acid and chondroitin sulfate.

In some embodiments, the compositions of the present invention contain an emulsifier and/or surfactant, generally to help disperse and suspend the disperse phase within the continuous aqueous phase. A surfactant may also be useful if the product is intended for skin or hair cleansing. For convenience hereinafter, "emulsifiers" are encompassed by the term "surfactants." Thus, as used herein, the term "surfactant(s)" refers to surface active agents, whether used as emulsifiers or for other surfactant purposes such as skin cleansing. Known, including conventional surfactants find use in the present invention, provided that the selected agent is chemically and physically compatible with essential components of the composition and provides the desired characteristics (See e.g., WO 00/24372). Suitable surfactants include non-silicone derived materials, silicone-derived materials, and mixtures thereof.

In further embodiments, the compositions of the present invention comprise preferably from about 0.05% to about 30%, more preferably from about 0.5% to 15%, and most preferably from about 1% to 10% of a surfactant or mixture of surfactants. The exact surfactant or surfactant mixture chosen depends upon the pH of the composition, the other components present and the desired final product aesthetics.

Among the nonionic surfactants that are useful herein are those that can be broadly defined as condensation products of long chain alcohols (e.g., $C_{8-30}$ alcohols), with sugar or starch polymers (e.g., glycosides). Other useful nonionic surfactants include the condensation products of alkylene oxides with fatty acids (i.e., alkylene oxide esters of fatty acids). These materials have the general formula $RCO(X)_nOH$ wherein R is a $C_{10-30}$ alkyl group, X is $—OCH_2CH_2—$(i.e., derived from ethylene glycol or oxide) or $—OCH_2CHCH_3—$(i.e., derived from propylene glycol or oxide) and n is an integer from about 6 to about 200. Other nonionic surfactants are the condensation products of alkylene oxides with 2 moles of fatty acids (i.e., alkylene oxide diesters of fatty acids). These materials have the general formula $RCO(X)_nOOCR$ wherein R is a $C_{10-30}$ alkyl group, X is $—OCH_2CH_2—$( i.e., derived from ethylene glycol or oxide) or $—OCH_2CHCH_3—$(i.e., derived from propylene glycol or oxide) and n is an integer from about 6 to about 100. In some embodiments, an emulsifier for use herein is preferably a fatty acid ester blend based on a mixture of sorbitan fatty acid ester and sucrose fatty acid ester, especially a blend of sorbitan stearate and sucrose cocoate. Further suitable examples include a mixture of cetearyl alcohols and cetearyl glucosides. However, it is not intended that the present invention be limited to any particular emulsifier, as various suitable emulsifiers are known in the art.

In additional embodiments, the hydrophilic surfactants useful herein alternatively or additionally include any of a wide variety of cationic, anionic, zwitterionic, and amphoteric surfactants such as are known in the art (See, e.g., *McCutcheon's, Emulsifiers and Detergents*, North American and International Editions, MC Publishing Co. [2003]; U.S. Pat. Nos. 5,011,681 4,421,769; and 3,755,560).

A variety of anionic surfactants are also useful herein (See e.g., U.S. Pat. No. 3,929,678). Exemplary anionic surfactants include, but are not limited to alkoyl isethionates (e.g., $C_{12}$-$C_{30}$), alkyl and alkyl ether sulfates and salts thereof, alkyl and alkyl ether phosphates and salts thereof, alkyl methyl taurates (e.g., $C_{12}$-$C_{30}$), and soaps (e.g., substituted alkylamine and alkali metal salts, e.g., sodium or potassium salts) of fatty acids.

Amphoteric and zwitterionic surfactants are also useful herein. Examples of preferred amphoteric and zwitterionic surfactants which find use in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilizing group (e.g., carboxy, sulfonate, sulfate, phosphate, or phosphonate). Examples, include but are not limited to alkyl imino acetates and iminodialkanoates and aminoalkanoates, imidazolinium and ammonium derivatives. Other suitable amphoteric and zwitterionic surfactants are those selected from the group consisting of betaines, sultaines, hydro-xysultaines, and branched and unbranched alkanoyl sarcosinates, and mixtures thereof.

In further embodiments, some emulsions of the present invention include a silicone containing emulsifier or surfactant. A wide variety of silicone emulsifiers find use herein. These silicone emulsifiers are typically organically modified organopolysiloxanes, also known to those skilled in the art as silicone surfactants. Useful silicone emulsifiers include, but are not limited to dimethicone copolyols. These materials are polydimethyl siloxanes which have been modified to include polyether side chains such as polyethylene oxide chains, polypropylene oxide chains, mixtures of these chains and polyether chains containing moieties derived from both ethylene oxide and propylene oxide. Other examples include alkyl-modified dimethicone copolyols (i.e., compounds which contain $C_2$-$C_{30}$ pendant side chains). Still other useful dimethicone copolyols include materials having various cationic, anionic, amphoteric, and zwitterionic pendant moieties.

In some embodiments, the compositions of the present invention comprise at least one polymeric thickening agent. The polymeric thickening agents useful herein preferably have a number average molecular weight of greater than about 20,000, more preferably greater than about 50,000, and most preferably greater than about 100,000. In some embodiments, the compositions of the present invention comprise from about 0.01% to about 10%, preferably from about 0.1% to about 8% and more preferably from about 0.2% to about 5% by weight of the composition of the polymeric thickening agent or mixtures thereof.

Preferred polymer thickening agents for use herein include, but are not limited to non-ionic thickening agents and anionic thickening agents or mixtures thereof. Suitable nonionic thickening agents include, but are not limited to polyacrylamide polymers, crosslinked poly(N-vinylpyrrolidones), polysaccharides, natural or synthetic gums, polyvinylpyrrolidone and polyvinylalcohol. Suitable anionic thickening agents include, but are not limited to acrylic acid/ethyl acrylate copolymers, carboxyvinyl polymers and crosslinked copolymers of alkyl vinyl ethers and maleic anhydride. Commercially available thickeners (e.g., Carbopol; Noveon) find use in some embodiments of the present invention. Suitable Carbopol resins may be hydrophobically modified, and other suitable resins are described in WO98/22085, or mixtures thereof.

In some embodiments, the present compositions comprise at least one silicone oil phase. Silicone oil phase(s) generally comprises from about 0.1% to about 20%, preferably from about 0.5% to about 10%, and more preferably from about 0.5% to about 5%, of the composition. The silicone oil phase preferably comprises one or more silicone components.

In some embodiments, silicone components are fluids, including straight chain, branched and cyclic silicones. Suitable silicone fluids useful herein include silicones inclusive of polyalkyl siloxane fluids, polyaryl siloxane fluids, cyclic and linear polyalkylsiloxanes, polyalkoxylated silicones, amino and quaternary ammonium modified silicones, polyalkylaryl siloxanes or a polyether siloxane copolymer and mixtures thereof. Volatile, as well as non-volatile silicone fluids find use herein. Silicone fluids generally have an average molecular weight of less than about 200,000. In preferred embodiments, suitable silicone fluids have a molecular weight of about 100,000 or less, preferably about 50,000 or less, and more preferably about 10,000 or less. Preferably the silicone fluid is selected from silicone fluids having a weight average molecular weight in the range from about 100 to about 50,000 and preferably from about 200 to about 40,000. Typically, silicone fluids have a viscosity ranging from about 0.65 to about 600,000 $mm^2s^{-1}$, preferably from about 0.65 to about 10,000 $mm^2.s^{-1}$ at 25° C. The viscosity can be measured by means of a glass capillary viscometer as set forth in Dow Coming Corporate Test Method CTM0004, Jul. 29, 1970. Suitable polydimethyl siloxanes that can be used herein include commercially available compounds (e.g., from the General Electric Company and Dow Corning). Also useful are essentially non-volatile polyalkylarylsiloxanes, for example, polymethyl-phenylsiloxanes, having viscosities of about 0.65 to 30,000 $mm^2s^{-1}$ at 25° C. (General Electric Company or from Dow Coming). Cyclic polydimethylsiloxanes suitable for use herein are those having a ring structure incorporating from about 3 to about 7 $(CH_3)_2SiO$ moieties, preferably about 5 or more.

In additional embodiments, silicone gums find use herein. In some preferred embodiments, a silicone oil phase comprises a silicone gum or a mixture of silicones including the silicone gum. Typically, silicone gums have a viscosity at 25° C. in excess of about 1,000,000 $mm^2s^{-1}$. The silicone gums include dimethicones as known in the art (See e.g., U.S. Pat. No. 4,152,416; and Noll, *Chemistry and Technology of Silicones*, Academic Press, New York [1968]). Silicone gums such as those described in General Electric Silicone Rubber Product Data Sheets SE 30, SE 33, SE 54 and SE 76, also find use in the present invention. Specific examples of silicone gums include polydimethylsiloxane, (polydimethylsiloxane) (methylvinylsiloxane) copolymer, poly(dimethylsiloxane) (diphenyl)(methylvinylsiloxane) copolymer and mixtures thereof. Preferred silicone gums for use herein are silicone gums having a molecular weight of from about 200,000 to about 4,000,000 selected from dimethiconol, dimethicone copolyol, dimethicone and mixtures thereof.

In some embodiments, a silicone phase herein preferably comprises a silicone gum incorporated into the composition as part of a silicone gum-fluid blend. When the silicone gum is incorporated as part of a silicone gum-fluid blend, the silicone gum preferably constitutes from about 5% to about 40%, especially from about 10% to 20% by weight of the silicone gum-fluid blend. Suitable silicone gum-fluid blends herein are mixtures consisting essentially of:

(i) a silicone having a molecular weight of from about 200,000 to about 4,000,000 selected from dimethiconol, fluorosilicone and dimethicone and mixtures thereof; and (ii) a carrier which is a silicone fluid, the carrier having a viscosity from about 0.65 $mm^2s^{-1}$ to about 100 $mm^2s^{-1}$, wherein the ratio of i) to ii) is from about 10:90 to about 20:80 and wherein said silicone gum-based component has a final viscosity of from about 100 $mm^2s^{-1}$ to about 100,000 $mm^2s^{-1}$, preferably from 500 $mm^2s^{-1}$ to about 10,000 $mm^2s^{-1}$.

Further silicone components suitable for use in a silicone oil phase herein include crosslinked polyorganosiloxane polymers, optionally dispersed in a fluid carrier. In general, when present the crosslinked polyorganosiloxane polymers, together with its carrier (if present) comprises from about 0.1% to about 20%, preferably from about 0.5% to about 10%, and more preferably from about 0.5% to about 5% of the composition. Such polymers comprise polyorganosiloxane polymers crosslinked by a crosslinking agent (See e.g., WO98/22085). Examples of suitable polyorganosiloxane polymers for use herein include, but are not limited to methyl vinyl dimethicone, methyl vinyl diphenyl dimethicone and methyl vinyl phenyl methyl diphenyl dimethicone.

Another class of silicone components suitable for use in a silicone oil phase herein includes polydiorganosiloxane-polyoxyalkylene copolymers containing at least one polydiorganosiloxane segment and at least one polyoxyalkylene segment (See e.g., WO98/22085). Suitable polydiorganosiloxane-polyalkylene copolymers are available commercially under the tradenames BELSIL® from Wacker-Chemie GmbH. A particularly preferred copolymer fluid blend for use herein includes Dow Corning DC3225C which has the CTFA designation Dimethicone/Dimethicone copolyol.

In further embodiments, compositions of the present invention comprise an organic sunscreen. In some embodiments, suitable sunscreens have UVA absorbing properties, while others have UVB absorbing properties, and still others comprise a mixture thereof. The exact amount of the sunscreen active varies, depending upon the desired Sun Protection Factor (i.e., the "SPF") of the composition, as well as the desired level of UV protection. SPF is a commonly used measure of photoprotection of a sunscreen against erythema. The SPF is defined as a ratio of the ultraviolet energy required to produce minimal erythema on protected skin to that required to produce the same minimal erythema on unprotected skin in the same individual. Amounts of the sunscreen used are preferably from about 2% to about 20%, and more preferably from about 4% to about 14%. Suitable sunscreens include, but are not limited to those approved for use in the United States, Japan, Europe and Australia. The compositions of the present invention preferably comprise an SPF of about 2 to about 30, preferably about 4 about 30, and more preferably about 4 to about 15.

In some embodiments, the compositions of the present invention may one or more UVA absorbing sunscreen actives that absorb UV radiation having a wavelength of from about 320 nm to about 400 nm. Suitable UVA absorbing sunscreen actives include, but are not limited to dibenzoylmethane (See e.g., Lowe and Shaath (eds.), *Sunscreens: Development, Evaluation, and Regulatory Aspects*, Marcel Dekker, Inc.) derivatives, anthranilate derivatives such as methylanthranilate and homomethyl, 1-N-acetylanthranilate, and mixtures thereof. The UVA absorbing sunscreen active is preferably present in an amount sufficient to provide broad spectrum UVA protection either independently, or in combination with, other UV protective actives which may be present in the composition.

Suitable UVA sunscreen actives include dibenzoylmethane sunscreen actives and their derivatives. They include, but are not limited to, those selected from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'-methoxydibenzoylmethane, 2-methyl-5-isopropyl-4'-methoxydibenzoylmethane, 2-methyl-5-tert-butyl4'-methoxy-dibenzoylmethane, 2,4-dimethyl-4'-methoxydibenzoylmethane, 2,6-dimethyl-4'-tert-butyl-4'methoxydibenzoylmethane, and mixtures thereof. Preferred dibenzoyl sunscreen actives include those selected from 4-(1,1-dimethylethyl)-4'-methoxydibenzoylmethane, 4-isopropyldibenzoylmethane, and mixtures thereof. A preferred sunscreen active is 4-(1,1-dimethylethyl)-4'-methoxydibenzoylmethane.

The sunscreen active 4-(1,1-dimethylethyl)-4'-methoxydibenzoylmethane, which is also known as butyl methoxydibenzoylmethane or "avobenzone," is commercially available under the names of Parsol® 1789 from Givaudan Roure (International) S. A., and Eusolex® 9020 from Merck & Co., Inc. The sunscreen 4-isoproplydibenzoylmethane, which is also known as isopropyldibenzoylmethane, is commercially available from Merck under the name of Eusolex® 8020.

In some embodiments, the compositions of the present invention further include one or more UVB sunscreen actives that absorb(s) UV radiation having a wavelength of about 290 nm to about 320 nm. The compositions comprise an amount of the UVB sunscreen active that is safe and effective in providing UVB protection either independently, or in combination with, other UV protective actives which may be present in the compositions. The compositions comprise from about 0.1% to about 20%, preferably from about 0.1% to about 12%, and more preferably from about 0.5% to about 8% by weight, of each UVB absorbing organic sunscreen, or as mandated by the relevant regulatory authority(s).

A variety of UVB sunscreen actives are suitable for use herein (See e.g., U.S. Pat Nos. 5,087,372; 5,073,371; 5,073,372; 4,937,370; and 4,999,186). Preferred UVB sunscreen actives are selected from 2-ethylhexyl-2-cyano-3,2-ethylhexyl N,N-dimethyl-p-aminobenzoate, p-aminobenzoic acid, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, 3-diphenylacrylate, 2-phenyl-benzimidazole-5-sulphonic acid (PBSA), cinnamate esters and their derivatives such as 2-ethylhexyl-p-methoxycinnamate, salicylate esters and their derivatives such as triethanolamine salicylate, ethylhexyl salicylate, octyldimethyl para-aminobenzoic acid, camphor derivatives and their derivatives, and mixtures thereof. Preferred organic sunscreen actives include 2-ethylhexyl-2-cyano-3,3-diphenylacrylate, 2-phenyl-benzimidazole-5-sulphonic acid (PBSA), octyl-p-methoxycinnamate, and mixtures thereof. Salt and acid neutralized forms of the acidic sunscreens are also useful herein.

In some embodiments, at least one agent is added to any of the compositions useful in the present invention to stabilize the UVA sunscreen to prevent it from photo-degrading on exposure to UV radiation and thereby maintaining its UVA protection efficacy. A wide range of compounds are reported to have these stabilizing properties and should be chosen to complement both the UVA sunscreen and the composition as a whole (See e.g., U.S. Pat. Nos. 5,972,316; 5,968,485; 5,935,556; 5,827,508; and WO 00/06110). Preferred examples of stabilizing agents for use in the present invention include 2-ethylhexyl-2-cyano-3,3-diphenylacrylate, ethyl-2-cyano-3, 3-diphenylacrylate, 2-ethylhexyl-3,3-diphenylacrylate, ethyl-3,3-bis(4-methoxyphenyl)acrylate, diethylhexyl 2,6 napthalate and mixtures thereof (Symrise Chemical Company).

In some embodiments, at least one agent is added to any of the compositions useful in the present invention to improve the skin substantivity of those compositions, particularly to enhance their resistance to being washed off by water or rubbed off. Examples include, but are not limited to, acrylates/$C_{12-22}$ alkylmethacrylate copolymer, acrylate/acrylate copolymer, dimethicone, dimethiconol, graft-copoly (dimethylsiloxane/i-butyl methacrylate), lauryl dimethicone, PVP/Hexadecane copolymer, PVP/Eicosene copolymer, tricontanyl PVP and trimethoxysiloxysilicate.

In addition to organic sunscreens, in some embodiments, the compositions of the present invention additionally comprise inorganic physical sunblocks (See e.g., TFA International Cosmetic Ingredient Dictionary, $6^{th}$ Edition, pp. 1026-28 and 1103 [1995]; Sayre et al., J. Soc. Cosmet. Chem., 41:103-109 [1990]; and Lowe et al., supra). Preferred inorganic physical sunblocks include zinc oxide and titanium dioxide and mixtures thereof.

When used in preferred embodiments, the physical sunblocks are present in an amount such that the present compositions are transparent on the skin (i.e., non-whitening), preferably from about 0.5% to about 20%, preferably from about 0.5% to about 10%, and more preferably from about 0.5% to 5% by weight. When titanium dioxide is used, it can have an anatase, rutile or amorphous structure. Manufacturers of micronized grade titanium dioxide and zinc oxide for sunscreen use include, but are not limited to Tayca Corporation, Uniqema, Shinetsu Chemical Corporation, Kerr-McGee, Nanophase, Nanosource, Sachtleben, Elementis, and BASF Corporation, as well as their distribution agents and those companies that further process the material for sunscreen use. Physical sunblock particles (e.g., titanium dioxide and zinc oxide) can be uncoated or coated with a variety of materials including but not limited to amino acids, aluminum compounds such as alumina, aluminum stearate, aluminum laurate, and the like; carboxylic acids and their salts (e.g., stearic acid and its salts); phospholipids, such as lecithin; organic silicone compounds; inorganic silicone compounds such as silica and silicates and mixtures thereof.

In some preferred embodiments, the composition of the present invention also include preservatives. Such preservatives include, but are not limited to pentylene glycol, ethylene diamine tetra acetate (EDTA) and its salts, chlorhexidine (and its diacetate, dihydrochloride, digluconate derivatives), 1,1,1-trichloro-2-methyl-2-propanol, parachloro metaxylenol, polyhexamethylenebiguanide hydrochloride, dehydroacetic acid, diazolidinyl urea, 2,4-dichlorobenzyl alcohol, 4,4-dimethyl-1,3-oxazolidine, formaldehyde, glutaraldehyde, dimethylidantoin, imidazolidinyl urea, 5-Chloro-2-methyl-4-isothiazolin-3-one, ortho-phenylphenol, 4-hydroxybenzoic acid ("paraben") and its methyl-, ethyl-, propyl-, isopropyl-, butyl-, isobutyl-esters, trichlosan, 2-phenoxyethanol, phenyl mercuric acetate, quaternium-15, salycilate, salicylic acid and its saltssorbic acid and its salts, iodopropanyl butylcarbamate zinc pyrithione, benzyl alcohol, 5-bromo-5nitro-1,3-dioxane, 2-bromo-2-nitropropane-1,3-diol, benzoic acid and its salts, sulfites, bisulfites, and benzalkonium chloride.

A variety of optional ingredients such as neutralizing agents, perfumes and perfume solubilizing agents, and coloring agents, also find use in some of the compositions herein. It is preferred that any additional ingredients enhance the skin softness/smoothness benefits of the product. In addition it is preferred that any such ingredients do not negatively impact the aesthetic properties of the product.

Neutralizing agents suitable for use in neutralizing acidic group containing hydrophilic gelling agents herein include sodium hydroxide, potassium hydroxide, ammonium hydroxide, monoethanolamine, diethanolamine, amino methyl propanol, tris-buffer and triethanolamine.

Other optional materials that find use in the present invention include any of the numerous functional and/or active ingredients known to those skilled in the art (See e.g., *McCutcheon's Functional Materials*, North American and International Editions, MC Publishing Co. [2003]) Non-limiting examples include keratolytic agents; soluble or colloidally-soluble moisturizing agents such as hyaluronic acid and chondroitin sulfate; vitamins such as vitamin A, vitamin C, vitamin E, vitamin K and derivatives thereof and building blocks thereof; phytantriol; fatty alcohols such as dodecatrienol; alpha and beta hydroxyacids; aloe vera; sphingosines and phytosphingosines, cholesterol; skin whitening agents; N-acetyl cysteine; coloring agents; Examples of alpha hydroxy acids include glycolic acid, lactic acid, malic acid, and citric acid (whether derived synthetically or from natural sources and whether used alone or in combination) and their esters or relevant buffered combinations. Other examples of alpha-hydroxy acids include: alpha-hydroxy ethanoic acid, alpha-hydroxyoctanoic acid, alpha-hydroxycaprylic acid, and hydroxycaprylic acid. Preferred examples of alpha hydroxy acids include glycolic acid and lactic acid. It is preferred that alpha hydroxy acids are used in levels of up to about 10%.

Optional materials include pigments that, where water-insoluble, contribute to and are included in the total level of oil phase ingredients. Pigments suitable for use in the compositions of the present invention can be organic and/or inorganic. Also included within the term "pigment" are materials having a low color or luster, such as matte finishing agents, light scattering agents, and formulation aids such as micas, seracites, and carbonate salts. Further examples of suitable pigments include titanium dioxide, iron oxides, zinc oxide, bismuth oxychloride (whether pre-dispersed and/or pre-coated or not) D&C dyes and lakes, FD&C colors, natural color additives such as carmine, and mixtures thereof. Depending upon the type of composition, a mixture of pigments is usually used in preferred embodiments of the present invention. Preferred pigments for use herein from the viewpoint of moisturization, skin feel, skin appearance and emulsion compatibility are treated pigments. In some embodiments, the pigments are treated with compounds, including but not limited to amino acids, silicones, lecithin and ester oils.

In preferred embodiments, the pH of the compositions herein is in the range from about 3.5 to about 10, preferably from about 4 to about 8, and more preferably from about 5 to about 7, wherein the pH of the final composition is adjusted by addition of acidic, basic or buffer salts as necessary, depending upon the composition of the forms and the pH-requirements of the compounds.

The compositions of the present invention are prepared by standard techniques well known to those skilled in the art. In general the aqueous phase and/or the oil phase are prepared separately, with materials of similar phase partitioning being added in any order. If the final product is an emulsion, the two phases are then combined with vigorous stirring and/or homogenization as necessary, to reduce the size of the internal phase droplets. Any ingredients in the formulation with high volatility, or which are susceptible to hydrolysis or decomposition at high temperatures, are added with gentle stirring towards the end of the process, post emulsification if applicable. Dosage frequency and amount will depend upon the desired performance criteria.

In some embodiments of the present invention, methods of decreasing FGF-5 activity are provided. In these embodiments, the methods comprise applying to an organism in need thereof an effective amount of any one of the compounds set forth herein. These embodiments also include applications drawn to hair treatment, as well as other applications (e.g., wound healing, treatment of proliferative diseases, etc). In additional preferred embodiments, the present invention provides compounds for treatment of an organism in need thereof.

In additional embodiments, the present invention provides applications for hair and./or skin treatment, as well as applications wound healing, treatment of proliferative diseases, etc. Thus, the present invention provides compositions and methods suitable for application in/on humans and other animals.

Experimental

The following Examples serve to illustrate certain preferred embodiments and aspects of the present invention and are not to be construed as limiting the scope thereof.

In the experimental disclosure which follows, the following abbreviations apply: PI (proteinase inhibitor), BBI (Bowman-Birk inhibitor), STI (Soybean Trypsin inhibitor); ppm (parts per million); M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); V (volts); MW (molecular weight); sec (seconds); min(s) (minute/minutes); hr(s) (hour/hours); ° C. (degrees Centigrade); QS (quantity sufficient); ND (not done); NA (not applicable); rpm (revolutions per minute); $H_2O$ (water); $dH_2O$ (deionized water); (HCl (hydrochloric acid); aa (amino acid); bp (base pair); kb (kilobase pair); kD (kilodaltons); cDNA (copy or complimentary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); $A_{405}$ (absorbance at 405 nm); Vmax (the maximum initial velocity of an enzyme catalyzed reaction); FGFrI(IIIc) (FGF-5 receptor); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto Tryptone, 24 g/l glycerol, 2.31 g/l $KH_2PO_4$, and 12.54 g/l $K_2HPO_4$); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); PBST (PBS+0.25% Tween® 20); PEG (polyethylene glycol); PCR (polymerase chain reaction); RT-PCR (reverse transcription PCR); SDS (sodium dodecyl sulfate); bME, BME and βME (beta-mercaptoethanol or 2-mercaptoethanol); Tris-HCl (tris [Hydroxymethyl]aminomethane-hydrochloride); Tricine (N-[tris-(hydroxymethyl)-methyl]-glycine); CHES (2-(N-cyclo-hexylamino) ethane-sulfonic acid); TAPS (3-{[tris-(hydroxymethyl)-methyl]-amino}-propanesulfonic acid); CAPS (3-(cyclo-hexylamino)-propane-sulfonic acid; DMSO (dimethyl sulfoxide); DTT (1,4-dithio-DL-threitol); Glut and GSH (reduced glutathione); GSSG (oxidized glutathione); TCEP (Tris[2-carboxyethyl] phosphine); Tris (tris(hydroxymethyl)aminomethane); HEPES (N-[2-Hydroxyethyl] piperazine-N-[2-ethanesulfonic acid]); HBS (HEPES buffered saline); SDS (sodium dodecylsulfate); Tris-HCl (tris [Hydroxymethyl]aminomethane-hydrochloride); Ci (Curies) mCi (milliCuries); µCi (microCuries); TLC (thin layer achromatography); Ts (tosyl); Bn (benzyl); Ph (phenyl); Ms (mesyl); Et (ethyl), Me (methyl); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetracetic acid); bla (β-lactamase or ampicillin-resistance gene); PDS (plasma-derived bovine serum that has been dialyzed to remove growth factors; dialysis of defibrinated bovine plasma is performed against DMEM for about 6 hours at 4° C., with stirring, the media is changed and dialysis is continued overnight; the dialyzed PDS is collected after 24 hours, and sterile filtered twice through a 0.2 µm filter); FCS and FBS (fetal calf serum); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Pisacataway, N.J.); NCBI (National Center for Biotechnology Information); Applied Biosystems (Applied Biosystems, Foster City, Calif.); Clontech (CLONTECH Laboratories, Palo Alto, Calif.); Difco (Difco Laboratories, Detroit, Mich.); Oxoid (Oxoid Inc., Ogdensburg, N.Y.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffinann-La Roche, Basel, Switzerland); EM Science (EM Science, Gibbstown, N.J.); Qiagen (Qiagen, Inc., Valencia, Calif.); Biodesign (Biodesign Intl., Saco, Ma.); Aptagen (Aptagen, Inc., Herndon, Va.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); Marsh (Marsh Biosciences, Rochester, N.Y.); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); and Microsoft (Microsoft, Inc., Redmond, Wash.).

The FGF-5 binding peptides produced during the development of the present invention, some of which were used in the following Examples are provided below. In this Table, results for various assays are provided. In this Table, "Synthesized" refers to the peptide tested alone, "BLA" refers to BLA-peptide fusions, and "BBI/BCE" refers to BBI/BCE-peptide fusions; "l1" refers to loop 1, and "l2" refers to loop 2; "BV" refers to the BioVeris Assay (Example 11), and "CBA" refers to the cell-based assays (Example 10).

Table of Peptides

| | | | Synthesized | | BLA | | BBI/BCE | |
|---|---|---|---|---|---|---|---|---|
| Name | SEQUENCE | SEQ ID NO: | BV | CBA | BV | CBA | BV | CBA |
| 1A1 | CYGLPFTRC | SEQ ID NO:4 | | | | | | |
| 1A6 | CEEIWTMLC | SEQ ID NO:8 | | | | – | ++ (12)<br>++ (11), | |
| 1C2 | CWALTVKTC | SEQ ID NO:6 | | | | – | +/– (12) | |
| 2E2 | CLTVLWTTC | SEQ ID NO:14 | | | | – | + (12) | |
| 2E5 | CTLWNRSPC | SEQ ID NO:12 | | – | + | – | ++ (11,<br>12) | – |
| 2H9 | CHYLLTNYC | SEQ ID NO:10 | | | | – | | |
| 2H10 | CRIHLAHKC | SEQ ID NO:2 | | | | – | | |
| FGFns2 | TNIDSTP | SEQ ID NO:45 | | | | | | |
| FGFh12 | HLQTTET | SEQ ID NO:46 | | | | | | |
| MM001 | SLNNLTV | SEQ ID NO:47 | | | ++ | | | |
| MM003 | TNIDSTP | SEQ ID NO:48 | | | ++ | | | |
| MM004 | TNIDSTP | SEQ ID NO:49 | | | | | | |
| MM005 | LRILANK | SEQ ID NO:50 | | | | | | |
| MM007 | RTQPYPL | SEQ ID NO:51 | | | ++ | | ++ | – |
| MM009 | LLTPTLN | SEQ ID NO:52 | | | ++ | | | |
| MM010 | ALPTHSN | SEQ ID NO:53 | | | ++ | | | |
| MM012 | TNIDSTP | SEQ ID NO:54 | | | | | | |
| MM013 | LCRRFEN | SEQ ID NO:55 | | | | | | |
| MM014 | TNIDSTP | SEQ ID NO:56 | | | | | | |
| MM015 | TNIDSTP | SEQ ID NO:57 | | | | | | |
| MM016 | HLQTTET | SEQ ID NO:58 | | | + | | | |
| MM017 | PLGLCPP | SEQ ID NO:59 | | | ++ | | | |
| MM018 | GYFIPSI | SEQ ID NO:60 | | | + | | | |

-continued

Table of Peptides

| Name | SEQUENCE | SEQ ID NO: | Synthesized BV | Synthesized CBA | BLA BV | BLA CBA | BBI/BCE BV | BBI/BCE CBA |
|---|---|---|---|---|---|---|---|---|
| MM019 | TKIDSTP | SEQ ID NO:61 | | | + | | | |
| MM021 | HLQTTET | SEQ ID NO:62 | | | + | | | |
| PS1 | WNIDSTP | SEQ ID NO:63 | | | | | | |
| PS2 | TWIDSTP | SEQ ID NO:64 | | | ++ | | ++ | - |
| PSB | TWIDWTP | SEQ ID NO:65 | | | | | | |

EXAMPLE 1

Dermatological Composition

In this Example, various dermatological compositions comprising any of the compounds of the present invention are provided as follows.

MOISTURIZING BODYWASH (pH 7)

| RAW MATERIAL (INCI Designation) | Amount |
|---|---|
| Deionized Water | QS |
| Glycerin | 4.0 |
| PEG-6 Caprylic/Capric Glycerides | 4.0 |
| Palm Kernel Fatty acids | 3.0 |
| Sodium Laureth-3 Sulphate | 45.0 |
| Cocamide MEA | 3.0 |
| Sodium Lauroamphoacetate | 25.0 |
| Soybean Oil | 10.0 |
| Polyquaternium-10 | 0.70 |
| Preservative, fragrance, color | QS |
| Compound | 1000 ppm |

BODY WASH

| RAW MATERIAL (INCI Designation) | pH 8 Amount | pH 6.5 Amount | pH 7 Amount |
|---|---|---|---|
| Deionized water | QS | QS | QS |
| Sodium Laureth Sulphate | 12 | 15 | 8 |
| Cocamidopropyl Betaine | 8 | 10 | 15 |
| Decyl Glucoside | 0 | 2 | 1 |
| Polyquaternium-10 | 0.25 | 0 | 0 |
| Polyquaternium-7 | 0 | 0 | 0.7 |
| Preservative, fragrance, color | QS | QS | QS |
| Compound | 250 ppm | 500 ppm | 1000 ppm |

| BODY LOTION RAW MATERIAL (INCI Designation) | pH 7 Amount | pH 7 Amount | pH 7.5 Amount | pH 7 Amount |
|---|---|---|---|---|
| Deionized Water | QS | QS | QS | QS |
| Glycerine | 8 | 8 | 0 | 12 |
| Isohexadecane | 3 | 3 | 3 | 6 |
| Niacinamide | 0 | 3 | 5 | 6 |
| Isopropyl Isostearate | 3 | 3 | 3 | 3 |
| Polyacrylamide (and) Isoparaffin (and) Laureth-7 | 3 | 3 | 3 | 3 |
| Petrolatum | 4 | 4 | 4 | 2 |
| Nylon 12 | 2 | 2 | 2.5 | 2.5 |
| Dimethicone | 2 | 2 | 2.5 | 2.5 |
| Sucrose Polycottonseed Oil | 1.5 | 1.5 | 1.5 | 1.5 |
| Stearyl Alcohol 97% | 1 | 1 | 1 | 1 |
| D Panthenol | 1 | 1 | 1 | 1 |
| DL-alpha Tocopherol Acetate | 1 | 1 | 1 | 1 |
| Cetyl Alcohol 95% | 0.5 | 0.5 | 0.5 | 1 |
| Behenyl Alcohol | 1 | 1 | 1 | 0.5 |
| Cetearyl Alcohol (and) Cetearyl Glucoside | 0.4 | 0.4 | 0.5 | 0.5 |
| Stearic Acid | 0.15 | 0.15 | 0.15 | 0.15 |
| PEG-100-Stearate | 0.15 | 0.15 | 0.15 | 0.15 |
| Preservative, fragrance, color | QS | QS | QS | QS |
| Compounds | 250 ppm | 500 ppm | 750 ppm | 1000 ppm |

| ULTRA-HIGH MOISTURIZING EMULSION RAW MATERIAL (INCI Designation) | pH 7 Amount | pH 7 Amount |
|---|---|---|
| Deionized water | QS | QS |
| Glycerin | 12 | 5 |
| PEG 400 | 0 | 10 |
| Niacinamide | 5 | 7 |
| Isohexadecane | 5 | 5 |
| Dimethicone | 3 | 2 |
| Polyacrylamide (and) Isoparaffin (and) Laureth-7 | 3 | 3 |
| Isopropyl Isostearate | 2 | 2 |
| Polymethylsilsesquioxane | 2 | 2 |
| Cetyl Alcohol 95% | 1 | 1 |
| Sucrose polycottonseed oil | 1 | 1 |
| D-Panthenol | 1 | 1 |
| Tocopherol Acetate | 1 | 1 |
| Stearyl Alcohol 95% | 0.5 | 0.5 |
| Cetearyl Glucoside | 0.5 | 0.5 |
| Titanium dioxide | 0.3 | 0.3 |
| Stearic Acid | 0.15 | 0.15 |
| PEG-100-Stearate | 0.15 | 0.15 |
| Preservative, fragrance, color | QS | QS |
| Compound | 250 ppm | 100 ppm |

| MOISTURIZING CREAM RAW MATERIAL (INCI Designation) | pH 7 Amount | pH 7 Amount | pH 7.5 Amount |
|---|---|---|---|
| Deionized water | QS | QS | QS |
| Glycerine | 3 | 5 | 10 |
| Petrolatum | 3 | 3 | 0 |
| Cetyl Alcohol 95% | 1.5 | 1.5 | 1 |
| Dimethicone Copolyol | 2 | 2 | 2 |
| Isopropyl Palmitate | 1 | 1 | 0.5 |
| Carbopol 954 (Noveon) | 0.7 | 0.7 | 0.7 |
| Dimethicone (350 cs) | 1 | 1 | 1 |
| Stearyl Alcohol 97% | 0.5 | 0.5 | 1 |
| Stearic acid | 0.1 | 0.1 | 0.1 |
| Peg-100-stearate | 0.1 | 0.1 | 0.1 |
| Titanium Dioxide | 0.3 | 0.3 | 0.3 |
| Preservative, color, fragrance | QS | QS | QS |
| Compound | 50 ppm | 250 ppm | 1000 ppm |

LEAVE-ON HAIR CONDITIONER

| RAW MATERIAL (INCI Designation) | Amount |
|---|---|
| Deionized Water | QS |
| Isostearamidopropyl Morpholine Lactate | 6.0 |
| Hydroxyethylcellulose | 1.0 |
| Preservative, fragrance, color | QS |
| Compound | 1000 ppm |

CREAM RINSE (pH 4)

| RAW MATERIAL (INCI Designation) | Amount |
|---|---|
| Deionized Water | QS |
| Behentrimonium Chloride | 2.0 |
| Trilaureth-4 Phosphate | 1.5 |
| Cetyl alcohol | 2.0 |
| Citric acid | QS |
| Preservative, fragrance, color | QS |
| Compound | 1000 ppm |

NOURISHING HAIR CONDITIONER/TREATMENT (pH 6)

| RAW MATERIAL (INCI Designation) | Amount |
|---|---|
| Deionized Water | QS |
| Behentrimonium Methosulfate (and) Cetyl Alcohol | 4.0 |
| Wheat germ oil | 1.0 |
| Cetyl alcohol | 0.5 |
| Propylene glycol | 5.0 |
| PEG-60 Lanolin | 1.0 |
| Panthenol | 2.0 |
| Lupin amino acids | 1.0 |
| Cocodimonium Hydroxypropyl Hydrolyzed Wheat Protein | 1.0 |
| Fragrance, preservative, color | QS |
| Compound | 1000 ppm |

CONDITIONING SHAMPOO

| RAW MATERIAL (INCI Designation) | Amount |
|---|---|
| Deionized Water | QS |
| Sodium Laureth Sulfate 30% | 27.0 |
| Cocamidopropyl Betaine | 3.7 |
| Coco-Glucoside (and) Glyceryl Oleate | 5.0 |
| Coco-Glucoside (and) Glycol Distearate (and) Glycerine | 3.0 |
| Guar Hydroxypropyl Trimonium Chloride | 0.1 |
| Laureth-2 | 1.55 |
| Fragrance, preservative, color | QS |
| Compound | 1000 ppm |

ANTI-DANDRUFF SHAMPOO

| RAW MATERIAL (INCI Designation) | Amount |
|---|---|
| Deionized Water | QS |
| Magnesium Aluminum Silicate | 1.0 |
| Hydroxypropyl Methylcellulose | 0.8 |
| Sodium Olefin Sulfate 40% | 35.0 |
| Lauramide DEA | 4.0 |
| Soyamide DEA | 1.0 |
| Quaternium-70 Hydrolyzed Collagen | 2.0 |
| Zinc Pyrithione 40% | 4.0 |
| Fragrance, preservative, color | QS |
| Compound | 1000 ppm |

EXAMPLE 2

Panning of a Phage Displayed Peptide Library

In this Example, experiments conducted involving panning of a phage-displayed peptide library are described. A commercially available phage peptide library PhD C7C (NEB) was panned against FGF-5, according to the manufacturer's instructions. Phage that was still bound to the target after extensive washes, including an acid wash, was used as a template for PCR reactions.

EXAMPLE 3

Construction of a Peptide-BLA Library for FGF-5

In this Example, construction of a peptide-BLA library is described. PCR product after one round of phage panning of FGF-5 was cloned into pME 30.16 to obtain library pGV04-L. pGV04-L encodes 9-amino acid peptide sequences fused to the N-terminus of *E. cloaceae* β-lactamase (BLA) with a pIII signal sequence and C-terminal 6×His tag (See, FIG. 1). The plasmid also carries a chloramphenicol resistance gene (CAT) as a selectable marker and expression is driven by a lac promoter (Plac). To make the inserts the PCR product was used as a template for a PCR reaction using primers with BbsI tails.

```
Oligos:
ME 190f:
                                        (SEQ ID NO:66)
GCTATTCAATGTCAGACGAAGACGTCGTTCCTTTCTATTCTCACTCT

ME 190r:
                                        (SEQ ID NO:67)
GGTGGAGGTTCGGCGTCTTCCCGACTGAATGGCTAT
```

The cut vector, and stuffer insert (200 bp) were ligated overnight at 16° C. in a 1:5 molar ratio respectively, using 10 μl of the DNA mix and 10 ul of Takara solution I ligase. Ligations were purified using Zymo Research DNA clean kit and eluted in 2× μl of water. Then, 5 μl of ligation mix was transformed into 40 μl Top 10 (*E. coli*) electrocompetent cells (Invitrogen), 260 μl SOC was added and the cells were grown for 1 h at 37° C. The transformation mix was diluted 1/10 and plated on both LA+5 ppm CMP and LA+5 ppm CMP+0.1 ppm CTX plates, followed by incubation overnight at 37° C.

EXAMPLE 4

Primary Screen of FGF-5-Binding BLA-Peptides Using Nitrocefin

In this Example, experiments conducted for primary screening of FGF-5-binding peptides are described. Peptides fused to the N-terminus of β-lactamase (BLA) were screened for binding to FGF-5, using enzymatic activity on the lactamase substrate nitrocefin as the reporter.

Growth and Assay Procedure

Peptide-BLA fusions were expressed in *E. coli*. The growth medium used was Luria Broth plus 5 mg/mL chloramphenicol (CMP). One hundred ml of the growth medium was added to each well of a sterile Costar 3598 96-well plate (Corning). One clonal colony was picked into each well using a sterile toothpick, and the plate was covered and placed in a humidified shaker/incubator for 40 hours at 37° C. After incubation, 100 mL "B-PER in Phosphate Buffer" (Pierce) was added to each well, and the plate was gently shaken for 30 minutes at room temperature. The resulting cell lysate was diluted 10× in PBS. Then, 100 ml per well of the diluted cell lysate was added to the assay plate (assay plate preparation is described below), which was then covered with a plate sealer (Marsh) and incubated for two hours at room temperature. The assay plate was transferred to a 96-well plate washer (Bio-Tek), where the diluted cell lysate was aspirated and the plate washed once with 100 ml per well, then 3 times with 300 mL PBS plus 0.1% Tween-20 (PBS-T) per well. Then, 200 mL nitrocefin working solution was immediately added to each well. Nitrocefin working solution was prepared just prior to use, by diluting a 100 mg/mil (in DMSO) stock 1000-fold in PBS plus 0.125% n-Octyl-Beta-D-Glucopyranoside (Sigma). After addition of the nitrocefin working solution, the plate was shaken at room temperature for one minute, then read for 5 minutes at 495 nm on a Spectramax plate spectraphotometer (Molecular Devices) in kinetic mode. Total BLA activity in the cell lysate was also be measured by diluting cell lysate 1:100, then combining 20 ml per well of this dilution with 180 ml per well of the nitrocefin working solution.

Assay Plate Preparation

A Costar 3594 assay plate (Corning) was prepared by incubating 100 mL per well of a 1 mg/mL solution of FGF-5 (R&D Systems) in 50 mM sodium carbonate, pH 9.6. The plate was covered with a plate sealer (Marsh) and incubated two hours at room temperature. The plate was transferred to a 96-well plate washer (Bio-Tek), where the FGF-5 solution was aspirated and the plate washed 3 times with 300 ml PBS-T per well. "Blocker Casein in PBS" (Pierce) was added at 300 mL per well and the plate was incubated overnight at 4 degrees C. "Blocker Casein in PBS" was aspirated and the plate washed 3 times with 300 ml PBS-T per well. The plate was used in the assay immediately following the last wash. For screens in which it was important to distinguish specific FGF-5 binders from nonspecific (background) binders, a no-target control plate was prepared, beginning with the addition of "Blocker Casein in PBS", and following the same steps as described.

Data Analysis

In the primary screen, throughput was high priority, and the no-target control plate was left out of the procedure. The BLA activity of the bound material was plotted against the total BLA activity in the sample, and points that lie above a y-axis cutoff were selected as winners (See, FIG. 2). The cutoff was arbitrarily set by the researcher at a value which, for that specific data set, seems likely to separate true binders from the general mass of data points (See, FIG. 2).

In the secondary screen, triplicate samples of the "winners" from the primary screen were grown and assayed together, and a no-target control condition was run in parallel, to distinguish FGF-5 binders from nonspecific (background) binders. Wild-type BLA were grown and assayed, to give a measure of the natural "stickiness" of the BLA portion of the fusion molecule. The data were normalized for expression by dividing the FGF-5-binding and background-binding activity by the total BLA activity for every well, and the normalized data sets were plotted against each other. Points that lie significantly closer to the "Normalized Bound" axis than the bulk of the data field were selected as winners. Significance was determined by a visual assessment of each point's location in the data field, and the size of its error bars. The slope of the data set deviated slightly from unity, indicating either nonspecific stickiness due to the presence of FGF-5 or plate-to-plate variation from the assay. The results of these experiments are provided in FIG. 3.

EXAMPLE 5

Secondary Screen of FGF-5-Binding-BLA-Peptides Using Nitrocefin

This Example describes secondary screening methods used to analyze FGF-5 binding npeptides. Individual clones were picked and grown up in 5 ml LB+5 ppm CMP overnight at 37° C. The cell pastes were then treated with 125μ of B-PER reagent (Pierce) for 30 min with slow mixing. COSTAR plates (96-well) were coated with 0.1 μg (100 μl of 1 μg/ml) FGF-5, carrier-free (R&D Systems #237-F5/CF, Lot #GQ18304A) with gentle rocking at 4° C. overnight, followed by blocking with Superblock blocking buffer (Pierce) for several hours at room temperature. Then, 100 μl B-Per treated supernatant from individual clones from pGV02-L were added to the FGF-5 coated plates. After one hour, plates were washed six times with PBS, 0.05% TWEEN®-20 and 200 μl of nitrocefin assay buffer containing 0.1 mg/ml nitrocefin (Oxoid) was added to measure residual bound beta-lactamase activity, using $Abs_{490}$/min. Control wells contained pCB04 (See, FIG. 1C) beta-lactamase as a control. Out of 180 clones, 7 showed a positive signal. These clones were sequenced, and the results are provided in Table 1, where the first column is the name of the peptide, the second column is the nucleotide sequence and the third column is the amino acid sequence of the peptide:

TABLE 1

| Clones Sequenced | | |
|---|---|---|
| Name | Nucleotide Sequence | Amino Acid Sequence |
| 2H10 | TGTCGGATTCATCTGGCGCATAAGTGC (SEQ ID NO:1) | CRIHLAHKC (SEQ ID NO:2) |
| 1A1 | TGTTATGGGCTGCCTTTTACGCGGTGC (SEQ ID NO:3) | CYGLPFTRC (SEQ ID NO:4) |
| 1C2 | TGTTGGGCGCTTACTGTGAAGACTTGC (SEQ ID NO:5) | CWALTVKTC (SEQ ID NO:6) |
| 1A6 | TGTGAGGAGATTTGGACTATGCTGTGC (SEQ ID NO:7) | CEEIWTMLC (SEQ ID NO:8) |
| 2H9 | TGTCATTTATCTGCTGACTAATTATGC (SEQ ID NO:9) | CHYLLTNYC (SEQ ID NO:10) |
| 2E5 | TGTACTCTTTGGAATCGTTCTCCGTGC (SEQ ID NO:11) | CTLWNRSPC (SEQ ID NO:12) |
| 2E2 | TGTCTGACGGTGTTGTGGACGACTTGC (SEQ ID NO:13) | CLTVLWTTC (SEQ ID NO:14) |

EXAMPLE 6

Purification of Sequenced Clones

In this Example, experiments involving purification of the BLA-peptide fusion proteins of the three clones in Example 5 are described. These fusion proteins were expressed in *E. coli* (TOP10; Invitrogen) in 15-ml shake flasks in the presence of 5 ppm CMP and 0.1 ppm cefotoxime (CTX) antibiotic at 37° C. overnight. A commercially available purification kit (Insect RoboPop Ni/NTA His Bind Purification Kit, Novagen) was used to purify these peptide BLA fusions according to the manufacturer's instructions.

EXAMPLE 7

Peptide-BLA Screen Using Purified Clones

Cell pastes were harvested from the 200 ml cell cultures described in Example 6, by centrifugation at 3,000×g for 10 min. The pastes were then treated with 25 ml of B-PER reagent (Pierce) for 40 min with slow mixing. The extract was separated by centrifugation at 20,000 g for 20 min. BLA activity of all liquid fractions was assayed using nitrocefin, and the concentration of fusion proteins in each fraction was calculated assuming the same specific activity as the WT enzyme. Fusion proteins were purified by IMAC chromatography (See, FIG. 4). The imidazole-eluted BLA-active fractions were pooled and the purity was found better than 95% as checked by SDS-PAGE. (See, FIG. 5).

The binding (BLA assay) was repeated using different peptide concentrations to see a dose response. To verify specific binding, the assay was also done using an irrelevant target. The results are shown in FIG. 6 and in Table 2, below.

TABLE 2

| BLA Binding Assay Results | |
|---|---|
| Sample | Percent Bound at 0.1 nM |
| 2E2 | 7 |
| 2H10 | 8 |
| 2H9 | 5 |
| 1A6 | 8 |
| WT (wild-type) | 0.4 |

EXAMPLE 8

BIAcore™ Binding Analysis of FGF-5 Binding BLA-Peptides

In this Example, experiments conducted to determine the affinities of the peptides for FGF-5 are described. Affinities of the peptides for FGF-5 were measured using a BIAcore™-3000 surface plasmon resonance system (Biacore). A CM5 sensor chip was conditioned with 50 mM NaOH, 0.1% HCl, 0.1% SDS and 0.08% $H_3PO_4$ and activated for covalent coupling of FGF-5 using N-ethyl-N'-(3-dimethylaminopropyl)-carbodiimide hydrochloride (EDC) and N-hydroxysuccinimide (NHS) according to the supplier's instructions (Biacore). Human FGF-5 (PeproTech) was diluted to 5 μg/mL in 20 mM sodium acetate, pH 4.8, and injected at a flow rate of 2 μL/min to achieve approximately 1000 to 2000 response units (RU) of coupled protein. An additional solution of EDC and NHS was injected to improve baseline stability and a solution of 1 M ethanolamine was injected as a blocking agent. The reference lane was activated with EDC and NHS and blocked with ethanolamine.

Peptides were synthesized using standard FMOC chemistry, purified by reverse phase HPLC to >95% purity (SynPep) and stored at 10 mg/mL in either water or 10% DMSO. For kinetic measurements, three-fold or four-fold serially diluted peptides in HBS-EP buffer, 0.01 M HEPES pH 7.4, 0.15 M NaCl, 3 mM EDTA, 0.005% Surfactant P20 (Biacore), were injected at 25° C. at a flow rate of 50 μL/min. Serially diluted DMSO samples and buffer samples were also injected for background measurements and subtraction. Two short injections of 25 mM NaOH were used between sample injections for regeneration. Kinetic parameters were calculated using software programs, Scrubber version 1.1f, BIAevaluation 3.1 and Clamp99 version 3.30.

EXAMPLE 9

Construction of FGF-5Binding-BBI-Peptide Constructs

In this Example, methods used in the construction of FGF-5-binding BBI-peptide constructs are described. The FGF5 binding peptides were introduced into the BBI trypsin inhibitory loop or chymotrypsin inhibitory loop using the QuikChange® II XL Site-Directed Mutagenesis Kit (Stratagene). The mutagenesis reaction was performed essentially as described in the technical manual provided by the manufacturer (Stratagene). The vector, p2JM103-DNNDI-BBI (See, FIG. 1), was used as a template. This *B. subtilis* expression vector has the BCE103 cellulase fused to BBI with a cleavable linker between the two domains. In the mutagenesis reaction, approximately 200 ng of the plasmid was used with 50 pmol of each of the oligonucleotide primers (shown below). The reaction mixture was held at 97° C. for 3 minutes and then held at 50° C. until the polymerase was added to each tube. The reaction mixture was then thermally cycled at 68° C. for 6 minutes, 95° C. for 50 seconds and then 55° C. for 50 seconds for 22 times. After cycling, the reaction mixture was held at 68° C. for 20 minutes and then cooled to 4° C. After DpnI digestion, an aliquot of the reaction mixture was used to transform XL10Gold cells, colonies picked, plasmids isolated (QIAprep® Spin Miniprep Kit, Qiagen) and the variants detected by restriction digests. Positives were checked for the correct sequence by DNA sequencing.

Oligonucleotide Primer Sequences:

Trypsin Loop

```
1A6 peptide
1A6FGF5-F:
TCAATGCGCATGTGAAGAGATCTGGACTATGCTTTG (SEQ ID NO:68)

CCGGTGTTCCGATATGCGTC

1A6FGF5-R:
CGGAACACCGGCAAAGCATAGTCCAGATCTCTTCAC (SEQ ID NO:69)

ATGCGCATTGATCGCAACAGG

1C2 peptide
1C2FGF5-F:
TCAATGCGCATGTTGGCCCTTACTGTCAAAACATGC (SEQ ID NO:70)

CGGTGTTCCGATATGCGTC

1C2FGF5-F:
CGGAACACCGGCATGTTTTGACAGTAAGGGCCCAAC (SEQ ID NO:71)

ATGCGCATTGATCGCAACAGG

2E2 peptide
2E2FGF5-F:
TCAATGCGCATGTCTTACAGTACTGTGGACTACATG (SEQ ID NO:72)

CCGGTGTTCCGATATGCGTC

2E2FGF5-R:
CGGAACACCGGCATGTAGTCCACAGTACTGTAAGAC (SEQ ID NO:73)

ATGCGCATTGATCGCAACAGG

2E5 peptide
2E5FGF5-F:
TCAATGCGCATGTACTCTTTGGAACAGATCTCCTTG (SEQ ID NO:74)

CCGGTGTTCCGATATGCGTC

2E5FGF5-R:
CGGAACACCGGCAAGGAGATCTGTTCCAAAGAGTAC (SEQ ID NO:75)

ATGCGCATTGATCGCAACAGG
```

Chymotrypsin Loop

```
1A6 peptide
1A6FGF5-2F:
CAAAAGCTGTGCTTGTGAAGAGATCTGGACTATGCT (SEQ ID NO:76)

TTGCTTTTGCGTCGACATCACGG
```

-continued

```
1A6FGF5-2R
ACGCAAAAGCAAAGCATAGTCCAGATCTCTTCACAA (SEQ ID NO:77)

GCACAGCTTTTGCATGCACTATG

1C2 peptide
1C2FGF5-2F:
CAAAAGCTGTGCTTGTTGGGCCCTTACTGTCAAAAC (SEQ ID NO:78)

ATGCTTTTGCGTCGACATCACGG

1C2FGF5-2R:
ACGCAAAAGCATGTTTTGACAGTAAGGGCCCAACAA (SEQ ID NO:79)

GCACAGCTTTTGCATGCACTATG

2E2 peptide
2E2FGF5-2F:
CGGAACACCGGCATGTTTTGACAGTAAGGGCCCAAC (SEQ ID NO:80)

ATGCGCATTGATCGCAACAGG

2E2FGF5-2R:
ACGCAAAAGCATGTAGTCCACAGTACTGTAAGACAA (SEQ ID NO:81)

GCACAGCTTTTGCATGCACTATG

2E5 peptide
2E5FGF5-2F:
CAAAAGCTGTGCTTGTACTCTTTGGAATCGATCTCC (SEQ ID NO:82)

TTGCTTTTGCGTCGACATCACGG

2E5FGF5-2R:
ACGCAAAAGCAAGGAGATCGATTCCAAAGAGTACAA (SEQ ID NO:83)

GCACAGCTTTTGCATGCACTATG
```

The sequences of the resulting constructs (SEQ ID NOS: 84-101) are provided in FIG. 9.

EXAMPLE 10

Cell-Based Assay Using NR6R-3T3 Cells

In this Example, experiments conducted to determine the biological activity of the BLA-peptide fusion proteins, BBI/BCE-peptide fusion proteins, as well as BBI-peptide fusion proteins are described. The biological activity of the BLA-peptide fusion proteins was measured in a proliferation bioassay, using NR6R-3T3 cells. The NR6R-3T3 cell line is a cloned murine fibroblast cell line obtained from Dr. A. Rizzino. This assay system is well-defined and used by R & D Systems as a means to measure the activity of cytokines and growth factors (See, R&D Systems, Inc., protocols for more details). The cells are typically grown in DMEM containing 4.5 g/l glucose, supplemented with supplemented with 10% v/v FBS, 2 mM L-glutamine, 100 Units/ml penicillin, 100 μg/ml streptomycin. The Assay Medium used was DMEM, supplemented with 2% plasma-derived bovine serum (PDS is dialyzed to remove growth factors), 2 mM L-glutamine, 100 Units/ml penicillin, and 100 μg.ml streptomycin.

Cells were grown up and then incubated with the FGF-5-1 peptide fusion proteins (i.e., BLA-FGF-5, or BBI/BCE-FGF-5, with modifications to loop 1 ("l1") and/or loop 2 ("l2"), as described in Example 10. Cells were harvested at confluency (approximately $3\times10^6$ cells/flask). The standards samples were diluted to working concentrations in PBS, 1.0 mg/ml BSA, and 0.1 μg/ml sodium heparin. Sodium heparin stock is in a solution of DMEM+2% PDS. Prior to use, the microtiter plates were pre-blocked with PBS and 1% BSA for two hours at room temperature.

In order to measure the ability of the peptide fusions to "neutralize" or antagonize the bioactivity of the FGF-5 on the cells, constant concentrations of FGF-5 were incubated with various concentrations of the peptide for either 30 minutes or 1 hour at room temperature or 37° C. in a 96-well microtiter plate. At 72 hours prior to setting up assay, cells were harvested at confluency (approximately $3\times10^6$ cells/flask). Cells were plated in a 96-well flat bottom plate at $0.5\times10^4$ cells in 100 μl Growth Medium. The Growth Medium was removed after 48 hours and replaced with 100 μl Assay Medium/well, so that cells would be in a resting phase and ready for assay, 24 hours later. The samples were diluted in DMEM-2% PDS. The standards and samples were then added to the plate. The assay mixture was incubated at 37° C. for approximately 16-18 hours in a 5% $CO_2$ incubator with humidity. Then, 3H-thymidine (10 μl/well of 25 μCi/ml $^3$H-thymidine working stock in Assay Medium) was added, for another 2 hours of incubation. The cells were subsequently harvested onto glass fiber filters. In order to ensure all attached cells were removed, plate was rinsed with 200 μl 1× PBS without Ca or Mg and then treated with 100 μl 0.25% trypsin in EDTA. The amount of 3H-thymidine incorporated into DNA was then determined. The dose response was then determined for the various concentrations of FGF-5. Some results obtained are provided in the Table of Peptides (See, above) and in FIGS. 7 and 12. As shown in FIG. 12, MM07-BBI and PS02-BBI bind and neutralize FGF-5 activity.

EXAMPLE 11

BioVeris Assay

In this Example, binding assays using BioVeris's protocols are described. This assay system was optimized by testing several of the reagents at different concentrations to determine maximum signal:background ratio. Various constructs produced as described above were tested in this assay system.

The assay was conducted as follows. First, the target (e.g., FGF-5) was biotinylated using EZ-Link Sulfo-NHS-Biotin (Pierce) and the protocol provided by the manufacturer. The receptor (FGFrI(IIIc) was then tagged using BV-tag ( BioVeris), using the BioVeris labeling protocol. Diluted stock solutions of each reagent above (at optimized concentrations to provide the best signal:background ratio) were prepared in PBS with 0.05% TWEEN®-80 to the following concentrations: bFGF5: 500 ng/mL and BV-FGFrI(IIIc): 250 ng/mL.

Then, 50 μl of biotinylated target were added to each well of a 96 well round bottom polypropylene plate (Costar 3365). Next, 50 μl of the construct to be tested (6 serial dilutions prepared (1000 nM→0) in PBS+0.05% TWEEN®-80, to provide a range of activity) were added to the wells. Then, 50 μl BV-FGFr(IIIc) diluted in PBS+0.05% TWEEN®-80 was added to the wells. The plate was incubated with gentle shaking (being careful to avoid well to well transfer) for 1 hour at room temperature. Following incubation, 50 μl streptavidin microbeads (Dynal) (0.2 mg/mL diluted in PBS+0.05% TWEEN®-80) were added to the wells The plates were then incubated for 30 minutes at room temperature, with gentle shaking. The total in the wells was then brought up to 250 μl/well with PBS+0.05% TWEEN®-80. The plate was then read on a BioVeris M Series 384 machine, using the default program. Some results obtained are provided in the Table of Peptides (See, above) and in FIG. 11.

EXAMPLE 12

In Vivo and Ex Vivo Assays

In this Example, in vivo assays to evaluate the constructs produced above are described. In particular, in vivo assays are performed to test each of the constructs for hair care, as known in the art (See e.g., Tobin et al., J. Invest. Dermatol., 120:895 [2003]).

In additional embodiments, methods such as those that assess the influence of growth factors on hair growth find use in the present invention. Such methods are known in the art and include, but are not limited to the Philpott assay system (See e.g., Philpott et al., J. Dermatol. Sci., 7 (Suppl.):S55-72 [1994]).

Having described the preferred embodiments of the present invention, it will appear to those ordinarily skilled in the art that various modifications may be made to the disclosed embodiments, and that such modifications are intended to be within the scope of the present invention.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the following claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. A composition comprising at least one peptide selected from the group consisting of SEQ ID NOS:2, 4, 6, 8, 10, 12, and 14, wherein said peptide binds to a fibroblast growth factor.

2. The composition of claim 1, wherein said peptide is encoded by a nucleic acid sequence selected from the group consisting of SEQ ID NOS:1, 3, 5, 7, 9, 11, and 13.

3. The composition of claim 1, wherein said peptide is expressed in a protease resistant scaffold.

4. The composition of claim 3, wherein said scaffold is a protease inhibitor.

5. The composition of claim 4, wherein said protease inhibitor is selected from the group consisting of Bowman-Birk Inhibitor, soybean trypsin inhibitor, and Eglin chymotrypsin inhibitor.

6. The composition of claim 3, wherein said protease resistant scaffold and said peptide comprise a fusion protein.

7. A cosmetic or pharmaceutical composition comprising said peptide of claim 1.

8. The composition of claim 7, wherein said composition is capable of modulating hair growth.

9. The composition of claim 7, wherein said composition further comprises a scaffold.

10. A method for promoting hair growth comprising:

i) providing a composition comprising a peptide contained within a scaffold, wherein said peptide is selected from the group consisting of SEQ ID NOS: 2, 4, 6, 8, 10, 12, and 14;

ii) providing a subject to be treated; and iii) applying said composition to said subject in an area in which hair growth promotion is desired.

11. The method of claim 10, wherein said peptide binds to a fibroblast growth factor.

12. The method of claim 11, wherein said fibroblast growth factor (FGF) is FGF-5.

13. The method of claim 10, wherein said scaffold is selected from the group consisting of Bowman-Birk inhibitor, soybean trypsin inhibitor, and Eglin chymotrypsin inhibitor.

14. A method for promoting hair growth comprising:

i) providing a composition comprising a peptide contained within a scaffold, wherein said peptide is encoded by a nucleic acid sequence selected from the group consisting of SEQ ID NOS:1, 3, 5, 7, 9, 11 and 13;

ii) providing a subject to be treated; and iii) applying said composition to said subject in an area in which hair growth promotion is desired.

15. A method for decreasing the activity of a fibroblast growth factor comprising the steps of:

i) providing a subject; and ii) administering the composition of claim 1 to said subject, under conditions such that the activity of said fibroblast growth factor is decreased.

16. The method of claim 15, wherein said fibroblast growth factor is FGF-5.

17. A composition comprising an FGF-5 peptide sequence selected from the group of SEQ ID NOS: 2, 4, 6, 8, 10, 12, 14, 21, 25, 27, 28, 38, 41, 43, 51, 63-65, 86, 88, 90, 92, 94, 96, 99 and 101.

18. A composition comprising an FGF-5 peptide wherein the FGF-5 peptide consists of a sequence selected from the group consisting of SEQ ID NOs: 2, 4, 6, 8, 10, 12, 14, 16, 17, 19, 21-23, 25, 27-29, 31, 36-38, 41, 43, 47, 51, 63-65, 86, 88, 90, 92, 94, 96, 99 and 101.

* * * * *

SEQUENCE LISTING

<160> NUMBER OF SEQ ID NOS: 101

<210> SEQ ID NO 1
<211> LENGTH: 27
<212> TYPE: DNA
<213> ORGANISM: Artificial Sequence
<220> FEATURE:
<223> OTHER INFORMATION: synthesized sequence encoding SEQ ID NO:2

<400> SEQUENCE: 1
tgtcggattc atctggcgca taagtgc 27

<210> SEQ ID NO 2
<211> LENGTH: 9
<212> TYPE: PRT
<213> ORGANISM: Artificial Sequence
<220> FEATURE:
<223> OTHER INFORMATION: synthesized FGF-5 binding peptide

<400> SEQUENCE: 2

Cys Arg Ile His Leu Ala His Lys Cys
1 5

<210> SEQ ID NO 3
<211> LENGTH: 27
<212> TYPE: DNA
<213> ORGANISM: Artificial Sequence
<220> FEATURE:
<223> OTHER INFORMATION: synthesized sequence encoding SEQ ID NO:4

<400> SEQUENCE: 3
tgttatgggc tgccttttac gcggtgc 27

<210> SEQ ID NO 4
<211> LENGTH: 9
<212> TYPE: PRT
<213> ORGANISM: Artificial Sequence
<220> FEATURE:
<223> OTHER INFORMATION: synthesized FGF-5 binding peptide

<400> SEQUENCE: 4

Cys Tyr Gly Leu Pro Phe Thr Arg Cys
1 5

<210> SEQ ID NO 5
<211> LENGTH: 27
<212> TYPE: DNA
<213> ORGANISM: Artificial Sequence
<220> FEATURE:
<223> OTHER INFORMATION: synthesized sequence encoding SEQ ID NO:6

<400> SEQUENCE: 5
tgttgggcgc ttactgtgaa gacttgc 27

<210> SEQ ID NO 6
<211> LENGTH: 9
<212> TYPE: PRT
<213> ORGANISM: Artificial Sequence
<220> FEATURE:
<223> OTHER INFORMATION: synthesized FGF-5 binding peptide

<400> SEQUENCE: 6

Cys Trp Ala Leu Thr Val Lys Thr Cys
1 5

-continued

<210> SEQ ID NO 7
<211> LENGTH: 27
<212> TYPE: DNA
<213> ORGANISM: Artificial Sequence
<220> FEATURE:
<223> OTHER INFORMATION: synthesized sequence encoding SEQ ID NO:8

<400> SEQUENCE: 7
tgtgaggaga tttggactat gctgtgc 27

<210> SEQ ID NO 8
<211> LENGTH: 9
<212> TYPE: PRT
<213> ORGANISM: Artificial Sequence
<220> FEATURE:
<223> OTHER INFORMATION: synthesized FGF-5 binding peptide

<400> SEQUENCE: 8

Cys Glu Glu Ile Trp Thr Met Leu Cys
1 5

<210> SEQ ID NO 9
<211> LENGTH: 27
<212> TYPE: DNA
<213> ORGANISM: Artificial Sequence
<220> FEATURE:
<223> OTHER INFORMATION: synthesized sequence encoding SEQ ID NO:10

<400> SEQUENCE: 9
tgtcattatc tgctgactaa ttattgc 27

<210> SEQ ID NO 10
<211> LENGTH: 9
<212> TYPE: PRT
<213> ORGANISM: Artificial Sequence
<220> FEATURE:
<223> OTHER INFORMATION: synthesized FGF-5 binding peptide

<400> SEQUENCE: 10

Cys His Tyr Leu Leu Thr Asn Tyr Cys
1 5

<210> SEQ ID NO 11
<211> LENGTH: 27
<212> TYPE: DNA
<213> ORGANISM: Artificial Sequence
<220> FEATURE:
<223> OTHER INFORMATION: synthesized sequence encoding SEQ ID NO:12

<400> SEQUENCE: 11
tgtactcttt ggaatcgttc tccgtgc 27

<210> SEQ ID NO 12
<211> LENGTH: 9
<212> TYPE: PRT
<213> ORGANISM: Artificial Sequence
<220> FEATURE:
<223> OTHER INFORMATION: synthesized FGF-5 binding peptide

<400> SEQUENCE: 12

Cys Thr Leu Trp Asn Arg Ser Pro Cys
1 5

<210> SEQ ID NO 13
<211> LENGTH: 27
<212> TYPE: DNA

-continued

<213> ORGANISM: Artificial Sequence
<220> FEATURE:
<223> OTHER INFORMATION: synthesized sequence encoding SEQ ID NO:14

<400> SEQUENCE: 13
tgtctgacgg tgttgtggac gacttgc 27

<210> SEQ ID NO 14
<211> LENGTH: 9
<212> TYPE: PRT
<213> ORGANISM: Artificial Sequence
<220> FEATURE:
<223> OTHER INFORMATION: synthesized FGF-5 binding peptide

<400> SEQUENCE: 14

Cys Leu Thr Val Leu Trp Thr Thr Cys
1 5

<210> SEQ ID NO 15

<400> SEQUENCE: 15

000

<210> SEQ ID NO 16
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 16

Pro Leu Gly Leu Cys Pro Pro
1 5

<210> SEQ ID NO 17
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 17

Thr Asn Ile Asp Ser Thr Pro
1 5

<210> SEQ ID NO 18
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 18

Thr Asn Ile Asp Ser Thr Pro
1 5

<210> SEQ ID NO 19
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 19

Leu Arg Ile Leu Ala Asn Lys
1 5

-continued

<210> SEQ ID NO 20

<400> SEQUENCE: 20

000

<210> SEQ ID NO 21
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 21

Arg Thr Gln Pro Tyr Pro Leu
1 5

<210> SEQ ID NO 22
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 22

Gly Tyr Phe Ile Pro Ser Ile
1 5

<210> SEQ ID NO 23
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 23

Leu Leu Thr Pro Thr Leu Asn
1 5

<210> SEQ ID NO 24
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 24

Thr Asn Ile Asp Ser Thr Pro
1 5

<210> SEQ ID NO 25
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 25

His Leu Gln Thr Thr Glu Thr
1 5

<210> SEQ ID NO 26
<211> LENGTH: 7
<212> TYPE: PRT
<213> ORGANISM: Artificial Sequence
<220> FEATURE:

-continued

<223> OTHER INFORMATION: synthesized FGF-5 binding peptide

<400> SEQUENCE: 26

Pro Leu Gly Leu Cys Pro Pro
 1               5

<210> SEQ ID NO 27
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 27

Thr Lys Ile Asp Ser Thr Pro
 1               5

<210> SEQ ID NO 28
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 28

Thr Lys Ile Asp Arg Thr Pro
 1               5

<210> SEQ ID NO 29
<211> LENGTH: 7
<212> TYPE: PRT
<213> ORGANISM: Artificial Sequence
<220> FEATURE:
<223> OTHER INFORMATION: synthesized FGF-5 binding peptide
<220> FEATURE:
<221> NAME/KEY: VARIANT
<222> LOCATION: 1
<223> OTHER INFORMATION: Xaa = Any Amino Acid

<400> SEQUENCE: 29

Xaa Met Ala Glu Tyr Met Tyr
 1               5

<210> SEQ ID NO 30
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 30

His Leu Gln Thr Thr Glu Thr
 1               5

<210> SEQ ID NO 31
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 31

Ala Leu Pro Thr His Ser Asn
 1               5

<210> SEQ ID NO 32

-continued

<400> SEQUENCE: 32

000

<210> SEQ ID NO 33
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 33

Thr Asn Ile Asp Ser Thr Pro
1 5

<210> SEQ ID NO 34
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 34

Leu Cys Arg Arg Phe Glu Asn
1 5

<210> SEQ ID NO 35
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 35

Thr Asn Ile Asp Ser Thr Pro
1 5

<210> SEQ ID NO 36
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 36

Arg Thr Leu Pro His Ser Tyr
1 5

<210> SEQ ID NO 37
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 37

Ala Thr Pro Asn His Ser Tyr
1 5

<210> SEQ ID NO 38
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 38

-continued

```
Pro Ala Ile Asn Arg Asp Pro
 1               5


<210> SEQ ID NO 39
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 39

Ala Thr Pro Asn His Ser Tyr
 1               5


<210> SEQ ID NO 40
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 40

Ala Thr Pro Asn His Ser Tyr
 1               5


<210> SEQ ID NO 41
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 41

Leu Met Phe Asp Trp Thr Pro
 1               5


<210> SEQ ID NO 42
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 42

Leu Leu Thr Pro Thr Pro Asn
 1               5


<210> SEQ ID NO 43
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 43

Leu Leu Thr Pro Thr Leu Asp
 1               5


<210> SEQ ID NO 44
<211> LENGTH: 71
<212> TYPE: PRT
<213> ORGANISM: Glycine max

<400> SEQUENCE: 44

Asp Asp Glu Ser Ser Lys Pro Cys Cys Asp Gln Cys Ala Cys Thr Lys
 1               5                   10                  15
```

-continued

```
Ser Asn Pro Pro Gln Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
        35                  40                  45

Cys Phe Cys Val Asp Ile Thr Asp Phe Cys Tyr Glu Pro Cys Lys Pro
    50                  55                  60

Ser Glu Asp Asp Lys Glu Asn
65                  70


<210> SEQ ID NO 45
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 45

Thr Asn Ile Asp Ser Thr Pro
 1               5


<210> SEQ ID NO 46
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 46

His Leu Gln Thr Thr Glu Thr
 1               5


<210> SEQ ID NO 47
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 47

Ser Leu Asn Asn Leu Thr Val
 1               5


<210> SEQ ID NO 48
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 48

Thr Asn Ile Asp Ser Thr Pro
 1               5


<210> SEQ ID NO 49
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 49

Thr Asn Ile Asp Ser Thr Pro
 1               5


<210> SEQ ID NO 50
```

-continued

<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 50

Leu Arg Ile Leu Ala Asn Lys
1 5

<210> SEQ ID NO 51
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 51

Arg Thr Gln Pro Tyr Pro Leu
1 5

<210> SEQ ID NO 52
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 52

Leu Leu Thr Pro Thr Leu Asn
1 5

<210> SEQ ID NO 53
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 53

Ala Leu Pro Thr His Ser Asn
1 5

<210> SEQ ID NO 54
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 54

Thr Asn Ile Asp Ser Thr Pro
1 5

<210> SEQ ID NO 55
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 55

Leu Cys Arg Arg Phe Glu Asn
1 5

<210> SEQ ID NO 56
<211> LENGTH: 7

-continued

<212> TYPE: PRT
<213> ORGANISM: Artificial Sequence
<220> FEATURE:
<223> OTHER INFORMATION: synthesized FGF-5 binding peptide

<400> SEQUENCE: 56

Thr Asn Ile Asp Ser Thr Pro
1 5

<210> SEQ ID NO 57
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 57

Thr Asn Ile Asp Ser Thr Pro
1 5

<210> SEQ ID NO 58
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 58

His Leu Gln Thr Thr Glu Thr
1 5

<210> SEQ ID NO 59
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 59

Pro Leu Gly Leu Cys Pro Pro
1 5

<210> SEQ ID NO 60
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 60

Gly Tyr Phe Ile Pro Ser Ile
1 5

<210> SEQ ID NO 61
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 61

Thr Lys Ile Asp Ser Thr Pro
1 5

<210> SEQ ID NO 62
<211> LENGTH: 7
<212> TYPE: PRT

-continued

<213> ORGANISM: Artificial Sequence
<220> FEATURE:
<223> OTHER INFORMATION: synthesized FGF-5 binding peptide

<400> SEQUENCE: 62

His Leu Gln Thr Thr Glu Thr
1 5

<210> SEQ ID NO 63
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 63

Trp Asn Ile Asp Ser Thr Pro
1 5

<210> SEQ ID NO 64
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 64

Thr Trp Ile Asp Ser Thr Pro
1 5

<210> SEQ ID NO 65
<211> LENGTH: 7
<212> TYPE: PRT
<213> ORGANISM: Artificial Sequence
<220> FEATURE:
<223> OTHER INFORMATION: synthesized FGF-5 binding peptide

<400> SEQUENCE: 65

Thr Trp Ile Asp Trp Thr Pro
1 5

<210> SEQ ID NO 66
<211> LENGTH: 47
<212> TYPE: DNA
<213> ORGANISM: Artificial Sequence
<220> FEATURE:
<223> OTHER INFORMATION: synthetic oligonucleotide primer

<400> SEQUENCE: 66
gctattcaat gtcagacgaa gacgtcgttc ctttctattc tcactct 47

<210> SEQ ID NO 67
<211> LENGTH: 36
<212> TYPE: DNA
<213> ORGANISM: Artificial Sequence
<220> FEATURE:
<223> OTHER INFORMATION: synthetic oligonucleotide primer

<400> SEQUENCE: 67
ggtggaggtt cggcgtcttc ccgactgaat ggctat 36

<210> SEQ ID NO 68
<211> LENGTH: 56
<212> TYPE: DNA
<213> ORGANISM: Artificial Sequence
<220> FEATURE:
<223> OTHER INFORMATION: synthetic oligonucleotide primer -continued

<400> SEQUENCE: 68
tcaatgcgca tgtgaagaga tctggactat gctttgccgg tgttccgata tgcgtc 56

<210> SEQ ID NO 69
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 69
cggaacaccg gcaaagcata gtccagatct cttcacatgc gcattgatcg caacagg 57

<210> SEQ ID NO 70
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 70
tcaatgcgca tgttgggccc ttactgtcaa aacatgccgg tgttccgata tgcgtc 56

<210> SEQ ID NO 71
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 71
cggaacaccg gcatgttttg acagtaaggg cccaacatgc gcattgatcg caacagg 57

<210> SEQ ID NO 72
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 72
tcaatgcgca tgtcttacag tactgtggac tacatgccgg tgttccgata tgcgtc 56

<210> SEQ ID NO 73
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 73
cggaacaccg gcatgtagtc cacagtactg taagacatgc gcattgatcg caacagg 57

<210> SEQ ID NO 74
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 74
tcaatgcgca tgtactcttt ggaacagatc tccttgccgg tgttccgata tgcgtc 56

<210> SEQ ID NO 75

-continued

<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 75
cggaacaccg gcaaggagat ctgttccaaa gagtacatgc gcattgatcg caacagg 57

<210> SEQ ID NO 76
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 76
caaaagctgt gcttgtgaag agatctggac tatgctttgc ttttgcgtcg acatcacgg 59

<210> SEQ ID NO 77
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 77
acgcaaaagc aaagcatagt ccagatctct tcacaagcac agcttttgca tgcactatg 59

<210> SEQ ID NO 78
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 78
caaaagctgt gcttgttggg cccttactgt caaaacatgc ttttgcgtcg acatcacgg 59

<210> SEQ ID NO 79
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 79
acgcaaaagc atgttttgac agtaagggcc caacaagcac agcttttgca tgcactatg 59

<210> SEQ ID NO 80
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 80
cggaacaccg gcatgttttg acagtaaggg cccaacatgc gcattgatcg caacagg 57

<210> SEQ ID NO 81
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 81

-continued acgcaaaagc atgtagtcca cagtactgta agacaagcac agcttttgca tgcactatg 59

<210> SEQ ID NO 82
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 82
caaaagctgt gcttgtactc tttggaatcg atctccttgc ttttgcgtcg acatcacgg 59

<210> SEQ ID NO 83
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 83
acgcaaaagc aaggagatcg attccaaaga gtacaagcac agcttttgca tgcactatg 59

<210> SEQ ID NO 84

<400> SEQUENCE: 84

000

<210> SEQ ID NO 85
<211> LENGTH: 1155
<212> TYPE: DNA
<213> ORGANISM: Artificial Sequence
<220> FEATURE:
<223> OTHER INFORMATION: sequence encoding SEQ ID NO:86

<400> SEQUENCE: 85
gatgattatt cagttgtaga ggaacatggg caactaagta ttagtaacgg tgaattagtc 60
aatgaacgag gcgaacaagt tcagttaaaa gggatgagtt cccatggttt gcaatggtac 120
ggtcaatttg taaactatga aagcatgaaa tggctaagag atgattgggg aataactgta 180
ttccgagcag caatgtatac ctcttcagga ggatatattg acgatccatc agtaaaggaa 240
aaagtaaaag agactgttga ggctgcgata gaccttggca tatatgtgat cattgattgg 300
catatccttt cagacaatga cccgaatata tataaagaag aagcgaagga tttctttgat 360
gaaatgtcag agttgtatgg agactatccg aatgtgatat acgaaattgc aaatgaaccg 420
aatggtagtg atgttacgtg ggacaatcaa ataaaaccgt atgcagaaga agtgattccg 480
gttattcgtg acaatgaccc taataacatt gttattgtag gtacaggtac atggagtcag 540
gatgtccatc atgcagccga taatcagctt gcagatccta acgtcatgta tgcatttcat 600
ttttatgcag gaacacatgg acaaaattta cgagaccaag tagattatgc attagatcaa 660
ggagcagcga tatttgttag tgaatggggg acaagtgcag ctacaggtga tggtggtgtg 720
tttttagatg aagcacaagt gtggattgac tttatggatg aaagaaattt aagctgggcc 780
aactggtctc taacgcataa ggatgagtca tctgcagcgt taatgccagg tgcaaatcca 840
actggtggtt ggacagaggc tgaactatct ccatctggta catttgtgag ggaaaaaata 900
agagaatcag catctgacaa caatgatccc ataccggatc cagacgatga gagctctaaa 960
ccctgttgcg atcaatgcgc atgtgaagag atctggacta tgctttgccg gtgttccgat 1020
atgcgtctga atagctgtca tagtgcatgc aaaagctgta tctgcgccct gagttatcca 1080

-continued

```
gctcaatgtt tttgcgtcga catcacggac ttctgctatg agccatgtaa accaagcgag   1140

gacgataaag agaac                                                    1155


<210> SEQ ID NO 86
<211> LENGTH: 385
<212> TYPE: PRT
<213> ORGANISM: Artificial Sequence
<220> FEATURE:
<223> OTHER INFORMATION: BBI-FGF-5 binding peptide construct

<400> SEQUENCE: 86

Asp Asp Tyr Ser Val Val Glu Glu His Gly Gln Leu Ser Ile Ser Asn
 1               5                  10                  15

Gly Glu Leu Val Asn Glu Arg Gly Glu Gln Val Gln Leu Lys Gly Met
            20                  25                  30

Ser Ser His Gly Leu Gln Trp Tyr Gly Gln Phe Val Asn Tyr Glu Ser
        35                  40                  45

Met Lys Trp Leu Arg Asp Asp Trp Gly Ile Thr Val Phe Arg Ala Ala
    50                  55                  60

Met Tyr Thr Ser Ser Gly Gly Tyr Ile Asp Asp Pro Ser Val Lys Glu
65                  70                  75                  80

Lys Val Lys Glu Thr Val Glu Ala Ala Ile Asp Leu Gly Ile Tyr Val
                85                  90                  95

Ile Ile Asp Trp His Ile Leu Ser Asp Asn Asp Pro Asn Ile Tyr Lys
            100                 105                 110

Glu Glu Ala Lys Asp Phe Phe Asp Glu Met Ser Glu Leu Tyr Gly Asp
        115                 120                 125

Tyr Pro Asn Val Ile Tyr Glu Ile Ala Asn Glu Pro Asn Gly Ser Asp
    130                 135                 140

Val Thr Trp Asp Asn Gln Ile Lys Pro Tyr Ala Glu Glu Val Ile Pro
145                 150                 155                 160

Val Ile Arg Asp Asn Asp Pro Asn Asn Ile Val Ile Val Gly Thr Gly
                165                 170                 175

Thr Trp Ser Gln Asp Val His His Ala Ala Asp Asn Gln Leu Ala Asp
            180                 185                 190

Pro Asn Val Met Tyr Ala Phe His Phe Tyr Ala Gly Thr His Gly Gln
        195                 200                 205

Asn Leu Arg Asp Gln Val Asp Tyr Ala Leu Asp Gln Gly Ala Ala Ile
    210                 215                 220

Phe Val Ser Glu Trp Gly Thr Ser Ala Ala Thr Gly Asp Gly Gly Val
225                 230                 235                 240

Phe Leu Asp Glu Ala Gln Val Trp Ile Asp Phe Met Asp Glu Arg Asn
                245                 250                 255

Leu Ser Trp Ala Asn Trp Ser Leu Thr His Lys Asp Glu Ser Ser Ala
            260                 265                 270

Ala Leu Met Pro Gly Ala Asn Pro Thr Gly Gly Trp Thr Glu Ala Glu
        275                 280                 285

Leu Ser Pro Ser Gly Thr Phe Val Arg Glu Lys Ile Arg Glu Ser Ala
    290                 295                 300

Ser Asp Asn Asn Asp Pro Ile Pro Asp Pro Asp Asp Glu Ser Ser Lys
305                 310                 315                 320

Pro Cys Cys Asp Gln Cys Ala Cys Glu Glu Ile Trp Thr Met Leu Cys
                325                 330                 335

Arg Cys Ser Asp Met Arg Leu Asn Ser Cys His Ser Ala Cys Lys Ser
```

-continued

```
        340                 345                 350

Cys Ile Cys Ala Leu Ser Tyr Pro Ala Gln Cys Phe Cys Val Asp Ile
        355                 360                 365

Thr Asp Phe Cys Tyr Glu Pro Cys Lys Pro Ser Glu Asp Asp Lys Glu
    370                 375                 380

Asn
385
```

<210> SEQ ID NO 87
<211> LENGTH: 1155
<212> TYPE: DNA
<213> ORGANISM: Artificial Sequence
<220> FEATURE:
<223> OTHER INFORMATION: sequence encoding SEQ ID NO:88

<400> SEQUENCE: 87

```
gatgattatt cagttgtaga ggaacatggg caactaagta ttagtaacgg tgaattagtc     60

aatgaacgag gcgaacaagt tcagttaaaa gggatgagtt cccatggttt gcaatggtac    120

ggtcaatttg taaactatga aagcatgaaa tggctaagag atgattgggg aataactgta    180

ttccgagcag caatgtatac ctcttcagga ggatatattg acgatccatc agtaaaggaa    240

aaagtaaaag agactgttga ggctgcgata gaccttggca tatatgtgat cattgattgg    300

catatccttt cagacaatga cccgaatata tataaagaag aagcgaagga tttctttgat    360

gaaatgtcag agttgtatgg agactatccg aatgtgatat acgaaattgc aaatgaaccg    420

aatggtagtg atgttacgtg ggacaatcaa ataaaaccgt atgcagaaga agtgattccg    480

gttattcgtg acaatgaccc taataacatt gttattgtag gtacaggtac atggagtcag    540

gatgtccatc atgcagccga taatcagctt gcagatccta acgtcatgta tgcatttcat    600

ttttatgcag gaacacatgg acaaaattta cgagaccaag tagattatgc attagatcaa    660

ggagcagcga tatttgttag tgaatggggg acaagtgcag ctacaggtga tggtggtgtg    720

tttttagatg aagcacaagt gtggattgac tttatggatg aaagaaattt aagctgggcc    780

aactggtctc taacgcataa ggatgagtca tctgcagcgt taatgccagg tgcaaatcca    840

actggtggtt ggacagaggc tgaactatct ccatctggta catttgtgag ggaaaaaata    900

agagaatcag catctgacaa caatgatccc ataccggatc cagacgatga gagctctaaa    960

ccctgttgcg atcaatgcgc atgttgggcc cttactgtca aaacatgccg gtgttccgat   1020

atgcgtctga atagctgtca tagtgcatgc aaaagctgta tctgcgccct gagttatcca   1080

gctcaatgtt tttgcgtcga catcacggac ttctgctatg agccatgtaa accaagcgag   1140

gacgataaag agaac                                                    1155
```

<210> SEQ ID NO 88
<211> LENGTH: 385
<212> TYPE: PRT
<213> ORGANISM: Artificial Sequence
<220> FEATURE:
<223> OTHER INFORMATION: BBI-FGF-5 binding peptide construct

<400> SEQUENCE: 88

```
Asp Asp Tyr Ser Val Val Glu Glu His Gly Gln Leu Ser Ile Ser Asn
 1               5                  10                  15

Gly Glu Leu Val Asn Glu Arg Gly Glu Gln Val Gln Leu Lys Gly Met
            20                  25                  30

Ser Ser His Gly Leu Gln Trp Tyr Gly Gln Phe Val Asn Tyr Glu Ser
        35                  40                  45
```

-continued

```
Met Lys Trp Leu Arg Asp Asp Trp Gly Ile Thr Val Phe Arg Ala Ala
    50                  55                  60

Met Tyr Thr Ser Ser Gly Gly Tyr Ile Asp Asp Pro Ser Val Lys Glu
65                  70                  75                  80

Lys Val Lys Glu Thr Val Glu Ala Ala Ile Asp Leu Gly Ile Tyr Val
                85                  90                  95

Ile Ile Asp Trp His Ile Leu Ser Asp Asn Asp Pro Asn Ile Tyr Lys
            100                 105                 110

Glu Glu Ala Lys Asp Phe Phe Asp Glu Met Ser Glu Leu Tyr Gly Asp
        115                 120                 125

Tyr Pro Asn Val Ile Tyr Glu Ile Ala Asn Glu Pro Asn Gly Ser Asp
    130                 135                 140

Val Thr Trp Asp Asn Gln Ile Lys Pro Tyr Ala Glu Glu Val Ile Pro
145                 150                 155                 160

Val Ile Arg Asp Asn Asp Pro Asn Asn Ile Val Ile Val Gly Thr Gly
                165                 170                 175

Thr Trp Ser Gln Asp Val His His Ala Ala Asp Asn Gln Leu Ala Asp
            180                 185                 190

Pro Asn Val Met Tyr Ala Phe His Phe Tyr Ala Gly Thr His Gly Gln
        195                 200                 205

Asn Leu Arg Asp Gln Val Asp Tyr Ala Leu Asp Gln Gly Ala Ala Ile
    210                 215                 220

Phe Val Ser Glu Trp Gly Thr Ser Ala Ala Thr Gly Asp Gly Gly Val
225                 230                 235                 240

Phe Leu Asp Glu Ala Gln Val Trp Ile Asp Phe Met Asp Glu Arg Asn
                245                 250                 255

Leu Ser Trp Ala Asn Trp Ser Leu Thr His Lys Asp Glu Ser Ser Ala
            260                 265                 270

Ala Leu Met Pro Gly Ala Asn Pro Thr Gly Gly Trp Thr Glu Ala Glu
        275                 280                 285

Leu Ser Pro Ser Gly Thr Phe Val Arg Glu Lys Ile Arg Glu Ser Ala
    290                 295                 300

Ser Asp Asn Asn Asp Pro Ile Pro Asp Pro Asp Asp Glu Ser Ser Lys
305                 310                 315                 320

Pro Cys Cys Asp Gln Cys Ala Cys Trp Ala Leu Thr Val Lys Thr Cys
                325                 330                 335

Arg Cys Ser Asp Met Arg Leu Asn Ser Cys His Ser Ala Cys Lys Ser
            340                 345                 350

Cys Ile Cys Ala Leu Ser Tyr Pro Ala Gln Cys Phe Cys Val Asp Ile
        355                 360                 365

Thr Asp Phe Cys Tyr Glu Pro Cys Lys Pro Ser Glu Asp Asp Lys Glu
    370                 375                 380

Asn
385


<210> SEQ ID NO 89
<211> LENGTH: 1155
<212> TYPE: DNA
<213> ORGANISM: Artificial Sequence
<220> FEATURE:
<223> OTHER INFORMATION: sequence encoding SEQ ID NO:90

<400> SEQUENCE: 89

gatgattatt cagttgtaga ggaacatggg caactaagta ttagtaacgg tgaattagtc      60
```

-continued

```
aatgaacgag gcgaacaagt tcagttaaaa gggatgagtt cccatggttt gcaatggtac    120

ggtcaatttg taaactatga aagcatgaaa tggctaagag atgattgggg aataactgta    180

ttccgagcag caatgtatac ctcttcagga ggatatattg acgatccatc agtaaaggaa    240

aaagtaaaag agactgttga ggctgcgata gaccttggca tatatgtgat cattgattgg    300

catatccttt cagacaatga cccgaatata tataaagaag aagcgaagga tttctttgat    360

gaaatgtcag agttgtatgg agactatccg aatgtgatat acgaaattgc aaatgaaccg    420

aatggtagtg atgttacgtg ggacaatcaa ataaaaccgt atgcagaaga agtgattccg    480

gttattcgtg acaatgaccc taataacatt gttattgtag gtacaggtac atggagtcag    540

gatgtccatc atgcagccga taatcagctt gcagatccta acgtcatgta tgcatttcat    600

ttttatgcag gaacacatgg acaaaattta cgagaccaag tagattatgc attagatcaa    660

ggagcagcga tatttgttag tgaatggggg acaagtgcag ctacaggtga tggtggtgtg    720

tttttagatg aagcacaagt gtggattgac tttatggatg aaagaaattt aagctgggcc    780

aactggtctc taacgcataa ggatgagtca tctgcagcgt taatgccagg tgcaaatcca    840

actggtggtt ggacagaggc tgaactatct ccatctggta catttgtgag ggaaaaaata    900

agagaatcag catctgacaa caatgatccc ataccggatc cagacgatga gagctctaaa    960

ccctgttgcg atcaatgcgc atgtcttaca gtactgtgga ctacatgccg gtgttccgat   1020

atgcgtctga atagctgtca tagtgcatgc aaaagctgta tctgcgccct gagttatcca   1080

gctcaatgtt tttgcgtcga catcacggac ttctgctatg agccatgtaa accaagcgag   1140

gacgataaag agaac                                                    1155
```

<210> SEQ ID NO 90
<211> LENGTH: 385
<212> TYPE: PRT
<213> ORGANISM: Artificial Sequence
<220> FEATURE:
<223> OTHER INFORMATION: BBI-FGF-5 binding peptide construct

<400> SEQUENCE: 90

```
Asp Asp Tyr Ser Val Val Glu Glu His Gly Gln Leu Ser Ile Ser Asn
 1               5                  10                  15

Gly Glu Leu Val Asn Glu Arg Gly Glu Gln Val Gln Leu Lys Gly Met
            20                  25                  30

Ser Ser His Gly Leu Gln Trp Tyr Gly Gln Phe Val Asn Tyr Glu Ser
        35                  40                  45

Met Lys Trp Leu Arg Asp Asp Trp Gly Ile Thr Val Phe Arg Ala Ala
    50                  55                  60

Met Tyr Thr Ser Ser Gly Gly Tyr Ile Asp Asp Pro Ser Val Lys Glu
65                  70                  75                  80

Lys Val Lys Glu Thr Val Glu Ala Ala Ile Asp Leu Gly Ile Tyr Val
                85                  90                  95

Ile Ile Asp Trp His Ile Leu Ser Asp Asn Asp Pro Asn Ile Tyr Lys
            100                 105                 110

Glu Glu Ala Lys Asp Phe Phe Asp Glu Met Ser Glu Leu Tyr Gly Asp
        115                 120                 125

Tyr Pro Asn Val Ile Tyr Glu Ile Ala Asn Glu Pro Asn Gly Ser Asp
    130                 135                 140

Val Thr Trp Asp Asn Gln Ile Lys Pro Tyr Ala Glu Glu Val Ile Pro
145                 150                 155                 160

Val Ile Arg Asp Asn Asp Pro Asn Asn Ile Val Ile Val Gly Thr Gly
```

-continued

```
                165                 170                 175

Thr Trp Ser Gln Asp Val His His Ala Ala Asp Asn Gln Leu Ala Asp
            180                 185                 190

Pro Asn Val Met Tyr Ala Phe His Phe Tyr Ala Gly Thr His Gly Gln
        195                 200                 205

Asn Leu Arg Asp Gln Val Asp Tyr Ala Leu Asp Gln Gly Ala Ala Ile
    210                 215                 220

Phe Val Ser Glu Trp Gly Thr Ser Ala Ala Thr Gly Asp Gly Gly Val
225                 230                 235                 240

Phe Leu Asp Glu Ala Gln Val Trp Ile Asp Phe Met Asp Glu Arg Asn
                245                 250                 255

Leu Ser Trp Ala Asn Trp Ser Leu Thr His Lys Asp Glu Ser Ser Ala
            260                 265                 270

Ala Leu Met Pro Gly Ala Asn Pro Thr Gly Gly Trp Thr Glu Ala Glu
        275                 280                 285

Leu Ser Pro Ser Gly Thr Phe Val Arg Glu Lys Ile Arg Glu Ser Ala
    290                 295                 300

Ser Asp Asn Asn Asp Pro Ile Pro Asp Pro Asp Asp Glu Ser Ser Lys
305                 310                 315                 320

Pro Cys Cys Asp Gln Cys Ala Cys Leu Thr Val Leu Trp Thr Thr Cys
                325                 330                 335

Arg Cys Ser Asp Met Arg Leu Asn Ser Cys His Ser Ala Cys Lys Ser
            340                 345                 350

Cys Ile Cys Ala Leu Ser Tyr Pro Ala Gln Cys Phe Cys Val Asp Ile
        355                 360                 365

Thr Asp Phe Cys Tyr Glu Pro Cys Lys Pro Ser Glu Asp Asp Lys Glu
    370                 375                 380

Asn
385
```

<210> SEQ ID NO 91
<211> LENGTH: 1155
<212> TYPE: DNA
<213> ORGANISM: Artificial Sequence
<220> FEATURE:
<223> OTHER INFORMATION: sequence encoding SEQ ID NO:92

<400> SEQUENCE: 91

```
gatgattatt cagttgtaga ggaacatggg caactaagta ttagtaacgg tgaattagtc      60

aatgaacgag gcgaacaagt tcagttaaaa gggatgagtt cccatggttt gcaatggtac     120

ggtcaatttg taaactatga aagcatgaaa tggctaagag atgattgggg aataactgta     180

ttccgagcag caatgtatac ctcttcagga ggatatattg acgatccatc agtaaaggaa     240

aaagtaaaag agactgttga ggctgcgata gaccttggca tatatgtgat cattgattgg     300

catatccttt cagacaatga cccgaatata tataaagaag aagcgaagga tttctttgat     360

gaaatgtcag agttgtatgg agactatccg aatgtgatat acgaaattgc aaatgaaccg     420

aatggtagtg atgttacgtg ggacaatcaa ataaaaccgt atgcagaaga agtgattccg     480

gttattcgtg acaatgaccc taataacatt gttattgtag gtacaggtac atggagtcag     540

gatgtccatc atgcagccga taatcagctt gcagatccta acgtcatgta tgcatttcat     600

ttttatgcag gaacacatgg acaaaattta cgagaccaag tagattatgc attagatcaa     660

ggagcagcga tatttgttag tgaatggggg acaagtgcag ctacaggtga tggtggtgtg     720

tttttagatg aagcacaagt gtggattgac tttatggatg aaagaaattt aagctgggcc     780
```

-continued

```
aactggtctc taacgcataa ggatgagtca tctgcagcgt taatgccagg tgcaaatcca    840

actggtggtt ggacagaggc tgaactatct ccatctggta catttgtgag ggaaaaaata    900

agagaatcag catctgacaa caatgatccc ataccggatc cagacgatga gagctctaaa    960

ccctgttgcg atcaatgcgc atgtactctt tggaacagat ctccttgccg gtgttccgat   1020

atgcgtctga atagctgtca tagtgcatgc aaaagctgta tctgcgccct gagttatcca   1080

gctcaatgtt tttgcgtcga catcacggac ttctgctatg agccatgtaa accaagcgag   1140

gacgataaag agaac                                                     1155


<210> SEQ ID NO 92
<211> LENGTH: 385
<212> TYPE: PRT
<213> ORGANISM: Artificial Sequence
<220> FEATURE:
<223> OTHER INFORMATION: BBI-FGF-5 binding peptide construct

<400> SEQUENCE: 92

Asp Asp Tyr Ser Val Val Glu Glu His Gly Gln Leu Ser Ile Ser Asn
 1               5                  10                  15

Gly Glu Leu Val Asn Glu Arg Gly Glu Gln Val Gln Leu Lys Gly Met
            20                  25                  30

Ser Ser His Gly Leu Gln Trp Tyr Gly Gln Phe Val Asn Tyr Glu Ser
        35                  40                  45

Met Lys Trp Leu Arg Asp Asp Trp Gly Ile Thr Val Phe Arg Ala Ala
    50                  55                  60

Met Tyr Thr Ser Ser Gly Gly Tyr Ile Asp Asp Pro Ser Val Lys Glu
65                  70                  75                  80

Lys Val Lys Glu Thr Val Glu Ala Ala Ile Asp Leu Gly Ile Tyr Val
                85                  90                  95

Ile Ile Asp Trp His Ile Leu Ser Asp Asn Asp Pro Asn Ile Tyr Lys
            100                 105                 110

Glu Glu Ala Lys Asp Phe Phe Asp Glu Met Ser Glu Leu Tyr Gly Asp
        115                 120                 125

Tyr Pro Asn Val Ile Tyr Glu Ile Ala Asn Glu Pro Asn Gly Ser Asp
    130                 135                 140

Val Thr Trp Asp Asn Gln Ile Lys Pro Tyr Ala Glu Glu Val Ile Pro
145                 150                 155                 160

Val Ile Arg Asp Asn Asp Pro Asn Asn Ile Val Ile Val Gly Thr Gly
                165                 170                 175

Thr Trp Ser Gln Asp Val His His Ala Ala Asp Asn Gln Leu Ala Asp
            180                 185                 190

Pro Asn Val Met Tyr Ala Phe His Phe Tyr Ala Gly Thr His Gly Gln
        195                 200                 205

Asn Leu Arg Asp Gln Val Asp Tyr Ala Leu Asp Gln Gly Ala Ala Ile
    210                 215                 220

Phe Val Ser Glu Trp Gly Thr Ser Ala Ala Thr Gly Asp Gly Gly Val
225                 230                 235                 240

Phe Leu Asp Glu Ala Gln Val Trp Ile Asp Phe Met Asp Glu Arg Asn
                245                 250                 255

Leu Ser Trp Ala Asn Trp Ser Leu Thr His Lys Asp Glu Ser Ser Ala
            260                 265                 270

Ala Leu Met Pro Gly Ala Asn Pro Thr Gly Gly Trp Thr Glu Ala Glu
        275                 280                 285
```

-continued

Leu Ser Pro Ser Gly Thr Phe Val Arg Glu Lys Ile Arg Glu Ser Ala
290 295 300

Ser Asp Asn Asn Asp Pro Ile Pro Asp Pro Asp Asp Glu Ser Ser Lys
305 310 315 320

Pro Cys Cys Asp Gln Cys Ala Cys Thr Leu Trp Asn Arg Ser Pro Cys
325 330 335

Arg Cys Ser Asp Met Arg Leu Asn Ser Cys His Ser Ala Cys Lys Ser
340 345 350

Cys Ile Cys Ala Leu Ser Tyr Pro Ala Gln Cys Phe Cys Val Asp Ile
355 360 365

Thr Asp Phe Cys Tyr Glu Pro Cys Lys Pro Ser Glu Asp Asp Lys Glu
370 375 380

Asn
385

<210> SEQ ID NO 93
<211> LENGTH: 1155
<212> TYPE: DNA
<213> ORGANISM: Artificial Sequence
<220> FEATURE:
<223> OTHER INFORMATION: sequence encoding SEQ ID NO:95

<400> SEQUENCE: 93
gatgattatt cagttgtaga ggaacatggg caactaagta ttagtaacgg tgaattagtc 60
aatgaacgag gcgaacaagt tcagttaaaa gggatgagtt cccatggttt gcaatggtac 120
ggtcaatttg taaactatga aagcatgaaa tggctaagag atgattgggg aataactgta 180
8
ttccgagcag caatgtatac ctcttcagga ggatatattg acgatccatc agtaaaggaa 240
aaagtaaaag agactgttga ggctgcgata gaccttggca tatatgtgat cattgattgg 300
catatccttt cagacaatga cccgaatata tataaagaag aagcgaagga tttctttgat 360
gaaatgtcag agttgtatgg agactatccg aatgtgatat acgaaattgc aaatgaaccg 420
aatggtagtg atgttacgtg ggacaatcaa ataaaaccgt atgcagaaga agtgattccg 480
gttattcgtg acaatgaccc taataacatt gttattgtag gtacaggtac atggagtcag 540
gatgtccatc atgcagccga taatcagctt gcagatccta acgtcatgta tgcatttcat 600
ttttatgcag gaacacatgg acaaaattta cgagaccaag tagattatgc attagatcaa 660
ggagcagcga tatttgttag tgaatggggg acaagtgcag ctacaggtga tggtggtgtg 720
tttttagatg aagcacaagt gtggattgac tttatggatg aaagaaattt aagctgggcc 780
aactggtctc taacgcataa ggatgagtca tctgcagcgt taatgccagg tgcaaatcca 840
actggtggtt ggacagaggc tgaactatct ccatctggta catttgtgag ggaaaaaata 900
agagaatcag catctgacaa caatgatccc ataccggatc cagacgatga gagctctaaa 960
ccctgttgcg atcaatgcgc atgtacgaaa tcaaatcctc cacagtgtcg gtgttccgat 1020
atgcgtctga atagctgtca tagtgcatgc aaaagctgtg cttgtgaaga gatctggact 1080
atgctttgct tttgcgtcga catcacggac ttctgctatg agccatgtaa accaagcgag 1140
gacgataaag agaac 1155

<210> SEQ ID NO 94
<211> LENGTH: 385
<212> TYPE: PRT
<213> ORGANISM: Artificial Sequence
<220> FEATURE:
<223> OTHER INFORMATION: BBI-FGF-5 binding peptide construct -continued

<400> SEQUENCE: 94

```
Asp Asp Tyr Ser Val Val Glu Glu His Gly Gln Leu Ser Ile Ser Asn
 1               5                  10                  15

Gly Glu Leu Val Asn Glu Arg Gly Glu Gln Val Gln Leu Lys Gly Met
            20                  25                  30

Ser Ser His Gly Leu Gln Trp Tyr Gly Gln Phe Val Asn Tyr Glu Ser
        35                  40                  45

Met Lys Trp Leu Arg Asp Asp Trp Gly Ile Thr Val Phe Arg Ala Ala
    50                  55                  60

Met Tyr Thr Ser Ser Gly Gly Tyr Ile Asp Asp Pro Ser Val Lys Glu
65                  70                  75                  80

Lys Val Lys Glu Thr Val Glu Ala Ala Ile Asp Leu Gly Ile Tyr Val
                85                  90                  95

Ile Ile Asp Trp His Ile Leu Ser Asp Asn Asp Pro Asn Ile Tyr Lys
            100                 105                 110

Glu Glu Ala Lys Asp Phe Phe Asp Glu Met Ser Glu Leu Tyr Gly Asp
        115                 120                 125

Tyr Pro Asn Val Ile Tyr Glu Ile Ala Asn Glu Pro Asn Gly Ser Asp
    130                 135                 140

Val Thr Trp Asp Asn Gln Ile Lys Pro Tyr Ala Glu Glu Val Ile Pro
145                 150                 155                 160

Val Ile Arg Asp Asn Asp Pro Asn Asn Ile Val Ile Val Gly Thr Gly
                165                 170                 175

Thr Trp Ser Gln Asp Val His His Ala Ala Asp Asn Gln Leu Ala Asp
            180                 185                 190

Pro Asn Val Met Tyr Ala Phe His Phe Tyr Ala Gly Thr His Gly Gln
        195                 200                 205

Asn Leu Arg Asp Gln Val Asp Tyr Ala Leu Asp Gln Gly Ala Ala Ile
    210                 215                 220

Phe Val Ser Glu Trp Gly Thr Ser Ala Ala Thr Gly Asp Gly Gly Val
225                 230                 235                 240

Phe Leu Asp Glu Ala Gln Val Trp Ile Asp Phe Met Asp Glu Arg Asn
                245                 250                 255

Leu Ser Trp Ala Asn Trp Ser Leu Thr His Lys Asp Glu Ser Ser Ala
            260                 265                 270

Ala Leu Met Pro Gly Ala Asn Pro Thr Gly Gly Trp Thr Glu Ala Glu
        275                 280                 285

Leu Ser Pro Ser Gly Thr Phe Val Arg Glu Lys Ile Arg Glu Ser Ala
    290                 295                 300

Ser Asp Asn Asn Asp Pro Ile Pro Asp Pro Asp Asp Glu Ser Ser Lys
305                 310                 315                 320

Pro Cys Cys Asp Gln Cys Ala Cys Thr Lys Ser Asn Pro Pro Gln Cys
                325                 330                 335

Arg Cys Ser Asp Met Arg Leu Asn Ser Cys His Ser Ala Cys Lys Ser
            340                 345                 350

Cys Ala Cys Glu Glu Ile Trp Thr Met Leu Cys Phe Cys Val Asp Ile
        355                 360                 365

Thr Asp Phe Cys Tyr Glu Pro Cys Lys Pro Ser Glu Asp Asp Lys Glu
    370                 375                 380

Asn
385
```

<210> SEQ ID NO 95

-continued

<211> LENGTH: 1155
<212> TYPE: DNA
<213> ORGANISM: Artificial Sequence
<220> FEATURE:
<223> OTHER INFORMATION: sequence encoding SEQ ID NO:96

<400> SEQUENCE: 95
gatgattatt cagttgtaga ggaacatggg caactaagta ttagtaacgg tgaattagtc 60
aatgaacgag gcgaacaagt tcagttaaaa gggatgagtt cccatggttt gcaatggtac 120
ggtcaatttg taaactatga aagcatgaaa tggctaagag atgattgggg aataactgta 180
ttccgagcag caatgtatac ctcttcagga ggatatattg acgatccatc agtaaaggaa 240
aaagtaaaag agactgttga ggctgcgata gaccttggca tatatgtgat cattgattgg 300
catatccttt cagacaatga cccgaatata tataaagaag aagcgaagga tttctttgat 360
gaaatgtcag agttgtatgg agactatccg aatgtgatat acgaaattgc aaatgaaccg 420
aatggtagtg atgttacgtg ggacaatcaa ataaaaccgt atgcagaaga agtgattccg 480
gttattcgtg acaatgaccc taataacatt gttattgtag gtacaggtac atggagtcag 540
gatgtccatc atgcagccga taatcagctt gcagatccta acgtcatgta tgcatttcat 600
ttttatgcag gaacacatgg acaaaattta cgagaccaag tagattatgc attagatcaa 660
ggagcagcga tatttgttag tgaatggggg acaagtgcag ctacaggtga tggtggtgtg 720
tttttagatg aagcacaagt gtggattgac tttatggatg aaagaaattt aagctgggcc 780
aactggtctc taacgcataa ggatgagtca tctgcagcgt taatgccagg tgcaaatcca 840
actggtggtt ggacagaggc tgaactatct ccatctggta catttgtgag ggaaaaaata 900
agagaatcag catctgacaa caatgatccc ataccggatc cagacgatga gagctctaaa 960
ccctgttgcg atcaatgcgc atgtacgaaa tcaaatcctc cacagtgtcg gtgttccgat 1020
atgcgtctga atagctgtca tagtgcatgc aaaagctgtg cttgttgggc ccttactgtc 1080
aaaacatgct tttgcgtcga catcacggac ttctgctatg agccatgtaa accaagcgag 1140
gacgataaag agaac 1155

<210> SEQ ID NO 96
<211> LENGTH: 385
<212> TYPE: PRT
<213> ORGANISM: Artificial Sequence
<220> FEATURE:
<223> OTHER INFORMATION: BBI-FGF-5 binding peptide construct

<400> SEQUENCE: 96

Asp Asp Tyr Ser Val Val Glu Glu His Gly Gln Leu Ser Ile Ser Asn
1 5 10 15

Gly Glu Leu Val Asn Glu Arg Gly Glu Gln Val Gln Leu Lys Gly Met
20 25 30

Ser Ser His Gly Leu Gln Trp Tyr Gly Gln Phe Val Asn Tyr Glu Ser
35 40 45

Met Lys Trp Leu Arg Asp Asp Trp Gly Ile Thr Val Phe Arg Ala Ala
50 55 60

Met Tyr Thr Ser Ser Gly Gly Tyr Ile Asp Asp Pro Ser Val Lys Glu
65 70 75 80

Lys Val Lys Glu Thr Val Glu Ala Ala Ile Asp Leu Gly Ile Tyr Val
85 90 95

Ile Ile Asp Trp His Ile Leu Ser Asp Asn Asp Pro Asn Ile Tyr Lys
100 105 110

-continued

```
Glu Glu Ala Lys Asp Phe Phe Asp Glu Met Ser Glu Leu Tyr Gly Asp
        115                 120                 125

Tyr Pro Asn Val Ile Tyr Glu Ile Ala Asn Glu Pro Asn Gly Ser Asp
    130                 135                 140

Val Thr Trp Asp Asn Gln Ile Lys Pro Tyr Ala Glu Glu Val Ile Pro
145                 150                 155                 160

Val Ile Arg Asp Asn Asp Pro Asn Asn Ile Val Ile Val Gly Thr Gly
                165                 170                 175

Thr Trp Ser Gln Asp Val His His Ala Ala Asp Asn Gln Leu Ala Asp
            180                 185                 190

Pro Asn Val Met Tyr Ala Phe His Phe Tyr Ala Gly Thr His Gly Gln
        195                 200                 205

Asn Leu Arg Asp Gln Val Asp Tyr Ala Leu Asp Gln Gly Ala Ala Ile
    210                 215                 220

Phe Val Ser Glu Trp Gly Thr Ser Ala Ala Thr Gly Asp Gly Gly Val
225                 230                 235                 240

Phe Leu Asp Glu Ala Gln Val Trp Ile Asp Phe Met Asp Glu Arg Asn
                245                 250                 255

Leu Ser Trp Ala Asn Trp Ser Leu Thr His Lys Asp Glu Ser Ser Ala
            260                 265                 270

Ala Leu Met Pro Gly Ala Asn Pro Thr Gly Gly Trp Thr Glu Ala Glu
        275                 280                 285

Leu Ser Pro Ser Gly Thr Phe Val Arg Glu Lys Ile Arg Glu Ser Ala
    290                 295                 300

Ser Asp Asn Asn Asp Pro Ile Pro Asp Pro Asp Asp Glu Ser Ser Lys
305                 310                 315                 320

Pro Cys Cys Asp Gln Cys Ala Cys Thr Lys Ser Asn Pro Pro Gln Cys
                325                 330                 335

Arg Cys Ser Asp Met Arg Leu Asn Ser Cys His Ser Ala Cys Lys Ser
            340                 345                 350

Cys Ala Cys Trp Ala Leu Thr Val Lys Thr Cys Phe Cys Val Asp Ile
        355                 360                 365

Thr Asp Phe Cys Tyr Glu Pro Cys Lys Pro Ser Glu Asp Asp Lys Glu
    370                 375                 380

Asn
385


<210> SEQ ID NO 97

<400> SEQUENCE: 97

000


<210> SEQ ID NO 98
<211> LENGTH: 1155
<212> TYPE: DNA
<213> ORGANISM: Artificial Sequence
<220> FEATURE:
<223> OTHER INFORMATION: sequence encoding SEQ ID NO:99

<400> SEQUENCE: 98

gatgattatt cagttgtaga ggaacatggg caactaagta ttagtaacgg tgaattagtc      60

aatgaacgag gcgaacaagt tcagttaaaa gggatgagtt cccatggttt gcaatggtac     120

ggtcaatttg taaactatga aagcatgaaa tggctaagag atgattgggg aataactgta     180

ttccgagcag caatgtatac ctcttcagga ggatatattg acgatccatc agtaaaggaa     240
```

-continued

```
aaagtaaaag agactgttga ggctgcgata gaccttggca tatatgtgat cattgattgg    300

catatccttt cagacaatga cccgaatata tataaagaag aagcgaagga tttctttgat    360

gaaatgtcag agttgtatgg agactatccg aatgtgatat acgaaattgc aaatgaaccg    420

aatggtagtg atgttacgtg ggacaatcaa ataaaaccgt atgcagaaga agtgattccg    480

gttattcgtg acaatgaccc taataacatt gttattgtag gtacaggtac atggagtcag    540

gatgtccatc atgcagccga taatcagctt gcagatccta acgtcatgta tgcatttcat    600

ttttatgcag gaacacatgg acaaaattta cgagaccaag tagattatgc attagatcaa    660

ggagcagcga tatttgttag tgaatggggg acaagtgcag ctacaggtga tggtggtgtg    720

tttttagatg aagcacaagt gtggattgac tttatggatg aaagaaattt aagctgggcc    780

aactggtctc taacgcataa ggatgagtca tctgcagcgt taatgccagg tgcaaatcca    840

actggtggtt ggacagaggc tgaactatct ccatctggta catttgtgag ggaaaaaata    900

agagaatcag catctgacaa caatgatccc ataccggatc cagacgatga gagctctaaa    960

ccctgttgcg atcaatgcgc atgtacgaaa tcaaatcctc cacagtgtcg gtgttccgat   1020

atgcgtctga atagctgtca tagtgcatgc aaaagctgtg cttgtcttac agtactgtgg   1080

actacatgct tttgcgtcga catcacggac ttctgctatg agccatgtaa accaagcgag   1140

gacgataaag agaac                                                     1155
```

<210> SEQ ID NO 99
<211> LENGTH: 385
<212> TYPE: PRT
<213> ORGANISM: Artificial Sequence
<220> FEATURE:
<223> OTHER INFORMATION: BBI-FGF-5 binding peptide construct

<400> SEQUENCE: 99

```
Asp Asp Tyr Ser Val Val Glu Glu His Gly Gln Leu Ser Ile Ser Asn
 1               5                  10                  15

Gly Glu Leu Val Asn Glu Arg Gly Glu Gln Val Gln Leu Lys Gly Met
            20                  25                  30

Ser Ser His Gly Leu Gln Trp Tyr Gly Gln Phe Val Asn Tyr Glu Ser
        35                  40                  45

Met Lys Trp Leu Arg Asp Asp Trp Gly Ile Thr Val Phe Arg Ala Ala
    50                  55                  60

Met Tyr Thr Ser Ser Gly Gly Tyr Ile Asp Asp Pro Ser Val Lys Glu
65                  70                  75                  80

Lys Val Lys Glu Thr Val Glu Ala Ala Ile Asp Leu Gly Ile Tyr Val
                85                  90                  95

Ile Ile Asp Trp His Ile Leu Ser Asp Asn Asp Pro Asn Ile Tyr Lys
            100                 105                 110

Glu Glu Ala Lys Asp Phe Phe Asp Glu Met Ser Glu Leu Tyr Gly Asp
        115                 120                 125

Tyr Pro Asn Val Ile Tyr Glu Ile Ala Asn Glu Pro Asn Gly Ser Asp
    130                 135                 140

Val Thr Trp Asp Asn Gln Ile Lys Pro Tyr Ala Glu Glu Val Ile Pro
145                 150                 155                 160

Val Ile Arg Asp Asn Asp Pro Asn Asn Ile Val Ile Val Gly Thr Gly
                165                 170                 175

Thr Trp Ser Gln Asp Val His His Ala Ala Asp Asn Gln Leu Ala Asp
            180                 185                 190

Pro Asn Val Met Tyr Ala Phe His Phe Tyr Ala Gly Thr His Gly Gln
```

-continued

```
        195                 200                 205

Asn Leu Arg Asp Gln Val Asp Tyr Ala Leu Asp Gln Gly Ala Ala Ile
    210                 215                 220

Phe Val Ser Glu Trp Gly Thr Ser Ala Ala Thr Gly Asp Gly Gly Val
225                 230                 235                 240

Phe Leu Asp Glu Ala Gln Val Trp Ile Asp Phe Met Asp Glu Arg Asn
                245                 250                 255

Leu Ser Trp Ala Asn Trp Ser Leu Thr His Lys Asp Glu Ser Ser Ala
            260                 265                 270

Ala Leu Met Pro Gly Ala Asn Pro Thr Gly Gly Trp Thr Glu Ala Glu
        275                 280                 285

Leu Ser Pro Ser Gly Thr Phe Val Arg Glu Lys Ile Arg Glu Ser Ala
    290                 295                 300

Ser Asp Asn Asn Asp Pro Ile Pro Asp Pro Asp Asp Glu Ser Ser Lys
305                 310                 315                 320

Pro Cys Cys Asp Gln Cys Ala Cys Thr Lys Ser Asn Pro Pro Gln Cys
                325                 330                 335

Arg Cys Ser Asp Met Arg Leu Asn Ser Cys His Ser Ala Cys Lys Ser
            340                 345                 350

Cys Ala Cys Leu Thr Val Leu Trp Thr Thr Cys Phe Cys Val Asp Ile
        355                 360                 365

Thr Asp Phe Cys Tyr Glu Pro Cys Lys Pro Ser Glu Asp Asp Lys Glu
    370                 375                 380

Asn
385
```

<210> SEQ ID NO 100
<211> LENGTH: 1155
<212> TYPE: DNA
<213> ORGANISM: Artificial Sequence
<220> FEATURE:
<223> OTHER INFORMATION: sequence encoding SEQ ID NO:101

<400> SEQUENCE: 100

```
gatgattatt cagttgtaga ggaacatggg caactaagta ttagtaacgg tgaattagtc      60

aatgaacgag gcgaacaagt tcagttaaaa gggatgagtt cccatggttt gcaatggtac     120

ggtcaatttg taaactatga aagcatgaaa tggctaagag atgattgggg aataactgta     180

ttccgagcag caatgtatac ctcttcagga ggatatattg acgatccatc agtaaaggaa     240

aaagtaaaag agactgttga ggctgcgata gaccttggca tatatgtgat cattgattgg     300

catatccttt cagacaatga cccgaatata tataaagaag aagcgaagga tttctttgat     360

gaaatgtcag agttgtatgg agactatccg aatgtgatat acgaaattgc aaatgaaccg     420

aatggtagtg atgttacgtg ggacaatcaa ataaaaccgt atgcagaaga agtgattccg     480

gttattcgtg acaatgaccc taataacatt gttattgtag gtacaggtac atggagtcag     540

gatgtccatc atgcagccga taatcagctt gcagatccta acgtcatgta tgcatttcat     600

ttttatgcag gaacacatgg acaaaattta cgagaccaag tagattatgc attagatcaa     660

ggagcagcga tatttgttag tgaatggggg acaagtgcag ctacaggtga tggtggtgtg     720

tttttagatg aagcacaagt gtggattgac tttatggatg aaagaaattt aagctgggcc     780

aactggtctc taacgcataa ggatgagtca tctgcagcgt taatgccagg tgcaaatcca     840

actggtggtt ggacagaggc tgaactatct ccatctggta catttgtgag ggaaaaaata     900

agagaatcag catctgacaa caatgatccc ataccggatc cagacgatga gagctctaaa     960
```

-continued ccctgttgcg atcaatgcgc atgtacgaaa tcaaatcctc cacagtgtcg gtgttccgat 1020
atgcgtctga atagctgtca tagtgcatgc aaaagctgtg cttgtactct ttggaatcga 1080
tctccttgct tttgcgtcga catcacggac ttctgctatg agccatgtaa accaagcgag 1140
gacgataaag agaac 1155

<210> SEQ ID NO 101
<211> LENGTH: 385
<212> TYPE: PRT
<213> ORGANISM: Artificial Sequence
<220> FEATURE:
<223> OTHER INFORMATION: BBI-FGF-5 binding peptide construct

<400> SEQUENCE: 101

Asp Asp Tyr Ser Val Val Glu Glu His Gly Gln Leu Ser Ile Ser Asn
1 5 10 15

Gly Glu Leu Val Asn Glu Arg Gly Glu Gln Val Gln Leu Lys Gly Met
20 25 30

Ser Ser His Gly Leu Gln Trp Tyr Gly Gln Phe Val Asn Tyr Glu Ser
35 40 45

Met Lys Trp Leu Arg Asp Asp Trp Gly Ile Thr Val Phe Arg Ala Ala
50 55 60

Met Tyr Thr Ser Ser Gly Gly Tyr Ile Asp Asp Pro Ser Val Lys Glu
65 70 75 80

Lys Val Lys Glu Thr Val Glu Ala Ala Ile Asp Leu Gly Ile Tyr Val
85 90 95

Ile Ile Asp Trp His Ile Leu Ser Asp Asn Asp Pro Asn Ile Tyr Lys
100 105 110

Glu Glu Ala Lys Asp Phe Phe Asp Glu Met Ser Glu Leu Tyr Gly Asp
115 120 125

Tyr Pro Asn Val Ile Tyr Glu Ile Ala Asn Glu Pro Asn Gly Ser Asp
130 135 140

Val Thr Trp Asp Asn Gln Ile Lys Pro Tyr Ala Glu Glu Val Ile Pro
145 150 155 160

Val Ile Arg Asp Asn Asp Pro Asn Asn Ile Val Ile Val Gly Thr Gly
165 170 175

Thr Trp Ser Gln Asp Val His His Ala Ala Asp Asn Gln Leu Ala Asp
180 185 190

Pro Asn Val Met Tyr Ala Phe His Phe Tyr Ala Gly Thr His Gly Gln
195 200 205

Asn Leu Arg Asp Gln Val Asp Tyr Ala Leu Asp Gln Gly Ala Ala Ile
210 215 220

Phe Val Ser Glu Trp Gly Thr Ser Ala Ala Thr Gly Asp Gly Gly Val
225 230 235 240

Phe Leu Asp Glu Ala Gln Val Trp Ile Asp Phe Met Asp Glu Arg Asn
245 250 255

Leu Ser Trp Ala Asn Trp Ser Leu Thr His Lys Asp Glu Ser Ser Ala
260 265 270

Ala Leu Met Pro Gly Ala Asn Pro Thr Gly Gly Trp Thr Glu Ala Glu
275 280 285

Leu Ser Pro Ser Gly Thr Phe Val Arg Glu Lys Ile Arg Glu Ser Ala
290 295 300

Ser Asp Asn Asn Asp Pro Ile Pro Asp Pro Asp Asp Glu Ser Ser Lys
305 310 315 320

-continued

```
Pro Cys Cys Asp Gln Cys Ala Cys Thr Lys Ser Asn Pro Pro Gln Cys
                325                 330                 335

Arg Cys Ser Asp Met Arg Leu Asn Ser Cys His Ser Ala Cys Lys Ser
            340                 345                 350

Cys Ala Cys Thr Leu Trp Asn Arg Ser Pro Cys Phe Cys Val Asp Ile
        355                 360                 365

Thr Asp Phe Cys Tyr Glu Pro Cys Lys Pro Ser Glu Asp Asp Lys Glu
    370                 375                 380

Asn
385
```